United States Patent
Lesniak et al.

(10) Patent No.: US 10,898,594 B2
(45) Date of Patent: Jan. 26, 2021

(54) PAMAM DENDRIMER BASED CEST IMAGING AGENTS AND USES THEREOF

(71) Applicant: THE JOHNS HOPKINS UNIVERSITY, Baltimore, MD (US)

(72) Inventors: Wojciech Lesniak, Owings Mills, MD (US); Sridhar Nimmagadda, Baltimore, MD (US); Nikita Oskolkov, Reisterstown, MD (US); Michael McMahon, Columbia, MD (US); Xiaolei Song, Baltimore, MD (US); Martin G. Pomper, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/771,786

(22) PCT Filed: Oct. 27, 2016

(86) PCT No.: PCT/US2016/059046
§ 371 (c)(1),
(2) Date: Apr. 27, 2018

(87) PCT Pub. No.: WO2017/075171
PCT Pub. Date: May 4, 2017

(65) Prior Publication Data
US 2019/0060490 A1 Feb. 28, 2019

Related U.S. Application Data

(60) Provisional application No. 62/246,998, filed on Oct. 27, 2015.

(51) Int. Cl.
| | |
|---|---|
| *A61K 49/12* | (2006.01) |
| *A61K 49/14* | (2006.01) |
| *A61K 49/10* | (2006.01) |
| *A61K 51/04* | (2006.01) |
| *C08G 73/02* | (2006.01) |
| *C08G 83/00* | (2006.01) |
| *C08G 79/08* | (2006.01) |
| *A61K 49/16* | (2006.01) |
| *A61K 51/06* | (2006.01) |

(52) U.S. Cl.
CPC .......... *A61K 49/124* (2013.01); *A61K 49/106* (2013.01); *A61K 49/108* (2013.01); *A61K 49/14* (2013.01); *A61K 49/16* (2013.01); *A61K 51/0482* (2013.01); *A61K 51/065* (2013.01); *C08G 73/028* (2013.01); *C08G 79/08* (2013.01); *C08G 83/00* (2013.01); *C08G 83/003* (2013.01)

(58) Field of Classification Search
CPC ........ A61K 49/10; A61K 49/12; A61K 49/14; A61K 51/04
See application file for complete search history.

(56) References Cited

U.S. PATENT DOCUMENTS

2013/0336888 A1* 12/2013 Babich .................. A61P 35/00
424/1.65

FOREIGN PATENT DOCUMENTS

| WO | WO 2009070302 | 12/2008 |
| WO | WO 2009002529 | 6/2009 |
| WO | WO 2010108125 | 9/2010 |
| WO | WO 2011053615 | 5/2011 |

OTHER PUBLICATIONS

Agrawal et al., Functional delivery of siRNA in mice using dendriworms. ACS Nano. Sep. 22, 2009;3(9):2495-504.
Aime et al., Tunable imaging of cells labeled with MRI-PARACEST agents. Angew Chem Int Ed Engl. Mar. 11, 2005;44(12):1813-5.
Allard et al., Convection-enhanced delivery of nanocarriers for the treatment of brain tumors. Biomaterials. Apr. 2009;30(12):2302-18.
Almutairi et al., Biodegradable dendritic positron-emitting nanoprobes for the noninvasive imaging of angiogenesis. Proc Natl Acad Sci U S A. Jan. 20, 2009;106(3):685-90.
Bar-Shir et al., Human protamine-1 as an MRI reporter gene based on chemical exchange. ACS Chem Biol. Jan. 17, 2014;9(1):134-8.
Bar-Shir et al., Transforming thymidine into a magnetic resonance imaging probe for monitoring gene expression. J Am Chem Soc. Jan. 30, 2013;135(4):1617-24.
Bartolini et al., An investigation of the toxicity of gadolinium based MRI contrast agents using neutron activation analysis. Magn Reson Imaging. Jun. 2003;21(5):541-4.
Bidros et al., Future of convection-enhanced delivery in the treatment of brain tumors. Future Oncol. Jan. 2010;6(1):117-25.
Bobo et al., Convection-enhanced delivery of macromolecules in the brain. Proc Natl Acad Sci U S A. Mar. 15, 1994;91(6):2076-80.
Bochner et al., Salicylate metabolite kinetics after several salicylates. Clin Pharmacol Ther. Aug. 1981;30(2):266-75.
Bryant et al., Synthesis and relaxometry of high-generation (G=5, 7, 9, and 10) PAMAM dendrimer-DOTA-gadolinium chelates. J Magn Reson Imaging. Feb. 1999;9(2):348-52.
Bulte et al., Dysprosium-DOTA-PAMAM dendrimers as macromolecular T2 contrast agents. Preparation and relaxometry. Invest Radiol. Nov. 1998;33(11):841-5.
Caminade et al., Dendrimers for drug delivery. J. Mater. Chem. B 2014;2:4055-66.
Chan et al., A diaCEST MRI approach for monitoring liposomal accumulation in tumors. J Control Release. Apr. 28, 2014;180:51-9.
Chan et al., Diamagnetic chemical exchange saturation transfer (diaCEST) liposomes: physicochemical properties and imaging applications. Wiley Interdiscip Rev Nanomed Nanobiotechnol. Jan.-Feb. 2014;6(1):111-24.

(Continued)

*Primary Examiner* — Michael G. Hartley
*Assistant Examiner* — Jagadishwar R Samala
(74) *Attorney, Agent, or Firm* — Casimir Jones, S.C.; Jeffrey W. Childers

(57) ABSTRACT

PAMAM dendrimer based CEST imaging agents, pharmaceutical compositions comprising the same and methods of uses thereof are disclosed.

37 Claims, 28 Drawing Sheets

(56) References Cited

OTHER PUBLICATIONS

Chan et al., MRI-detectable pH nanosensors incorporated into hydrogels for in vivo sensing of transplanted-cell viability. Nat Mater. Mar. 2013;12(3):268-75.

Chan et al., Natural D-glucose as a biodegradable MRI contrast agent for detecting cancer. Magn Reson Med. Dec. 2012;68(6):1764-73.

Chen et al., Evaluations of extracellular pH within in vivo tumors using acidoCEST MRI. Magn Reson Med. Nov. 2014;72(5):1408-17.

Esfand et al., Poly(amidoamine) (PAMAM) dendrimers: from biomimicry to drug delivery and biomedical applications. Drug Discov Today. Apr. 1, 2001;6(8):427-436.

Farrar et al., Establishing the Lysine-rich Protein CEST Reporter Gene as a CEST MR Imaging Detector for Oncolytic Virotherapy. Radiology. Jun. 2015;275(3):746-54.

Huang et al., Biodegradable polydisulfide dendrimer nanoclusters as MRI contrast agents. ACS Nano. Nov. 27, 2012;6(11):9416-24.

Hyman et al., Probing oxidative stress: Small molecule fluorescent sensors of metal ions, reactive oxygen species, and thiols. Coord Chem Rev. Oct. 1, 2012;256(19-20):2333-2356.

Kannan et al., Emerging concepts in dendrimer-based nanomedicine: from design principles to clinical applications. J Intern Med. Dec. 2014;276(6):579-617.

Kobayashi et al., Multimodal nanoprobes for radionuclide and five-color near-infrared optical lymphatic imaging. ACS Nano. Nov. 2007;1(4):258-64.

Kobayashi et al., Nano-sized MRI contrast agents with dendrimer cores. Adv Drug Deliv Rev. Dec. 14, 2005;57(15):2271-86.

Kogan et al., Imaging of glutamate in the spinal cord using GluCEST. Neuroimage. Aug. 15, 2013;77:262-7.

Lesniak et al., Salicylic Acid Conjugated Dendrimers Are a Tunable, High Performance CEST MRI NanoPlatform. Nano Lett. Apr. 13, 2016;16(4):2248-53.

Ling et al., Assessment of glycosaminoglycan concentration in vivo by chemical exchange-dependent saturation transfer (gagCEST). Proc Natl Acad Sci U S A. Feb. 19, 2008;105(7):2266-70.

Liu et al., High-Throughput Screening of Chemical Exchange Saturation Transfer MR Contrast Agents. Con. Media. & Mol. Imag. 2010; 5(3):162-170.

Liu et al., In Vivo Multi-Color Molecular MR Imaging Using DIACEST Liposomes. Magn Reson Med. Apr. 2012; 67(4):1106-1113.

Liu et al., Nuts and bolts of chemical exchange saturation transfer MRI. NMR Biomed. Jul. 2013;26(7):810-28.

Longo et al., Imaging the pH evolution of an acute kidney injury model by means of iopamidol, a MRI-CEST pH-responsive contrast agent. Magn Reson Med. Sep. 2013;70(3):859-64.

Longo et al., Iopamidol as a responsive MRI-chemical exchange saturation transfer contrast agent for pH mapping of kidneys: In vivo studies in mice at 7 T. Magn Reson Med. Jan. 2011;65(1):202-11.

Lonser et al., Successful and safe perfusion of the primate brainstem: in vivo magnetic resonance imaging of macromolecular distribution during infusion. J Neurosurg. Oct. 2002;97(4):905-13.

McMahon et al., New "multicolor" polypeptide diamagnetic chemical exchange saturation transfer (DIACEST) contrast agents for MRI. Magn Reson Med. Oct. 2008;60(4):803-12.

McMahon et al., Quantifying exchange rates in chemical exchange saturation transfer agents using the saturation time and saturation power dependencies of the magnetization transfer effect on the magnetic resonance imaging signal (QUEST and QUESP): Ph calibration for poly-L-lysine and a starburst dendrimer. Magn Reson Med. Apr. 2006;55(4):836-47.

Menjoge et al.,Dendrimer-based drug and imaging conjugates: design considerations for nanomedical applications. Drug Discov Today. Mar. 2010;15(5-6):171-85.

Misselwitz et al., Pharmacokinetics of Gadomer-17, a new dendritic magnetic resonance contrast agent. MAGMA. May 2001;12(2-3):128-34.

Molday et al., Primary structure effects on peptide group hydrogen exchange. Biochemistry 1972; 11:150-158.

Needs et al., Clinical pharmacokinetics of the salicylates. Clin Pharmacokinet. Mar.-Apr. 1985;10(2):164-77.

Opina et al., Preparation and long-term biodistribution studies of a PAMAM dendrimer G5-Gd-BnDOTA conjugate for lymphatic imaging. Nanomedicine (Lond). May 2015;10(9):1423-37.

Paterson et al., Salicylic acid sans aspirin in animals and man: persistence in fasting and biosynthesis from benzoic acid. J Agric Food Chem. Dec. 24, 2008;56(24):11648-52.

Que et al., Responsive magnetic resonance imaging contrast agents as chemical sensors for metals in biology and medicine. Chem Soc Rev. Jan. 2010;39(1):51-60.

Rivlin et al., Mapping brain glucose uptake with chemical exchange-sensitive spin-lock magnetic resonance imaging. J Cereb Blood Flow Metab. Aug. 2014;34(8):1402-10.

Shaw et al., Radiation Therapy Oncology Group: radiosurgery quality assurance guidelines. nt J Radiat Oncol Biol Phys. Dec. 1, 1993;27(5):1231-9.

Sherry et al., Chemical exchange saturation transfer contrast agents for magnetic resonance imaging. Annu Rev Biomed Eng. 2008;10:391-411.

Somani et al., Applications of dendrimers for brain delivery and cancer therapy. Nanomedicine (Lond). Oct. 2014;9(15):2403-14.

Song et al., Label-free in vivo molecular imaging of underglycosylated mucin-1 expression in tumour cells. Nat Commun. Mar. 27, 2015;6:6719.

Stroom et al., Inclusion of geometrical uncertainties in radiotherapy treatment planning by means of coverage probability. Int J Radiation Oncol. Mar. 1999;43(4):905-19.

Sun et al., Investigation of optimizing and translating pH-sensitive pulsed-chemical exchange saturation transfer (CEST) imaging to a 3T clinical scanner. Magn Reson Med. Oct. 2008;60(4):834-41.

Thomas et al., Emerging therapies for glioblastoma. JAMA Neurol. Nov. 2014;71(11):1437-44.

Toth et al., The Role of Water Exchange in Attaining Maximum Relaxivities for Dendrimeric MRI Contrast Agents. Chem.-Eur. 1996;2:1607-1615.

Van Zijl et al., Chemical exchange saturation transfer (CEST): what is in a name and what isn't? Magn Reson Med 2011;65(4):927-948.

Van Zijl et al., MRI detection of glycogen in vivo by using chemical exchange saturation transfer imaging (glycoCEST). Proc Natl Acad Sci U S A. Mar. 13, 2007;104(11):4359-64.

Villaraza et al., Macromolecules, dendrimers, and nanomaterials in magnetic resonance imaging: the interplay between size, function, and pharmacokinetics. Chem Rev. May 12, 2010;110(5):2921-59.

Walker-Samuel et al., In vivo imaging of glucose uptake and metabolism in tumors. Nat Med. Aug. 2013;19(8):1067-72.

Wang et al., A novel Affibody bioconjugate for dual-modality imaging of ovarian cancer. Chem Commun (Camb). Nov. 4, 2014;50(85):12832-5.

Wiener et al., Dendrimer-based metal chelates: a new class of magnetic resonance imaging contrast agents. Magn Reson Med. Jan. 1994;31(1):1-8.

Woodworth et al., Emerging insights into barriers to effective brain tumor therapeutics. Front Oncol. Jul. 21, 2014;4:126.

Yang et al., Convection enhanced delivery of boronated EGF as a molecular targeting agent for neutron capture therapy of brain tumors. J Neurooncol. Dec. 2009;95(3):355-365.

Yang et al., Molecular targeting and treatment of composite EGFR and EGFRvIII-positive gliomas using boronated monoclonal antibodies. Clin Cancer Res. Feb. 1, 2008;14(3):883-91.

Yang et al., Salicylic acid and analogues as diaCEST MRI contrast agents with highly shifted exchangeable proton frequencies. Angew Chem Int Ed Engl. Jul. 29, 2013;52(31):8116-9.

Yang et al., Tuning phenols with Intra-Molecular bond Shifted HYdrogens (IM-SHY) as diaCEST MRI contrast agents. Chemistry. Nov. 24, 2014;20(48):15824-32.

Yue et al., Synthesis and characterization of G5 PAMAM dendrimer containing daunorubicin for targeting cancer cells. Arch Pharm Res. Feb. 2012;35(2):343-9.

(56) References Cited

OTHER PUBLICATIONS

Zhang et al., Radiosynthesis and micro-SPECT imaging of 99mTc-dendrimer poly(amido)-amine folic acid conjugate. Bioorg Med Chem Lett. Feb. 1, 2010;20(3):927-31.
Zhong et al., Long-term outcomes of surgical treatment for pulmonary carcinoid tumors: 20 years' experience with 131 patients. Chin Med J (Engl). Sep. 2012;125(17):3022-6.
Zhou et al., Amide proton transfer (APT) contrast for imaging of brain tumors. Magn Reson Med. Dec. 2003;50(6):1120-6.
Zhou et al., Novel delivery strategies for glioblastoma. Cancer J. Jan.-Feb. 2012;18(1):89-99.
International Search Report and Written Opinion for PCT/US16/59046, dated Jun. 1, 2017, 15 pages.

* cited by examiner

11PAMAM DENDRIMER BASED CEST IMAGING AGENTS AND USES THEREOF

CROSS-REFERENCE TO RELATED APPLICATIONS

This application is a 35 U.S.C. § 371 National Stage Entry of International Application No. PCT/US2016/059046 having an international filing date of Oct. 27, 2016, which claims the benefit of U.S. Provisional Application No. 62/246,998, filed Oct. 27, 2015, the contents of which are incorporated herein by reference in their entirety.

FEDERALLY SPONSORED RESEARCH OR DEVELOPMENT

This invention was made with government support under EB015031 and CA166131, awarded by the National Institutes of Health. The government has certain rights in the invention.

BACKGROUND

CEST imaging is rapidly emerging as a novel magnetic resonance imaging (MRI) contrast mechanism that is useful for molecular imaging (McMahon et al., 2008; Chan et al., 2014; Liu et al., 2012). CEST possesses several benefits compared to other MRI contrast mechanisms. Frequency specific switchable contrast could be achieved by CEST (turned 'on' through application of saturation pulse) thus detection of multiple agents independently in a single image is possible similar to that achieved with optical imaging agents (McMahon et al., 2008; Aime et al., 2005). Because of its reliance on exchangeable protons, CEST can be applied for detecting organic compounds and probe biochemical pathways based on biomolecule's inherent CEST properties (Bartolibi et al., 2003). Several examples of this include glucose (Walker-Samuel et al., 2013; Chan et al., 2012; Rivlin et al., 2014; Jin et al., 2014), glycogen (van Zijl et al., 2007), glutamate (Kogen et al., 2013), L-arginine (Chan et al., 2013), creatine (Kogan et al., 2013; Sum et al., 2008), barbituric acid (Chan et al., 2014), a number of thymidine analogs ((Bar-Shir et al., *JACS* 2013), iopamidol (Longo et al., 2013), iopromide (Chen et al., 2014), glycosaminoglycans (Ling et al., 2008), and proteins such as the lysine rich protein, human protamine and others (Bar-Shir et al., *Chem. Biology* 2013; Farrar et al., 2015; Gilad et al., 2007; Zhou et al., 2003). Many existing CEST imaging agents exhibit low sensitivity caused by an insignificant difference in chemical shift for their exchangeable protons with water and high concentration metabolites. As a solution, salicylic acid (SA), anthranillic acid and number of their derivatives as organic, diamagnetic CEST agents with highly shifted exchangeable protons (between 5 and 12 part-per-million (ppm) from water), which present sensitivity advantages for 3T clinical scanners (Yang et al., 2013; Yang et al., 2014; Song et al., 2015) have been reported. The goal of these studies was to translate these probes for monitoring nanocarrier delivery.

Brain tumors, particularly glioblastoma multiforme, have poor survival rates even with use of the most aggressive therapies (Thomas et al., 2014). Therapeutic options for brain tumors are limited by insufficient delivery of systemically administered agents to tumor (Woodworth et al., 2014). Convection enhanced delivery (CED) is gaining attention as a local therapeutic delivery option for nanocarriers, particularly for brain tumors due to the possibility of a prolonged, high payload delivery (Volgerlbaum et al., 2015). Though macro distribution (accumulation, retention and clearance) properties of nanoparticles within brain tumors can be quantified using PET and optical imaging techniques non-invasively, their micro distribution (rate and extent of distribution within the tumor) within the tumors is difficult to monitor using these imaging techniques due to poor spatial resolution and depth penetration, respectively. Therefore, a need remains for the design and development of CEST MR contrast agents that offer enhanced and persistent contrast for imaging and therapy.

SUMMARY

In some aspects, the presently disclosed subject matter provides a polyamidoamine (PAMAM) dendrimer of formula (I):

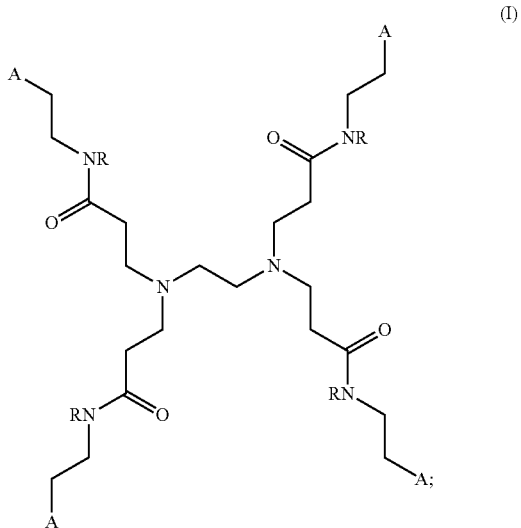

wherein: each A is independently selected from the group consisting of:

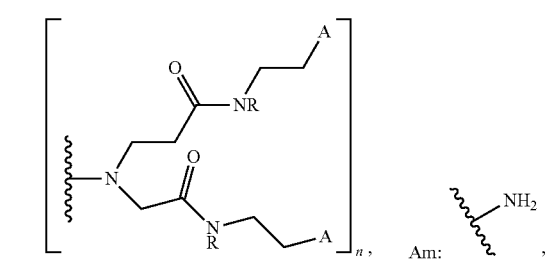

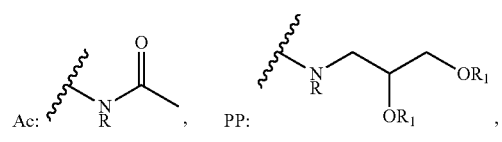

D: a metal chelating moiety optionally comprising a radiometal suitable for treating or imaging, T: a therapeutic agent, TG: a targeting agent, IM: an imaging agent, PEG-X: a polyethylene glycol residue, wherein X is

or TG, and —NR-L-W—(CH$_2$)$_m$-SA;

L is a linking group selected from the group consisting of —(CH$_2$)$_m$—, —C(=O)—(CH$_2$)$_m$—, —(CH$_2$—CH$_2$—O)$_t$—, —C(=O)—(CH$_2$—CH$_2$—O)$_t$—, —(O—CH$_2$—CH$_2$)$_t$—, —C(=O)—(O—CH$_2$—CH$_2$)$_t$—, —C(=O)—(CHR$_2$)$_m$—NR$_3$—C(=O)—(CH$_2$)$_m$—, —C(=O)—(CH$_2$)$_m$—O—C(=O)—NR$_3$—(CH$_2$)$_p$—, —C(=O)—(CH$_2$)$_m$—NR$_3$—C(=O)—O—(CH$_2$)$_p$—, —C(=O)—(CH$_2$)$_m$—NR$_3$—C(=O)—NR$_3$—(CH$_2$)$_p$—, —C(=O)—(CH$_2$)$_m$—NR$_3$—C(=O)—(CH$_2$)$_p$—, —C(=O)—(CH$_2$)$_m$—C(=O)—NR$_3$—(CH$_2$)$_p$—, —C(=O)—(CH$_2$)$_m$—NR$_3$—C(=O)—NR$_3$—(CH$_2$)$_p$—, —C(=O)—(CH$_2$)$_m$—NR$_1$—C(=O)—NR$_3$—(CH$_2$)$_p$—, —C(=O)—(CH$_2$)$_m$—O—C(=O)—NR$_3$—, —C(=O)—CH$_2$)$_m$—O—C(=O)—NR$_3$—(CH$_2$)$_p$—, —C(=O)—(CH$_2$)$_m$—NR$_3$—C(=O)—O—(CH$_2$)$_p$—, polyethylene glycol, glutaric anhydride, albumin, lysine, and amino-acid: W is selected from the group consisting of —NR—C(=O)—, —C(=O)—NR—, —S—, —O—, and —SO$_2$—; SA is

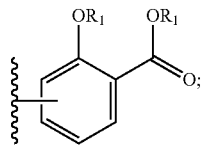

each R is independently selected from the group consisting of H and C$_1$-C$_4$ alkyl; each R$_1$ is independently selected from the group consisting of H, Na, C$_1$-C$_4$ alkyl, and a protecting group; each R$_2$ is independently selected from the group consisting of hydrogen, and —COOR$_1$, each R$_3$ is independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl; m and p are each independently an integer selected from the group consisting of 0, 1, 2, 3, 4, 5, 6, 7 and 8; t is a integer selected from the group consisting of 1, 2, 3, 4, 5, 6, 7, 8, 9, 10, 11 and 12; n is an integer selected from the group consisting of 1, 2, 3, 4, 5, 6, 7, 8, 9, and 10; or a salt or a stereoisomer thereof.

In other aspects, the presently disclosed subject matter provides pharmaceutical compositions comprising a compound of formula (I), and a pharmaceutically acceptable carrier, diluent or excipient.

In further aspects, the presently disclosed subject matter a method for producing a magnetic resonance imaging (MRI) of a target, comprising: contacting the target with an effective amount of a magnetic resonance imaging contrast agent; and imaging the target using a Chemical Exchange Saturation Transfer (CEST) or frequency labeled exchange (FLEX) based MRI technique to produce the MR image of the target, wherein the MRI contrast agent is a dendrimer of formula (I), or a salt or stereoisomer thereof.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1A:
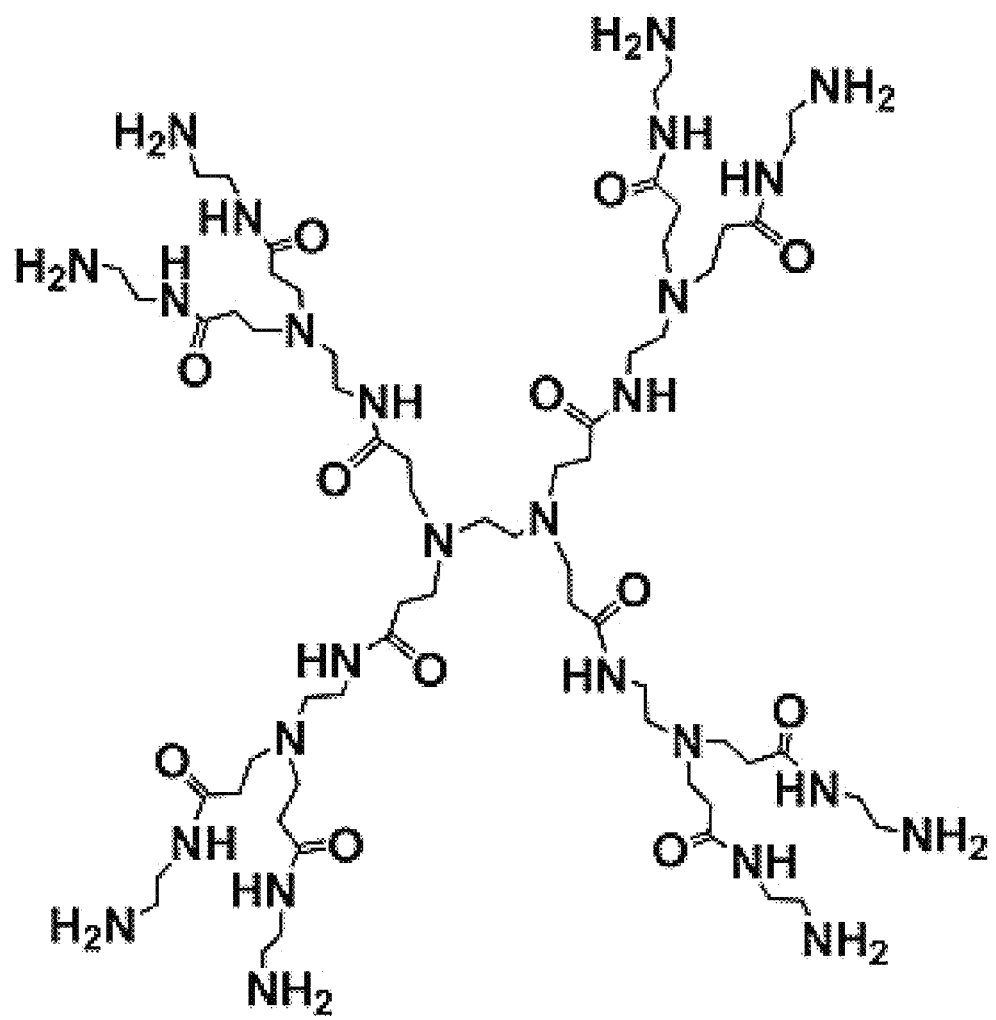
Figure 1B:
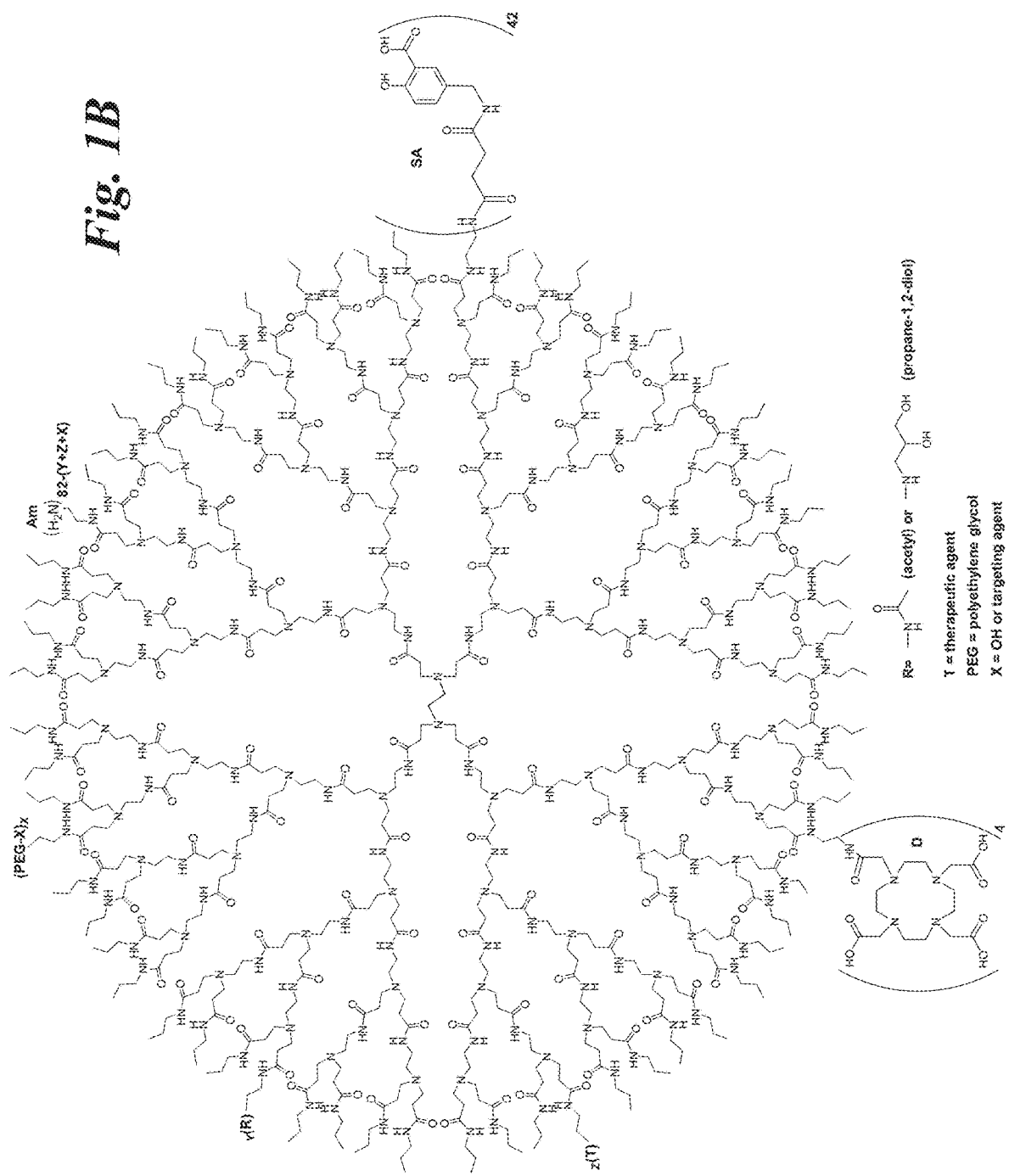
Figure 2:
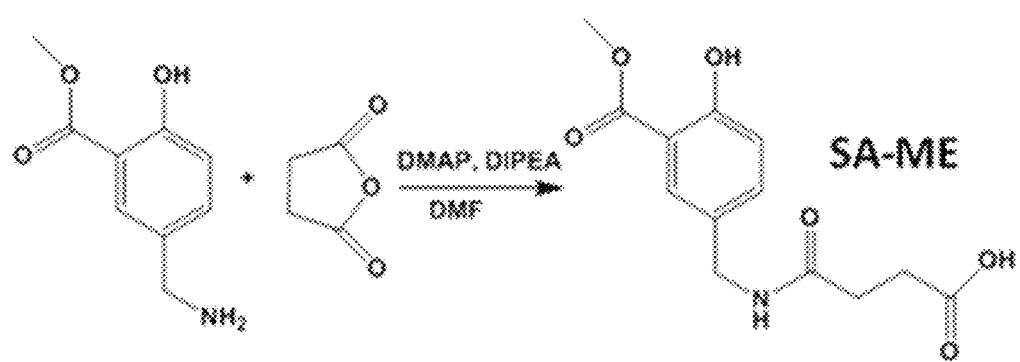
Figure 3A:
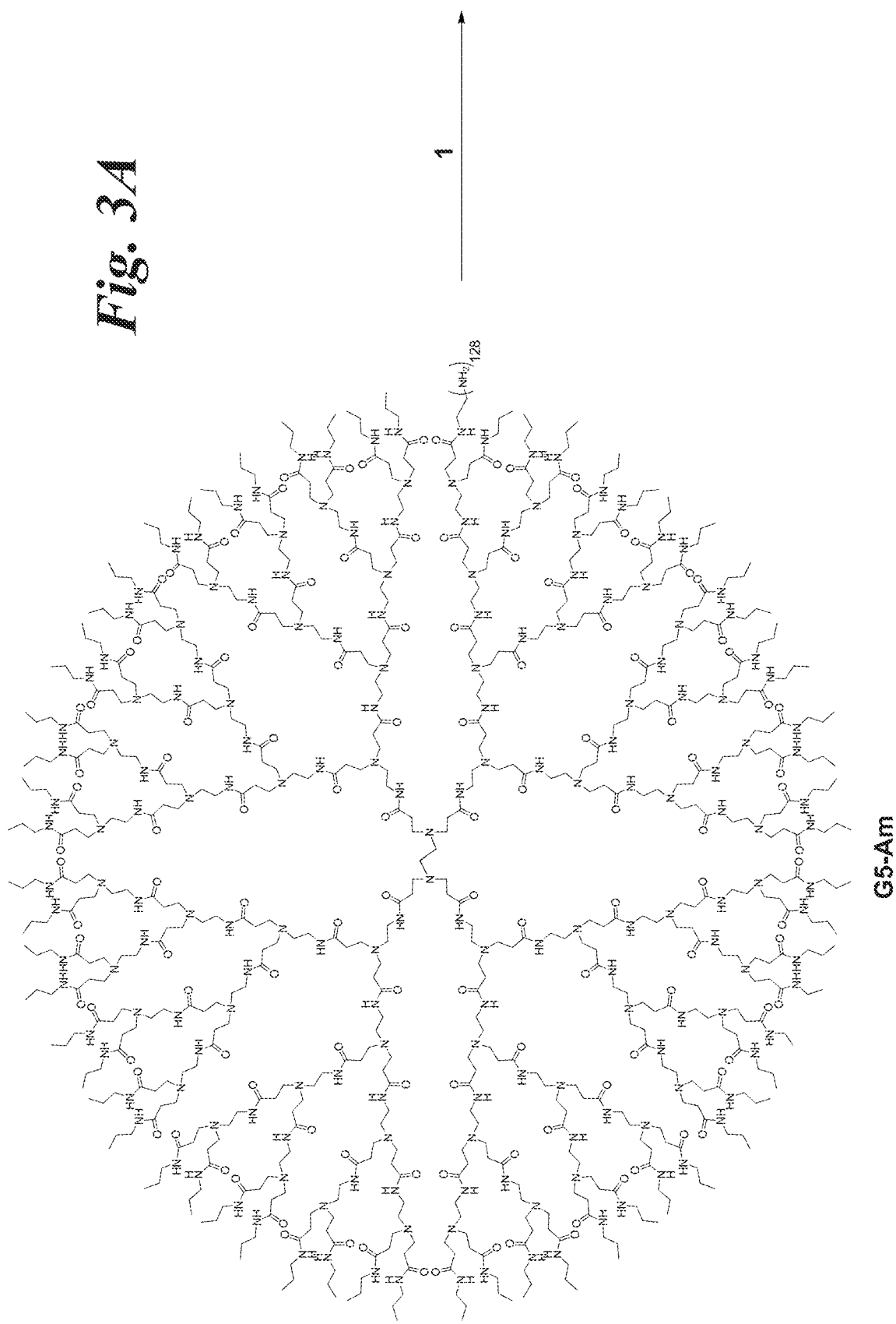
Figure 3B:
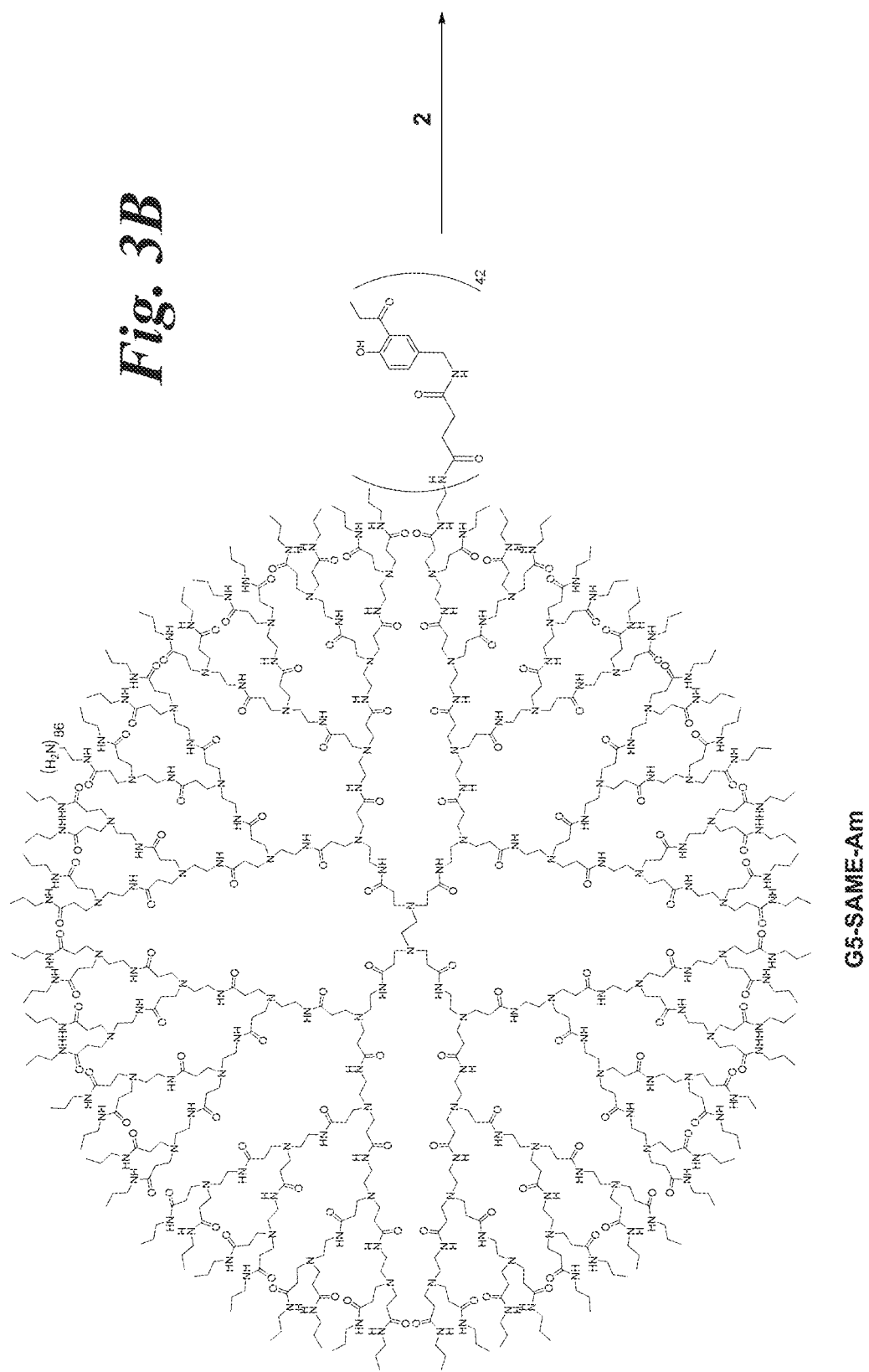
Figure 3C:
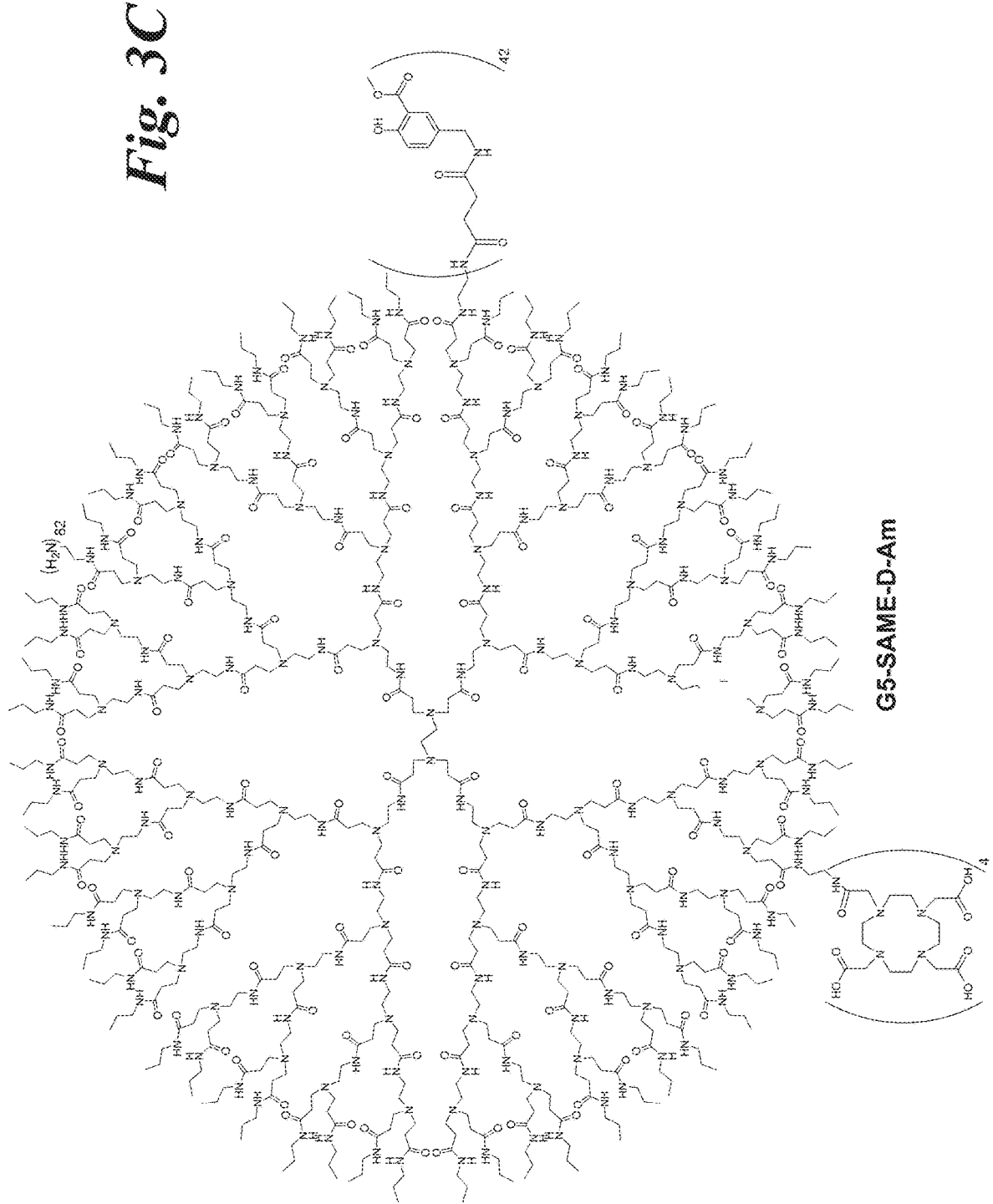
Figure 3D:
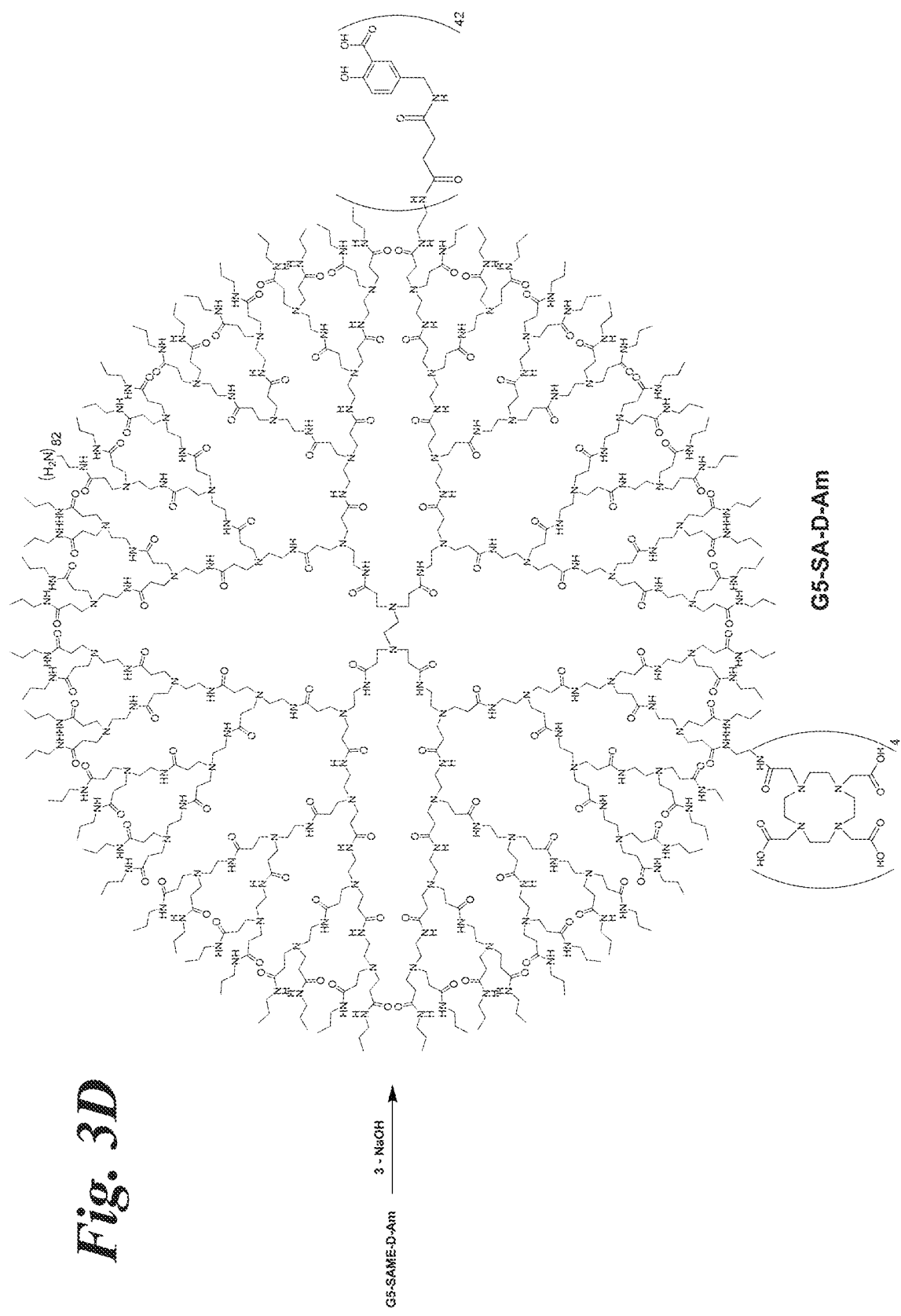
Figure 3E:
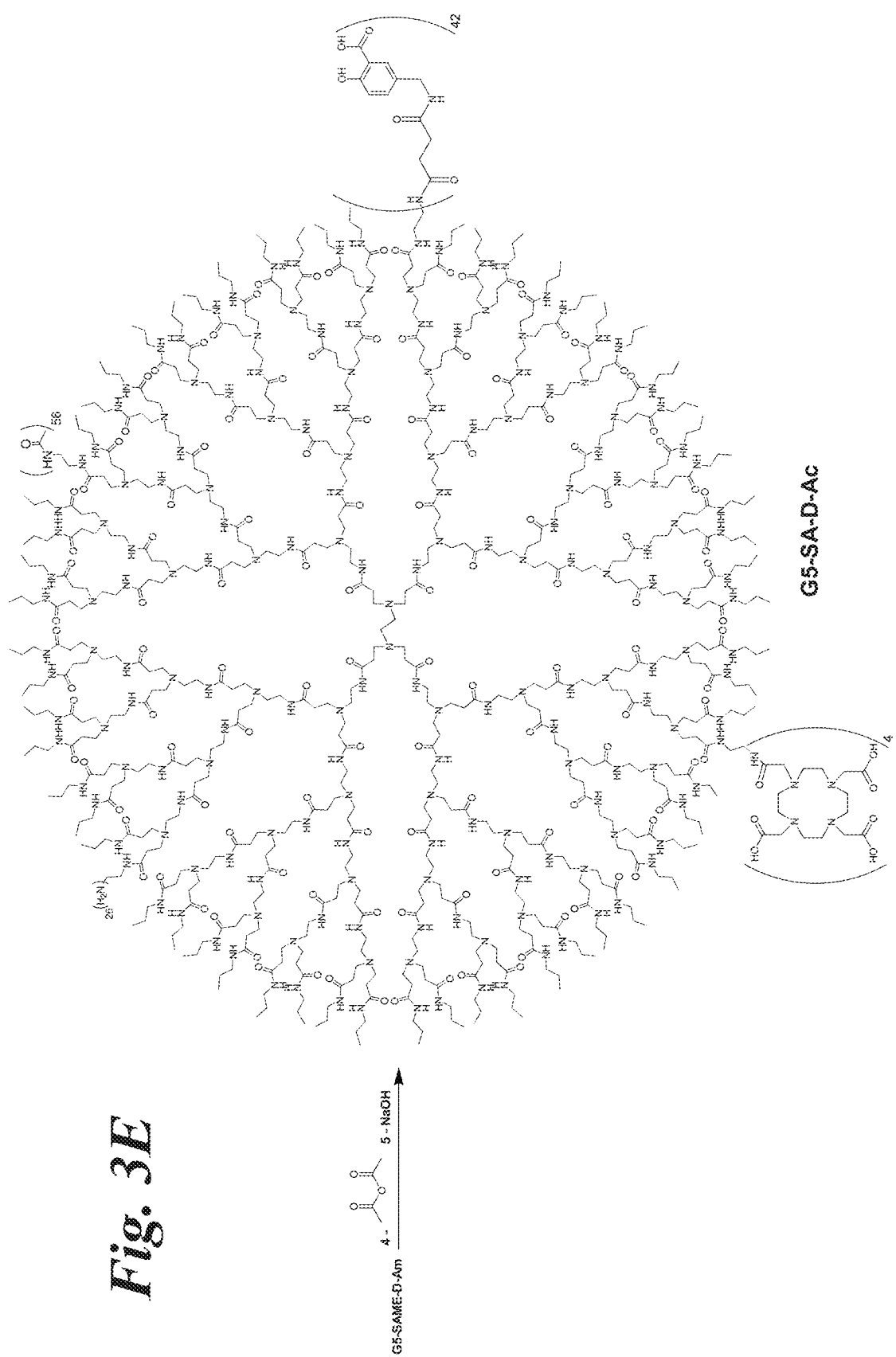
Figure 3F:
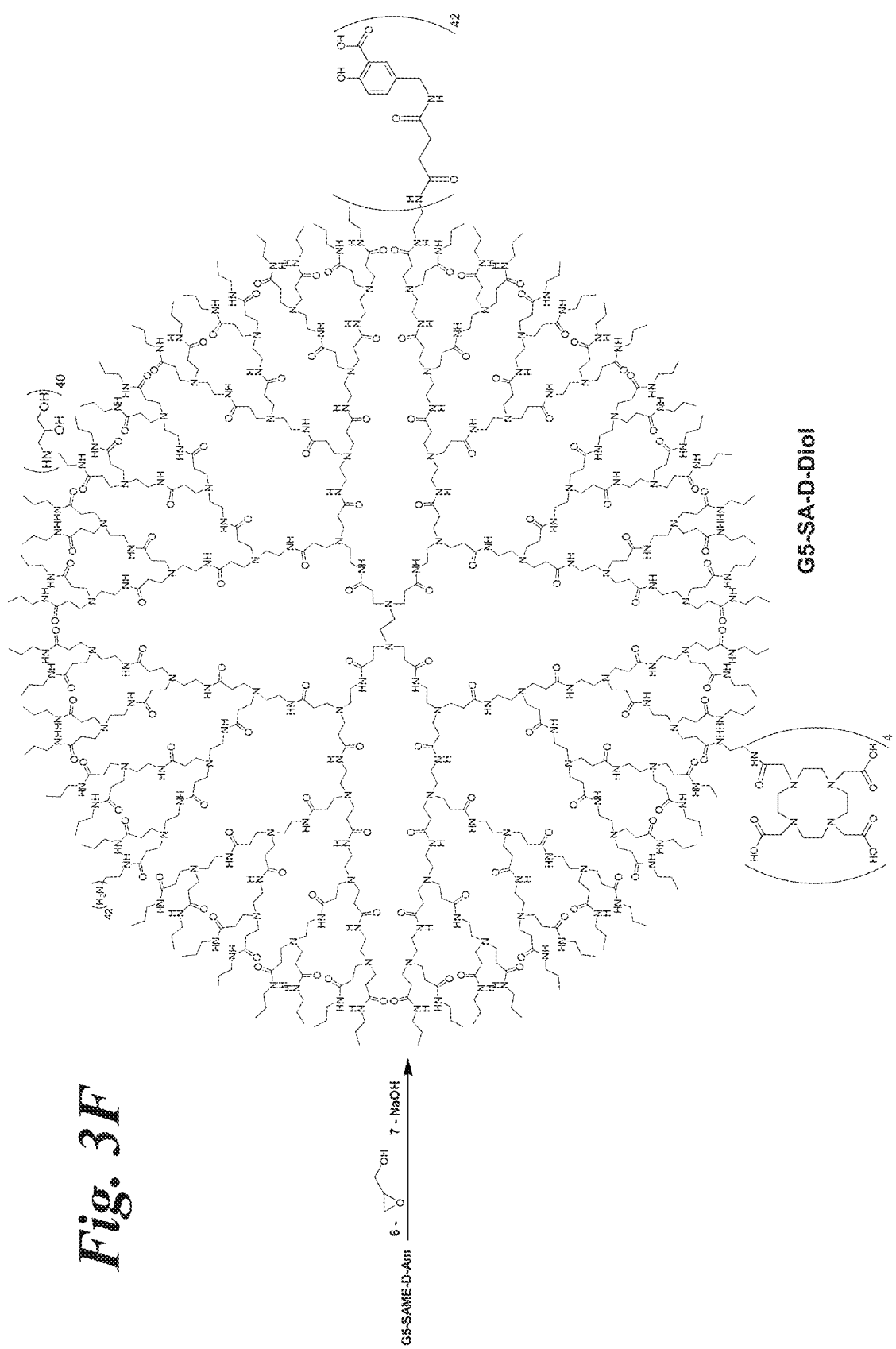
Figure 4:
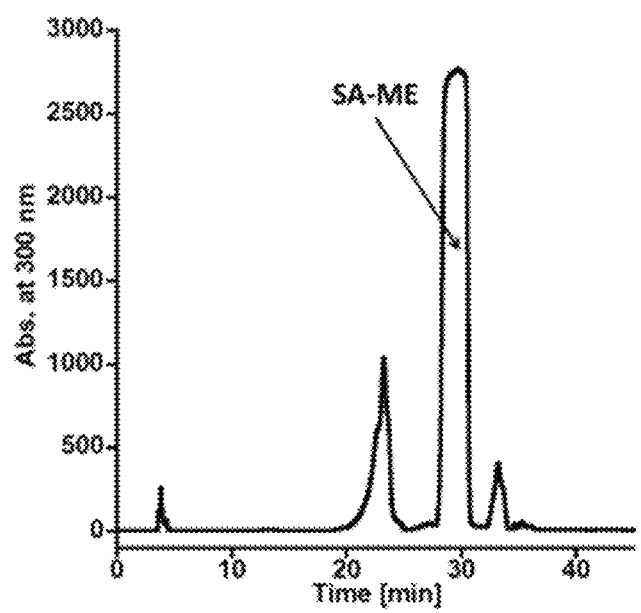
Figure 5:
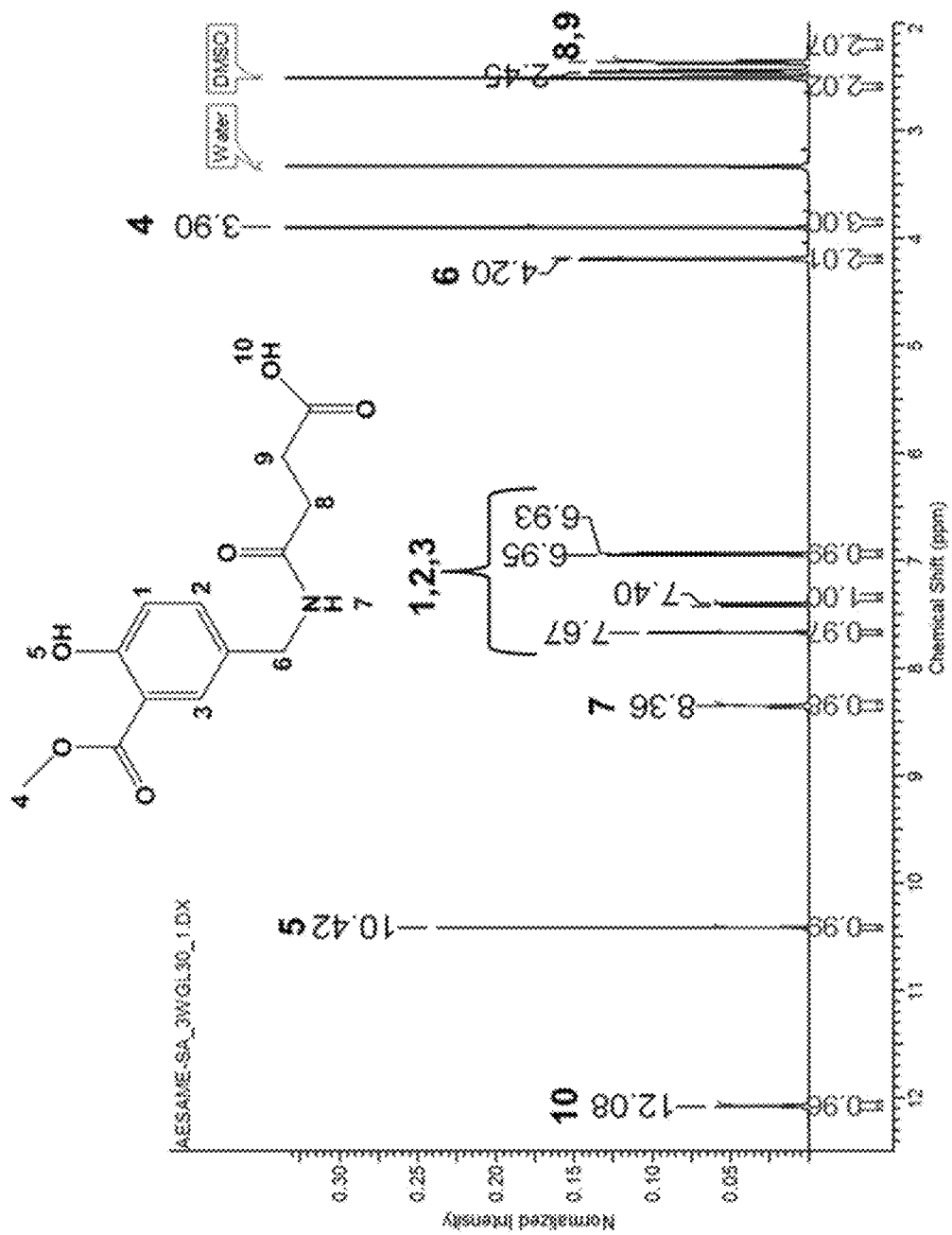
Figure 6:
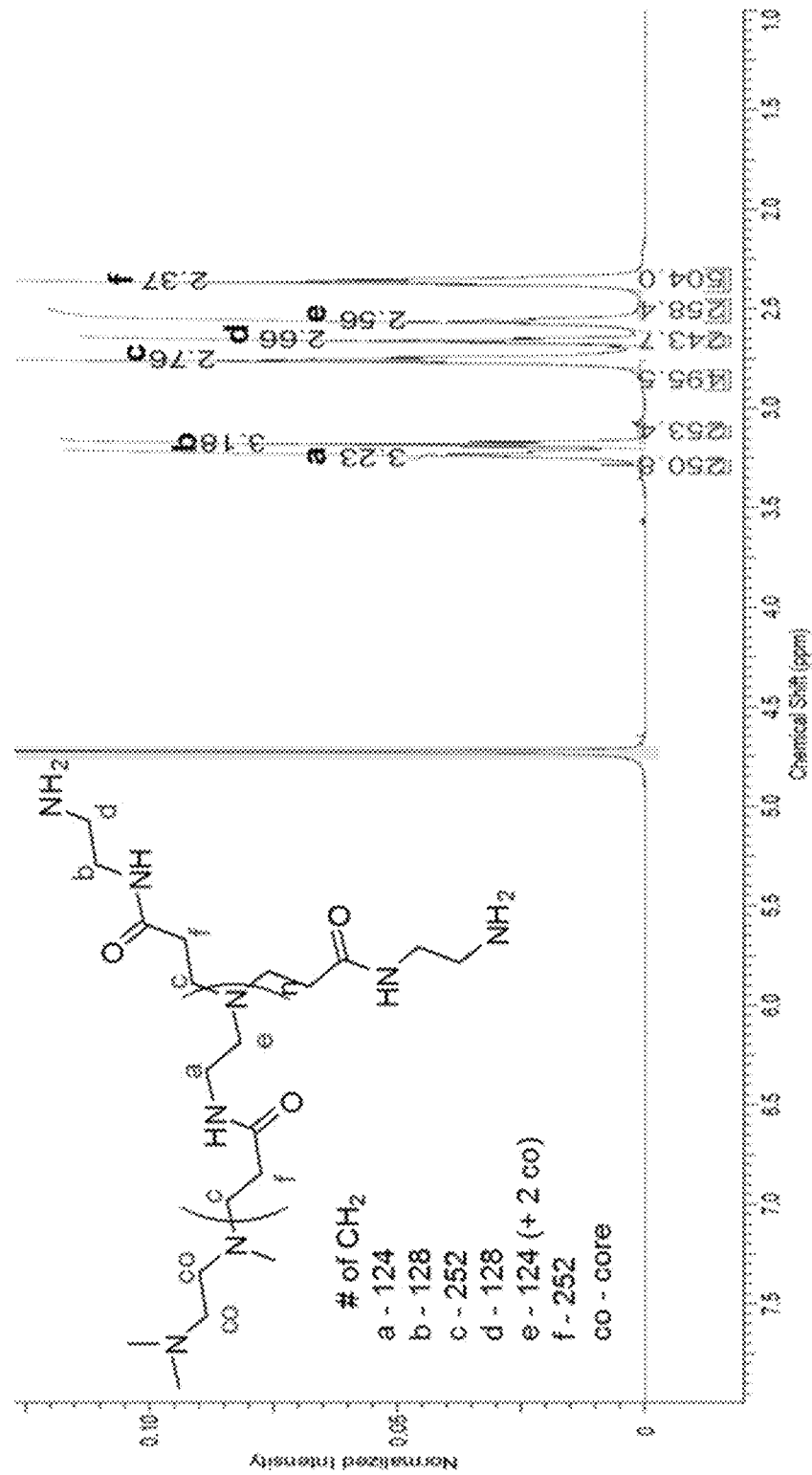
Figure 7:
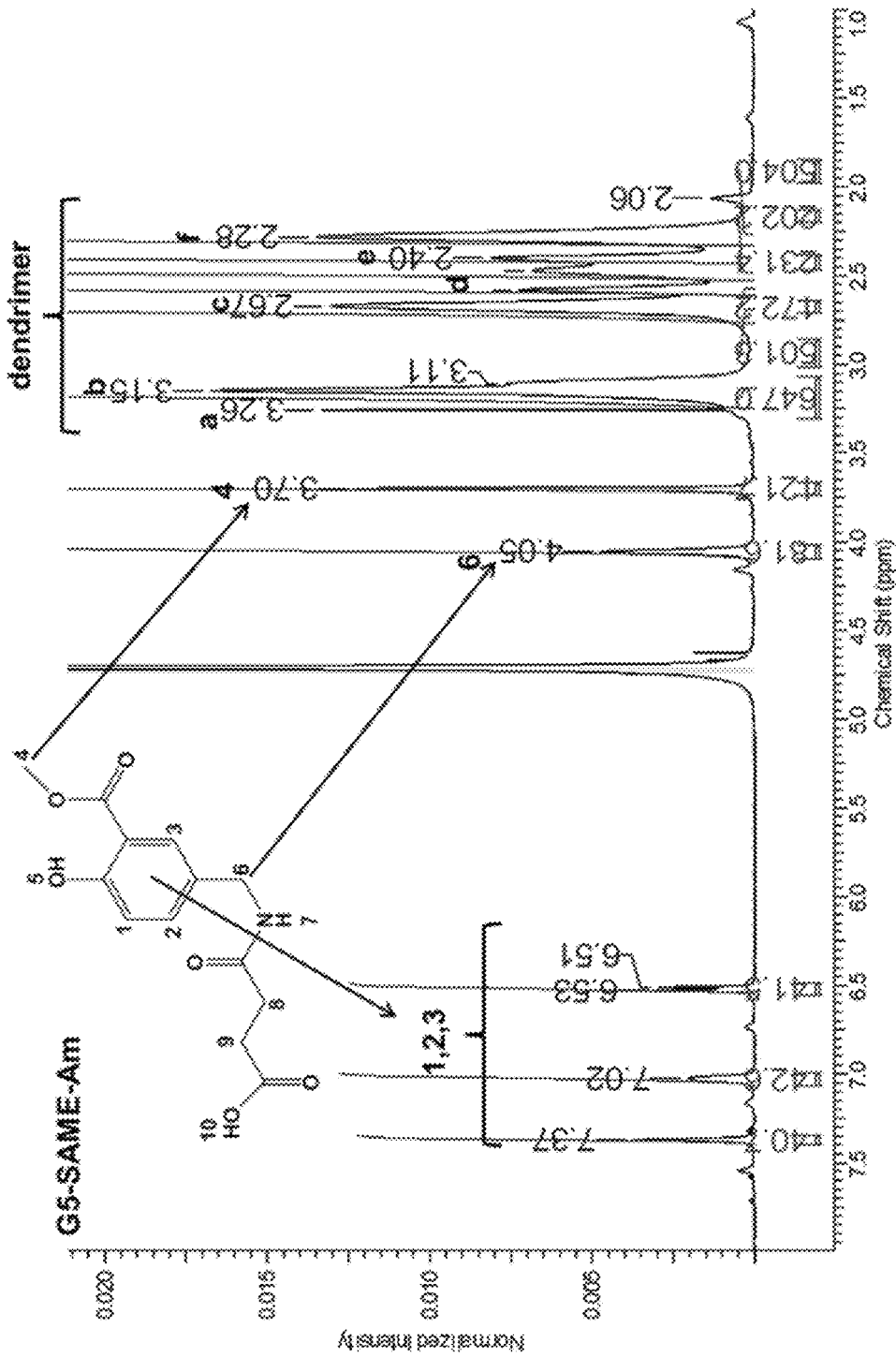
Figure 8:
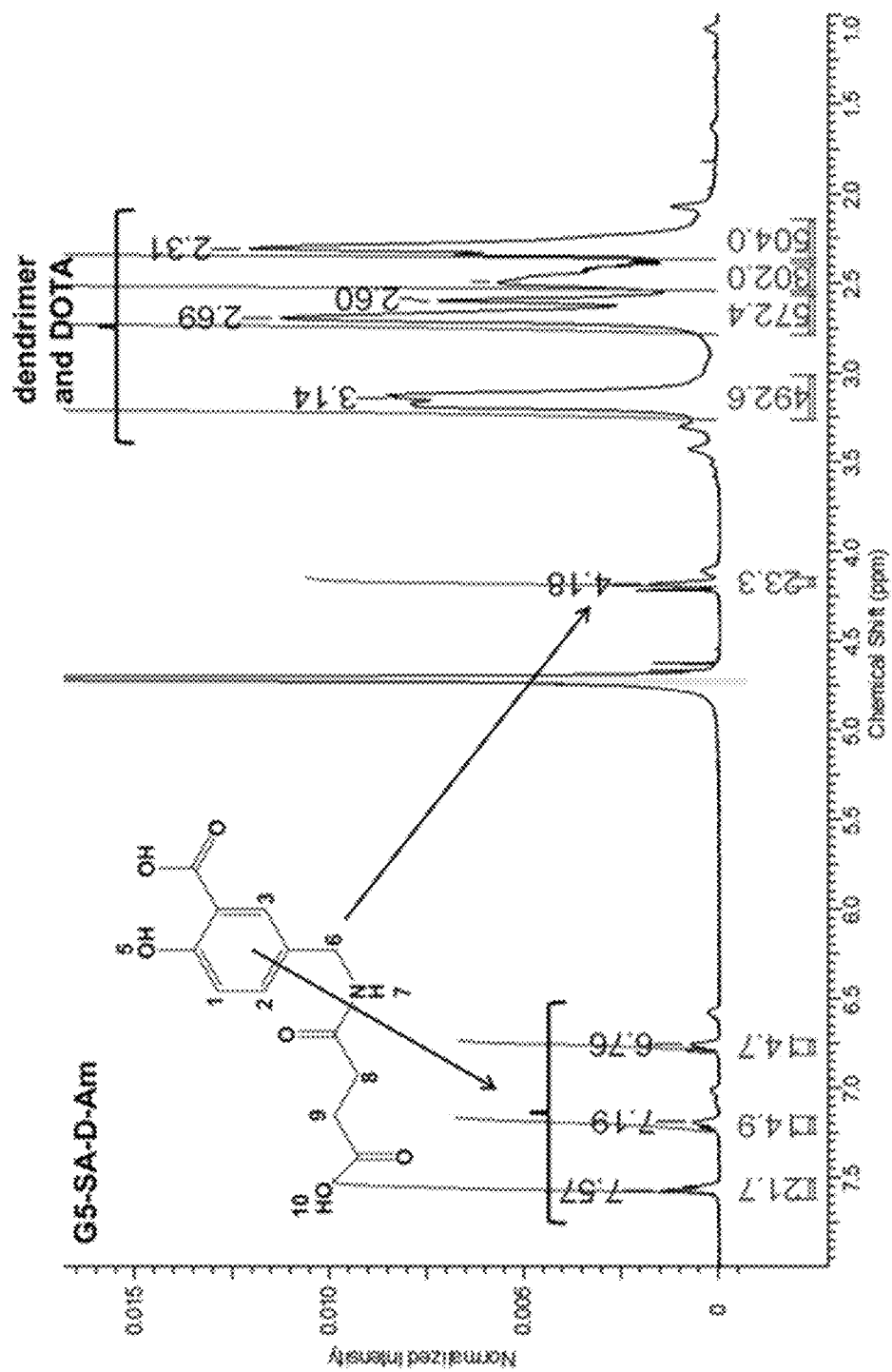
Figure 9:
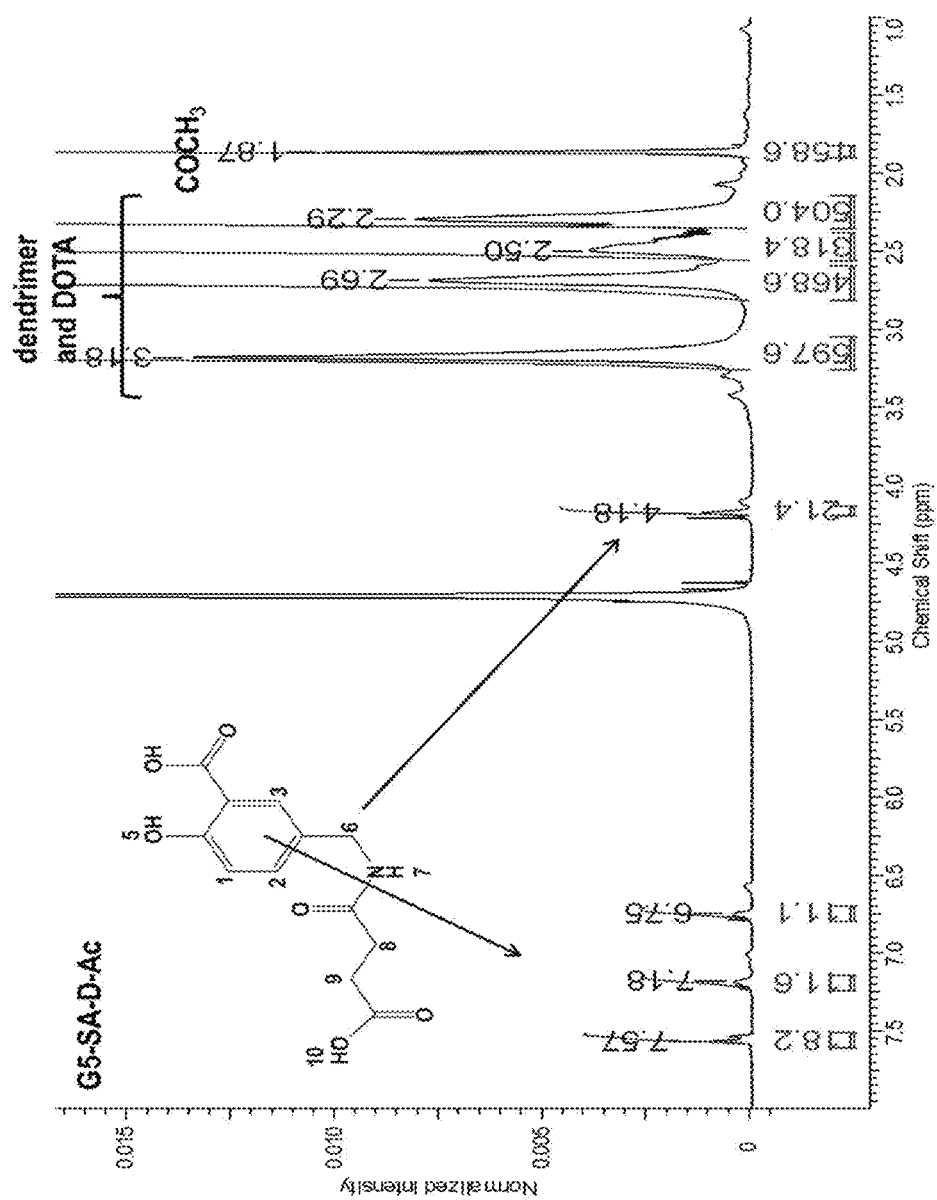
Figure 10:
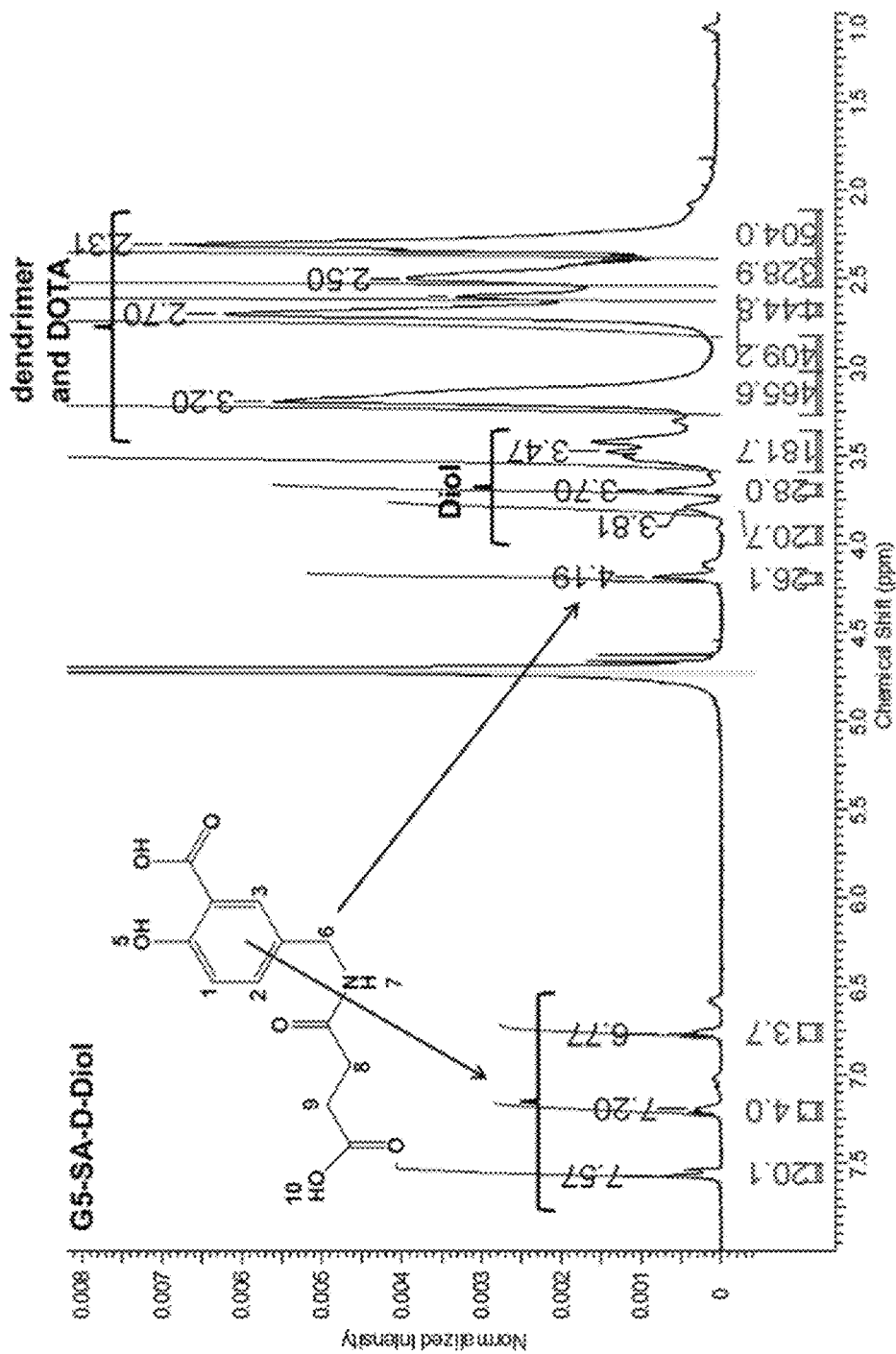
Figure 11:
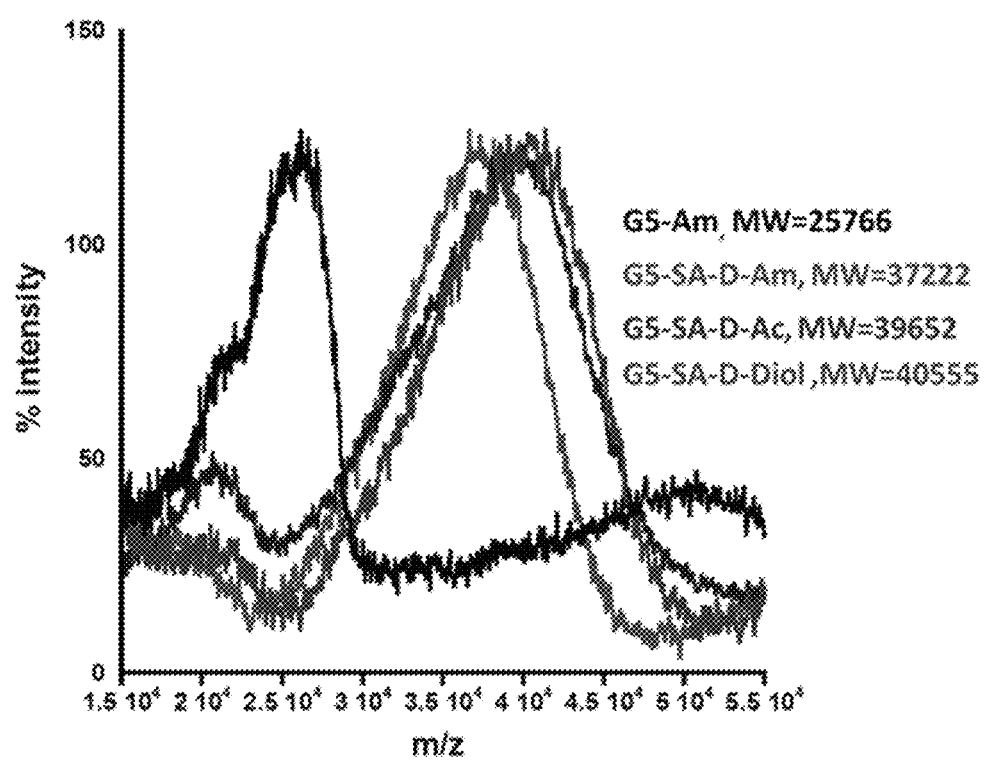
Figure 12:
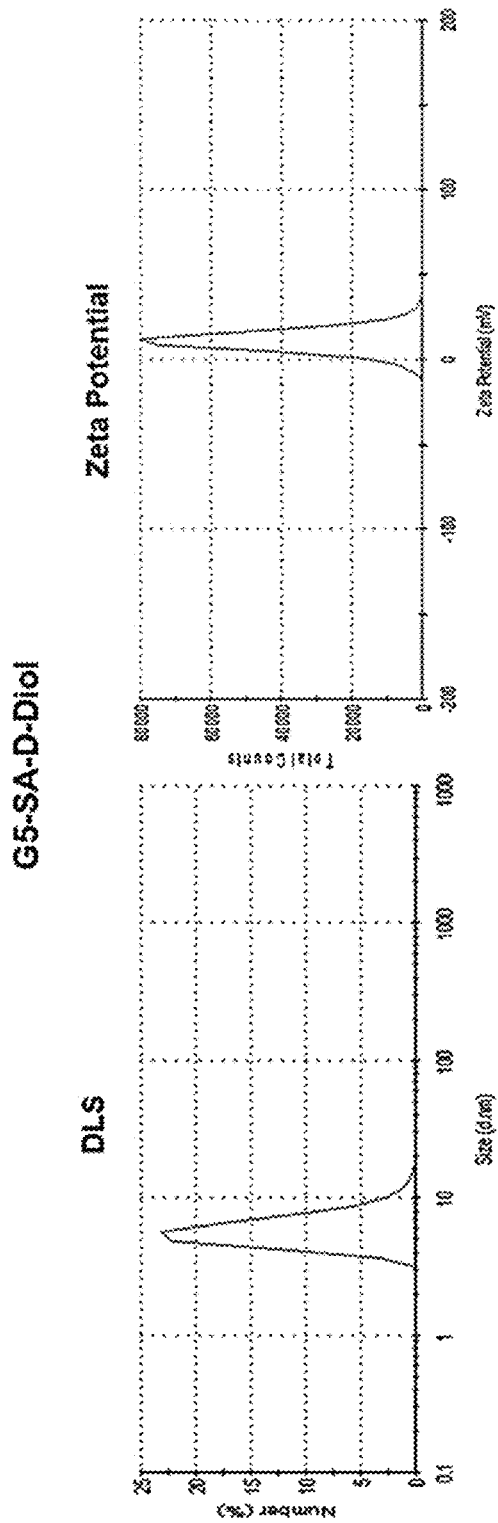
Figure 13A:
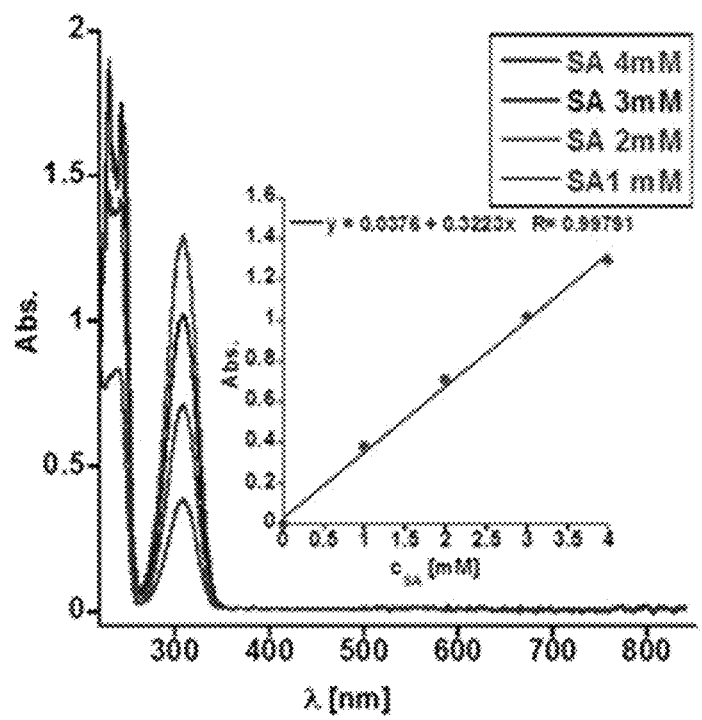
Figure 13B:
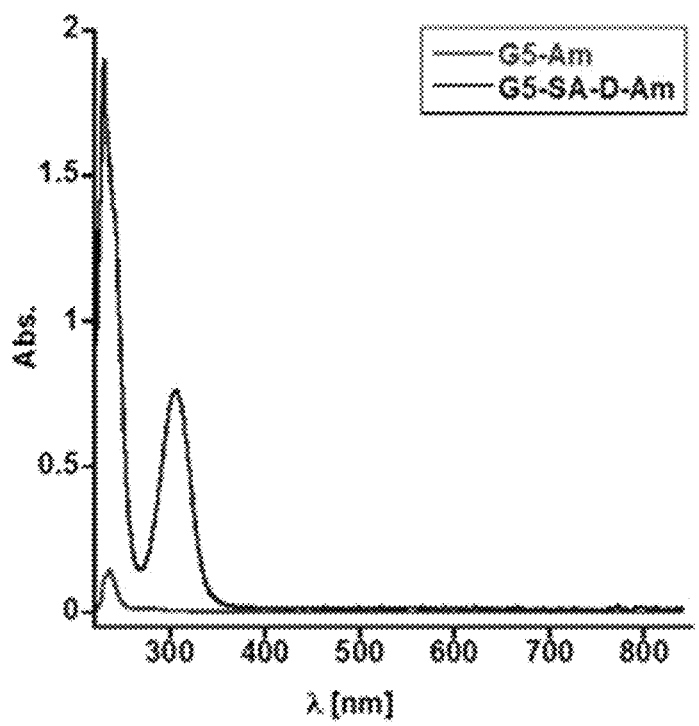
Figure 13C:
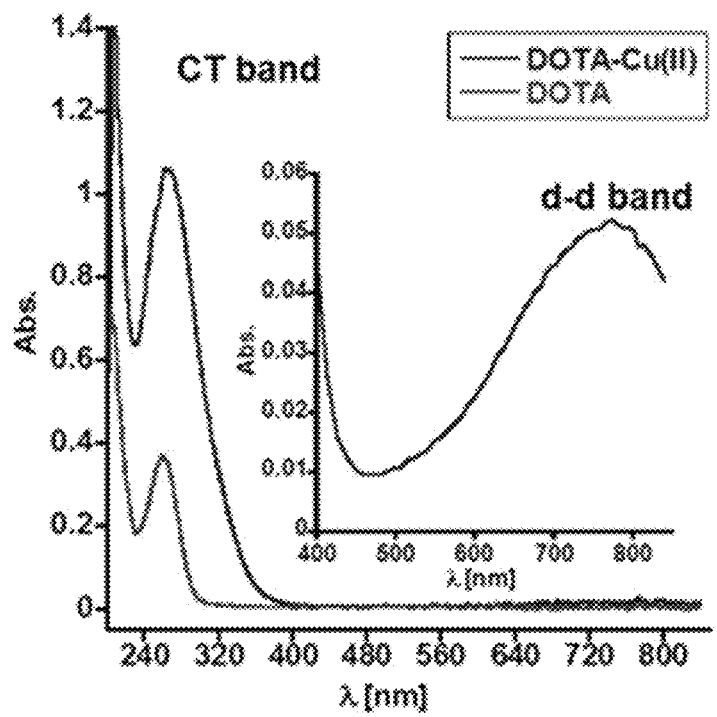
Figure 13D:
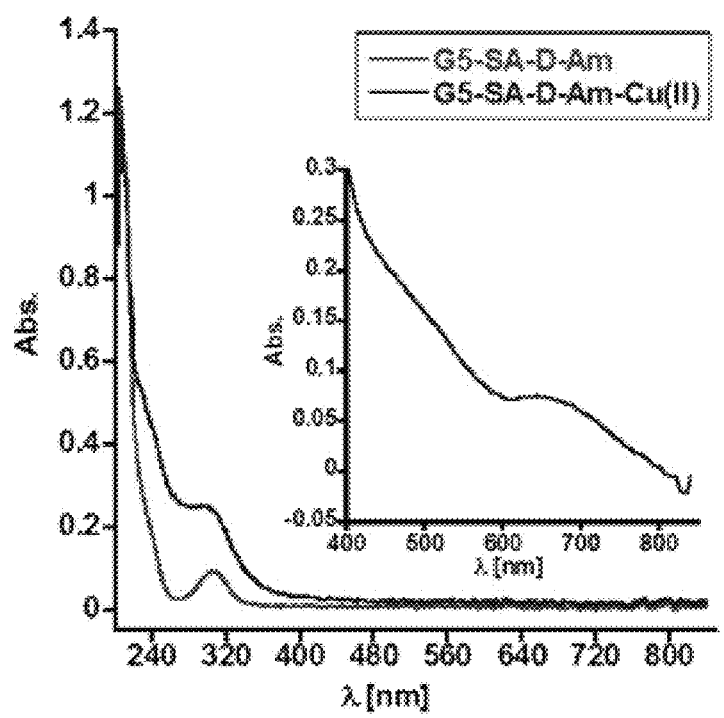
Figure 15A:
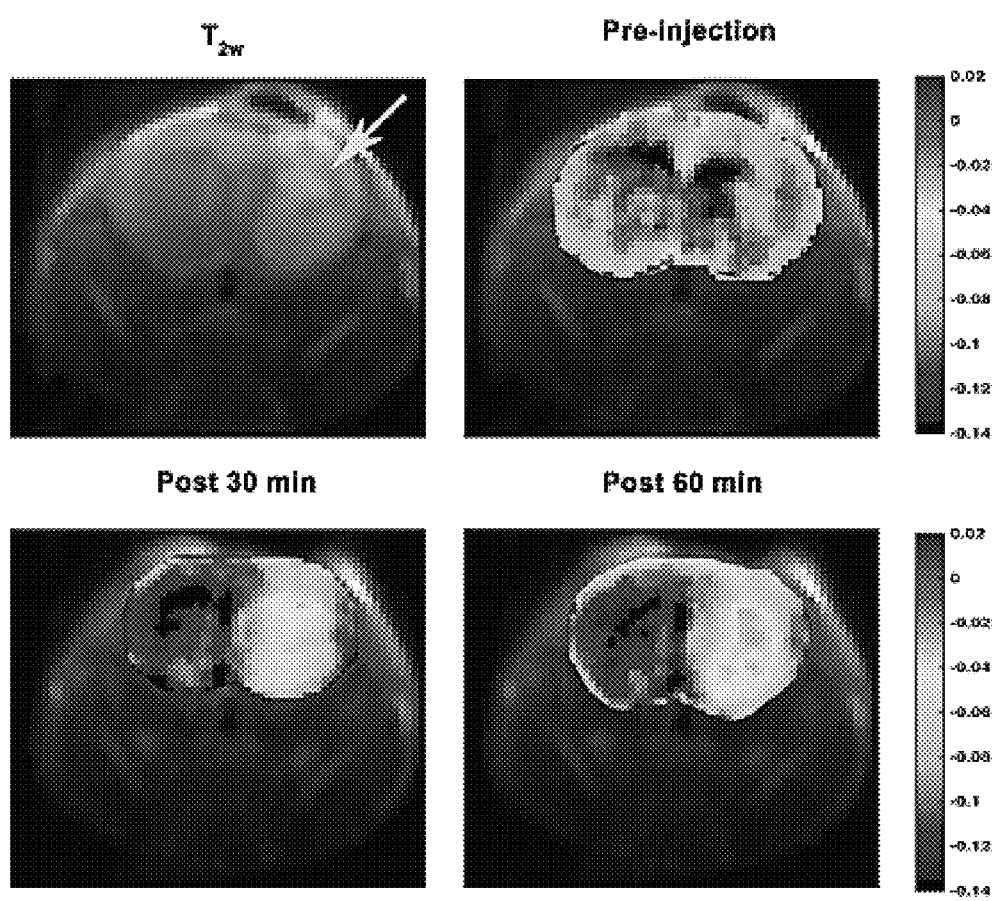
Figure 15B:
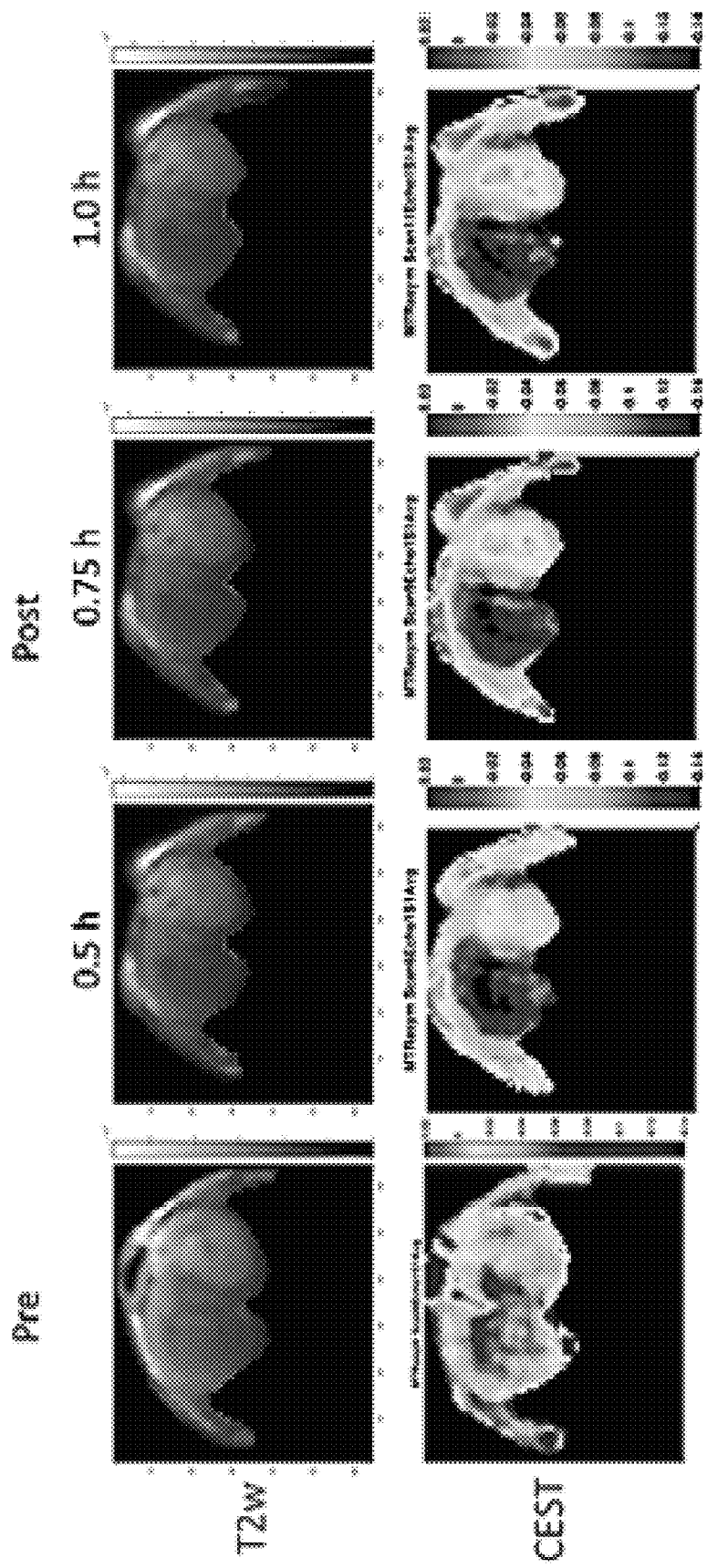
Figure 16:
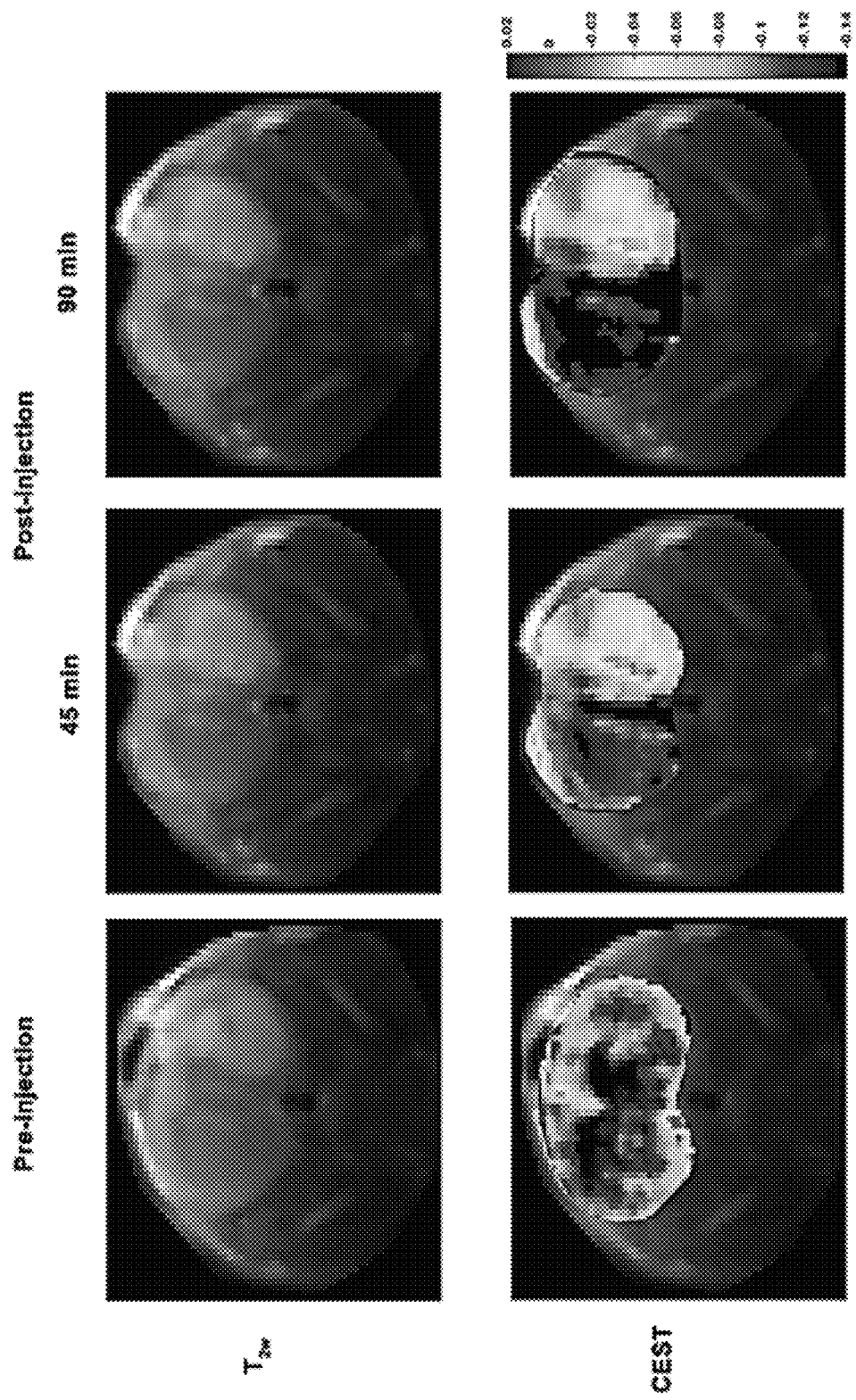
Figure 17:
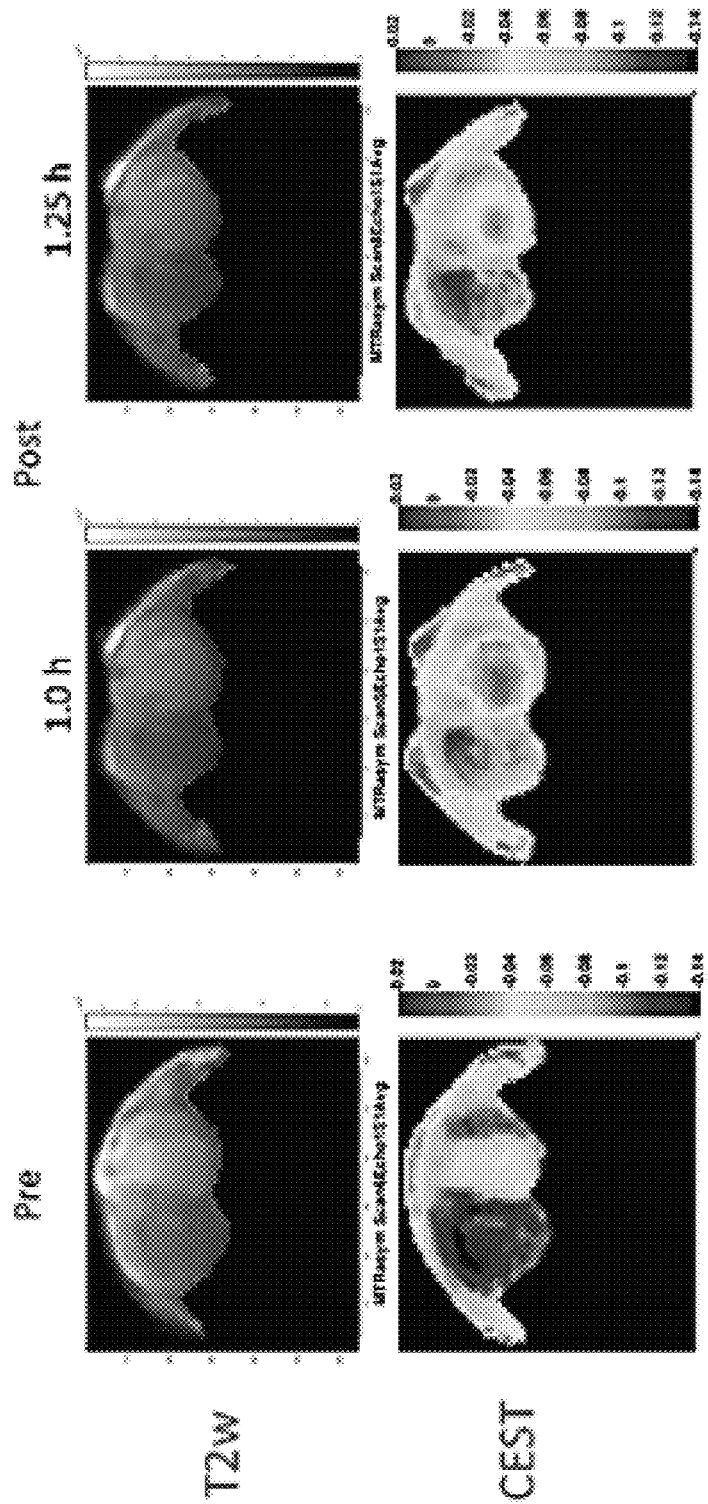
Figure 18A:
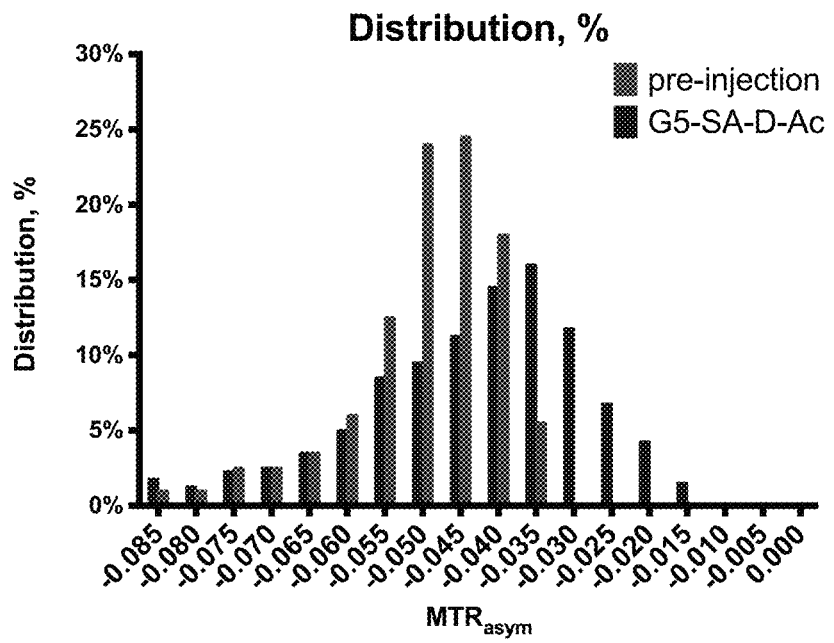
Figure 18B:
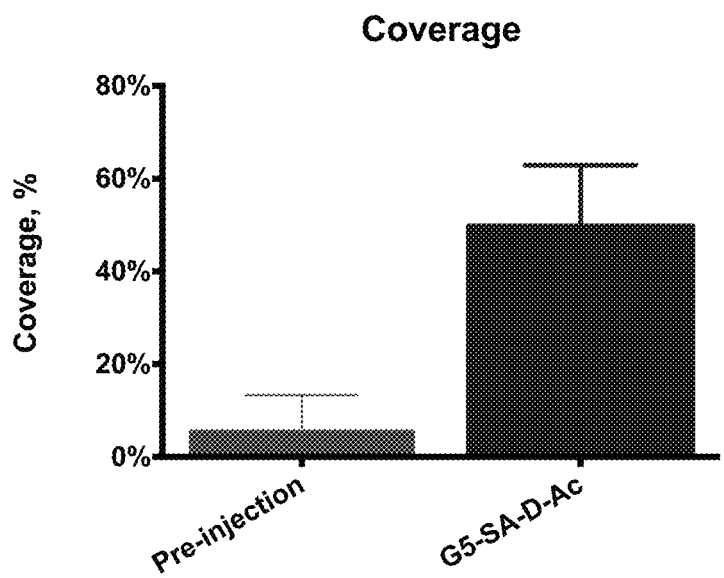

Having thus described the presently disclosed subject matter in general terms, reference will now be made to the accompanying Figures, which are not necessarily drawn to scale, and wherein:

FIG. 1A and FIG. 1B show (FIG. 1A) structural representation of generation 1 PAMAM dendrimer; the size (by 1 nm) and the number of terminal groups increase (2×) with each generation (e.g. generation 5 has 128 primary amines and a diameter of about 5 nm); (FIG. 1B) schematic representation of invented multifunctional dendritic nanoplatform; polyethyleneglycol or ligands such as cyclic Arg-Gly-Asp (cRGD), folic acid, cyclo(D-Tyr-Arg-Arg-Nal-Gly) (CPCR4) or antibody/antibody fragments targeting various cell surface proteins including integrins, folate receptor and chemokine receptor type 4 (CXCR4) can also be attached as terminal groups together with therapeutic agent;

FIG. 2 shows a synthesis scheme for carboxylation of 5-aminomethylsalicylic acid methyl ester (SA-ME);

FIGS. 3A-F show a schematic pathway for preparation of dendrimers with different functional groups; G5-Am—generation (5) PAMAM dendrimer, SA-ME—5-N-succinamylmethylsalicylic acid methyl ester, D—DOTA, Ac—acetyl, Diol—propyl-1,2-diol; numbers of conjugated functional groups were determined by combination of proton nuclear magnetic resonance ($^1$HNMR), matrix assisted laser desorption ionization time-of-flight (MALDI-TOF) and ultraviolet-visible (UV-Vis) spectroscopy;

FIG. 4 shows the reversed-phase high-performance liquid chromatography (RP-HPLC) chromatogram of the reaction mixture for synthesis 5-N-succinamylmethylsalicylic acid methyl ester (SA-ME);

FIG. 5 shows the $^1$H NMR spectrum of 5-N-succinamylmethylsalicylic acid methyl ester recorded using dimethyl sulfoxide (DMSO) as a solvent; spectrum clearly demonstrates high purity of SA-ME by the exclusive presence of signals related to the analyte and values of integrals are in good agreement with structure;

FIG. 6 shows the $^1$H NMR spectrum of G5-PAMAM ethylenediamine (EDA) core—dendrimer terminated with 128 primary amines (G5-Am) recorded using D$_2$O as a solvent; insert—partial structure of dendrimer (n=4) with theoretical number of CH$_2$ groups; values of integrals are in good agreement with number of protons in each group of CH$_2$ moieties;

FIG. 7 shows the $^1$H NMR spectrum of G5 PAMAM dendrimer conjugated with about 40 molecules of 5-N-succinamylmethylsalicylic acid methyl ester (step 1, G5-SAME-Am) recorded using D$_2$O as a solvent; values of integrals of signals related to dendrimer (between 3.3 and 2.2 ppm) and attached SA-ME (peaks 1, 2, 3, 4 and 6), indicate about 1:40 G5-Am:SA-ME molar ratio;

FIG. 8 shows the $^1$HNMR spectrum of G5 PAMAM dendrimer conjugated with about 40 molecules of 5-N-succinamylmethylsalicylic acid, about 4 molecules of DOTA and about 82 unmodified primary amines (step 3, G5-SA-D-Am) recorded using D$_2$O as a solvent. Conjugation of DOTA provided additional 64 and 32 protons with signals at about 2.46 and about 3.3 ppm, respectively; signals of these protons overlap with peaks of dendrimer leading to decrease of the signals related to S—N-succinamylmethylsalicylic acid. Absence of the peak at 3.7 ppm related to protons of methyl ester indicates successful deprotection of SA-ME;

FIG. 9 shows $^1$HNMR spectrum of generation 5 PAMAM dendrimer conjugated with about 40 molecules of 5-N-succinamylmethylsalicylic acid, about 4 molecules of DOTA, about 56 acetamide groups and 26 unmodified primary amines (step 5, G5-SA-D-Ac) recorded using $D_2O$ as a solvent; acylation of G5-SAME-D-Am resulted in an intense peak at 1.87 ppm in the spectrum of G5-SA-D-Ac;

FIG. 10 shows $^1$H NMR spectrum of generation 5 PAMAM dendrimer conjugated with about 40 molecules of 5-N-succinamylmethylsalicylic acid, about 4 molecules of DOTA, about 40 groups of 1,2-propanediol (Diol) and 42 unmodified primary amines (step 7, G5-SA-D-Diol) recorded using $D_2O$ as a solvent; presence of the additional signals between 3.4 and 3.84 ppm indicates successful glycidolation of G5-SAME-D-Am;

FIG. 11 shows matrix assisted laser desorption ionization (MALDI) of starting G5 PAMAM dendrimer, G5-SA-D-Ac, G5-SA-D-Diol and G5-SA-D-Ac final products; significant increase of molecular weight of final products compared to starting material indicates covalent attachment of functional groups to the dendrimer molecule; similar spectra were recorded for all intermediate products and were used to calculate number of salicylic acid and DOTA molecules attached to dendrimer as well as degree of acylation and hydroxylation (data not shown);

FIG. 12 shows representative of size distribution and zeta potential distribution obtained for G5-SA-D-Diol; similar size distributions with appropriate change in zeta potential distribution were observed for all nanoparticles;

FIG. 13A, FIG. 13B, FIG. 13C, and FIG. 13D show representative UV-Vis spectra acquired for: (FIG. 13A) 5-N-succinamylmethylsalicylic acid (SA-ME) recorded for concentrations ranging for 1 to 4 mM. Insert shows calibration obtained using maximum of absorbance at 309 nm, which was used to calculate number of SA groups conjugated to the dendrimer; (FIG. 13B) G5 PAMAM dendrimer at a concentration of 1 mM, showing only a low intensity peak at 235 nm and G5-SA-D-Am (synthetic step 3) recorded at concentration of 0.055 mM revealing a strong signal at 309 nm, that is related to SA; intensity of this peak confirms conjugation of 42 SA to the dendrimer; (FIG. 13C) DOTA without Cu(II), showing strong charge transfer (CT) in the UV range and d-d transitions (insert) in the visible range upon chelation of copper ions; for CT and d-d measurement, concentration of DOTA used was 1 mM and 10 mM, respectively with 1 mole equivalent of Cu(II) added; (FIG. 13D) G5-SA-D-Am with and without 4 equivalent (eq.) of Cu(II), with the presence of), matrix assisted laser desorption ionization band and increase in intensity in the UV range related to the CT transition indicating the presence of DOTA on the conjugate. Precipitation and no increase in signal were observed upon further addition of Cu(II); PAMAM dendrimer is a relatively weak Cu(II) chelator and in phosphate-buffered saline (PBS buffer) upon addition of copper ions to dendrimer without DOTA (G5-Am) precipitation of the copper phosphate was observed;

FIG. 14A, FIG. 14B, FIG. 14C, FIG. 14D, and FIG. 14E show the asymmetric magnetization transfer ratio (MTRasym) of CEST-based dendrimer conjugates with different surface properties; (FIG. 14A) acetylated, (FIG. 14B) hydroxylated and (FIG. 14C) amino-terminated; (FIG. 14D) exchange rate constant $k_{ex}$ calculation of protons in salicylic acid residues of CEST dendritic nanoparticles using quantifying exchange using saturation power (QUESP) method; (FIG. 14E) exchange rate constant $k_{ex}$ calculation of SA-dendrimer conjugates using QUESP method;

FIG. 15A and FIG. 15B show (FIG. 15A) in vivo CEST images acquired pre-, 30 min and 60 min post-intratumoral infusion of G5-SA-D-Ac conjugates into U87 glioblastoma xenografts in severe combined immunodeficiency (SCID) mice; MRI data, G5-SA-D-Ac dendrimer conjugates can be detected via CEST contrast within the tumor; images show CEST contrast reaching 3% above the pre-infusion magnetic resonance ((MR) image; the yellow arrow highlights tumor location; (FIG. 15B) in vivo characterization of G5-SA-D-Ac conjugate pre-, 0.5 h, 0.75 h and 1.0 h post-intratumoral infusion into U87 glioblastoma xenografts in SCID mice using CEST MRI, upper panels T2w images, lower panels average MTRasym;

FIG. 16 shows in vivo characterization of G5-SA-D-Ac conjugate prior and up to 1.5 hours after intratumoral infusion into U87 glioblastoma xenograft mouse model using CEST MRI, upper panels T2w images, lower panels average MTRasym from 8.7 to 9.9 ppm;

FIG. 17 shows in vivo characterization of G5-SA-D-Diol conjugate pre, 0.5 h, 0.75 h and 1.0 h post-intratumoral infusion into U87 glioblastoma tumor mice at different time points detected using CEST MRI upper panels T2w images, lower panels average MTRasym; and FIG. 18A and FIG. 18B show (FIG. 18A) histogram displaying the CEST contrast at 9.4 ppm within the brain tumor for two different times: pre-injection and 1 hr after G5-SA-D-Ac injection, with n=3 mice; (FIG. 18B) % of tumor covered assuming pixels with MTRasym>−0.035 contain G5-SA-D-Ac dendrimer.

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Pamam Dendrimer Based Cest Imaging Agents and Uses Thereof

Chemical exchange saturation transfer (CEST) is a novel MRI contrast mechanism that is well-suited for imaging, however, existing small molecule CEST agents suffer from low sensitivity. Salicylic acid conjugated dendrimers as a versatile, high performance nanoplatform are provided in the presently disclosed subject matter. In particular, nanocarriers based on generation 5-poly(amidoamine) (PAMAM) dendrimers with salicylic acid covalently attached to their surface have been prepared. The resulting conjugates produce strong CEST contrast 9.4 ppm from water with the proton exchange tuneable from about 1000 s$^{-1}$ to about 4500 s$^{-1}$, making these dendrimers well suited for sensitive detection. Furthermore, it has been demonstrated that these conjugates can be used for monitoring convection enhanced delivery into U87 glioblastoma bearing mice, with the contrast produced by these nanoparticles persisting for over 1.5 h and distributed over about 50% of the tumors. SA modified dendrimers represent a promising new nanoplatform for medical applications.

A. Compounds of Formula (I)

Accordingly, in some embodiments, the presently disclosed subject matter provides a PAMAM dendrimer of formula (I):

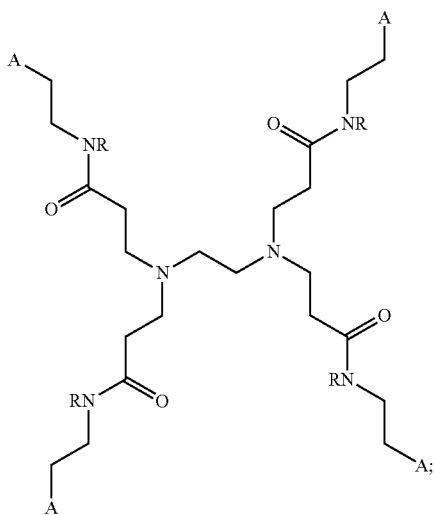

(I)

wherein: each A is independently selected from the group consisting of:

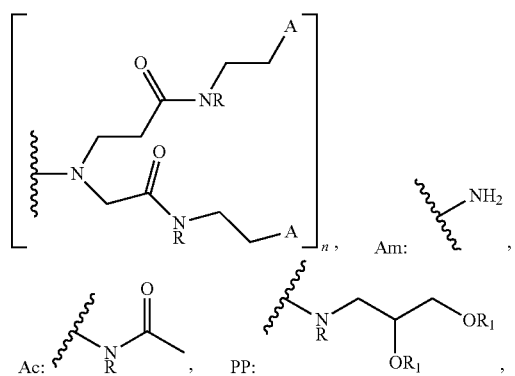

D: a metal chelating moiety optionally comprising a metal or a radiometal suitable for treating or imaging, T: a therapeutic agent, TG: a targeting agent, IM: an imaging agent, PEG-X: a polyethylene glycol residue, wherein X is

or TG, and —NR-L-W—(CH$_2$)$_m$-SA;

L is a linking group selected from the group consisting of —(CH$_2$)$_m$—, —C(=O)—(CH$_2$)$_m$—, —(CH$_2$—CH$_2$—O)$_t$—, —C(=O)—(CH$_2$—CH$_2$—O)$_t$—, —(O—CH$_2$—CH$_2$)$_t$—, —C(=O)—(O—CH$_2$—CH$_2$)$_t$—, —C(=O)—(CHR$_2$)$_m$—NR$_3$—C(=O)—(CH$_2$)$_m$—, —C(=O)—(CH$_2$)$_m$—O—C(=O)—NR$_3$—(CH$_2$)$_p$—, —C(=O)—(CH$_2$)$_m$—NR$_3$—C(=O)—O—CH$_2$)$_p$—, —C(=O)—(CH$_2$)$_m$—NR$_3$—C(=O)—NR$_3$—(CH$_2$)$_p$—, —C(=O)—(CH$_2$)$_m$—NR$_3$—C(=O)—(CH$_2$)$_p$—, —C(=O)—(CH$_2$)$_m$—C(=O)—NR$_3$—(CH$_2$)$_p$—, —C(=O)—(CH$_2$)$_m$—NR$_3$—C(=O)—NR$_3$—(CH$_2$)$_p$—, —C(=O)—(CH$_2$)$_m$—NR$_1$—C(=O)—NR$_3$—(CH$_2$)$_p$—, —C(=O)—(CH$_2$)$_m$—O—C(=O)—NR$_3$—, —C(=O)—CH$_2$)$_m$—O—C(=O)—NR$_3$—(CH$_2$)$_p$—, —C(=O)—(CH$_2$)$_m$—NR$_3$—C(=O)—O—(CH$_2$)$_p$—, polyethylene glycol, glutaric anhydride, albumin, lysine, and amino-acid; W is selected from the group consisting of —NR—C(=O)—, —C(=O)—NR—, —S—, —O—, and —SO$_2$—; SA is

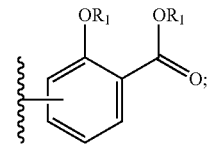

each R is independently selected from the group consisting of H and C$_1$-C$_4$ alkyl; each R$_1$ is independently selected from the group consisting of H, Na, C$_1$-C$_4$ alkyl, and a protecting group; each R$_2$ is independently selected from the group consisting of hydrogen, and —COOR$_1$, each R$_3$ is independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl; m and p are each independently an integer selected from the group consisting of 0, 1, 2, 3, 4, 5, 6, 7 and 8; t is a integer selected from the group consisting of 1, 2, 3, 4, 5, 6, 7, 8, 9, 10, 11 and 12; n is an integer selected from the group consisting of 1, 2, 3, 4, 5, 6, 7, 8, 9, and 10; or a salt or a stereoisomer thereof. In specific embodiments, n is 5.

In some embodiments, the ratio of SA:D:Am is about 42:4:82. In other embodiments, the ratio of SA:D:Ac:Am is about 42:4:56:26. In yet some other embodiments, wherein the ratio of SA:D:PP:Am is about 42:4:40:42.

In certain embodiments, TG is selected from the group consisting of: cRGD, folic acid, peptide, peptidomimetic, antibody, and antibody fragments.

In other embodiments, the antibody or antibody fragment is selected from the group consisting of integrins, folate receptor, somatostatin receptor, EGFR, tenascin, CXCR7, PD-L1, CSF1R, c-Met, HGF, Fab, Fab', F(ab')2, single chain antibody, nanobody, minibody, diabody, and CXCR4.

In more specific embodiments, D is selected from the group consisting of:
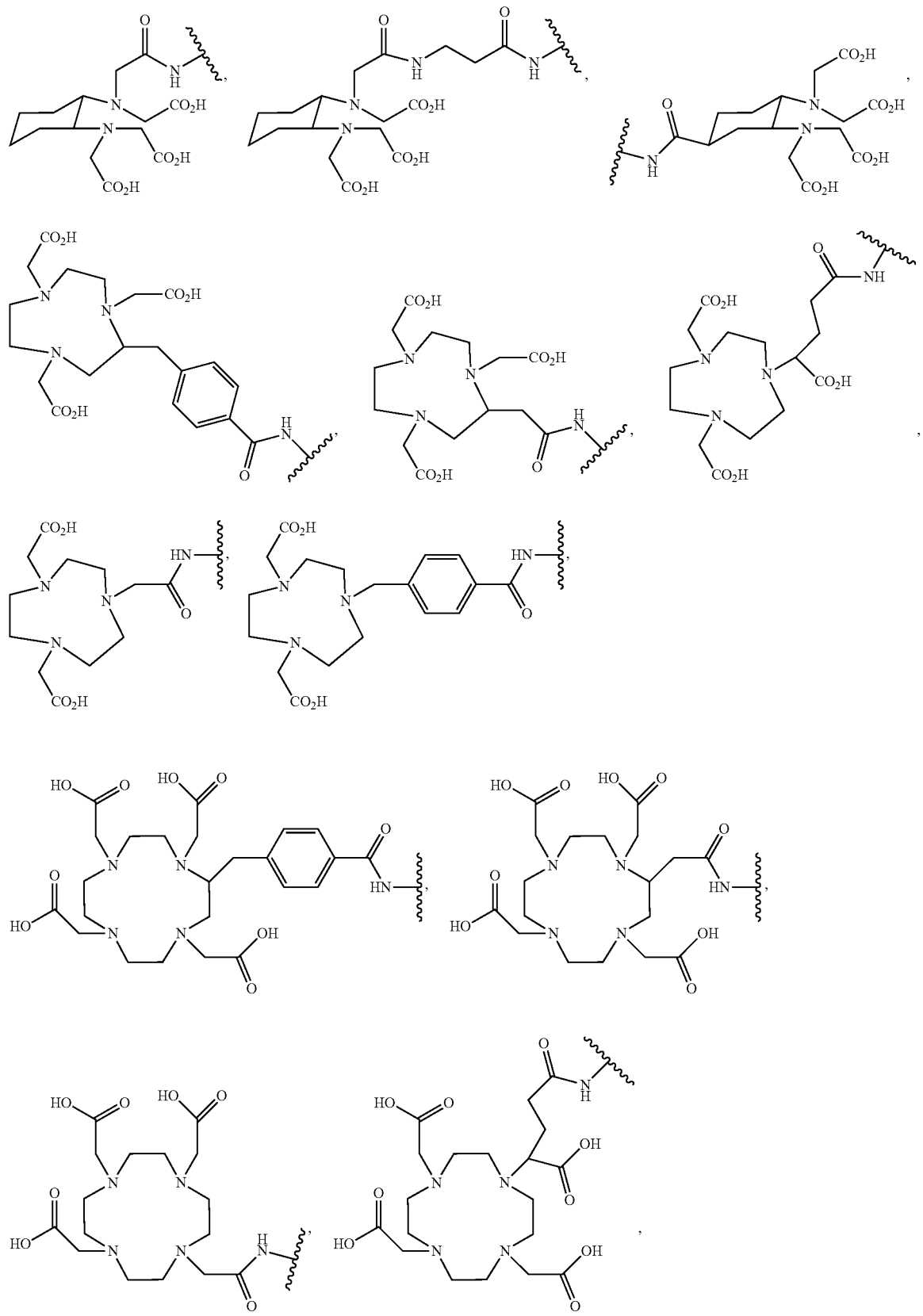

-continued

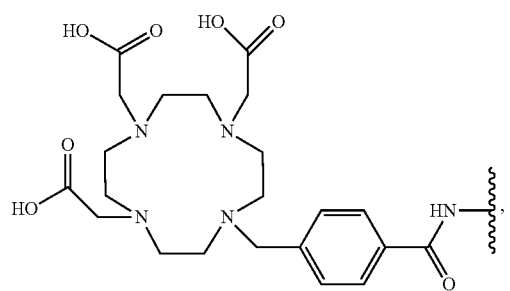
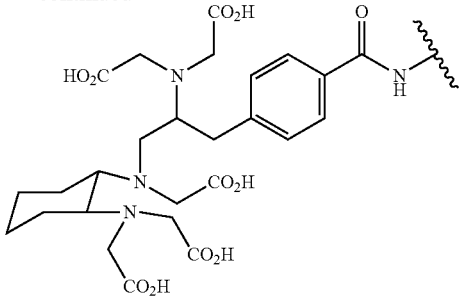

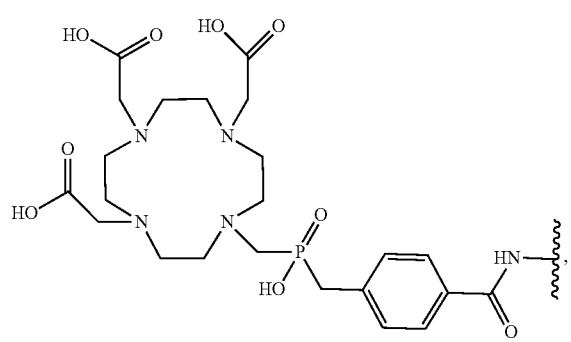
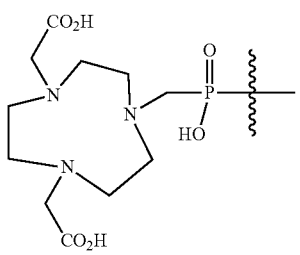
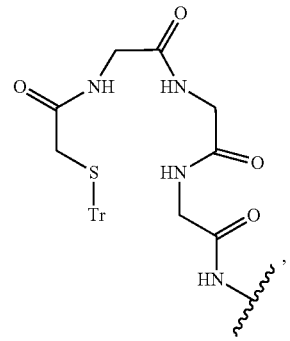

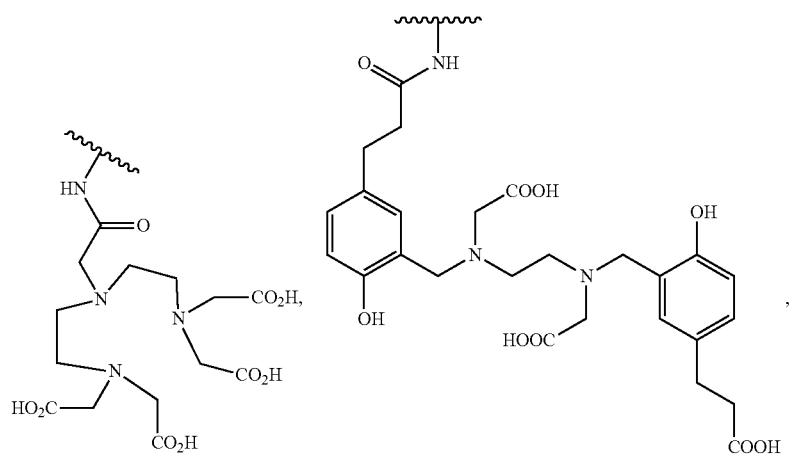

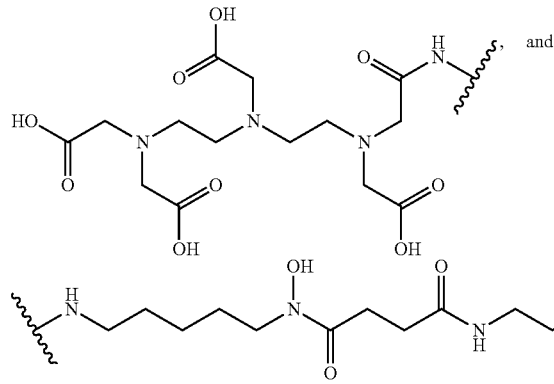

or a pharmaceutically acceptable salt thereof.

In specific embodiments, the metal is selected from the group consisting of Cu, Ga, Zr, Y, Tc, In, Lu, Bi, At, Ac, R, and Sr. In more specific embodiments, the metal is a radiometal and is selected from the group consisting of $^{64}$Cu, $^{67}$Cu, $^{68}$Ga, $^{60}$Ga, $^{89}$Zr, $^{86}$Y, $^{94m}$Tc, $^{67}$Ga, $^{99m}$Tc, $^{177}$Lu, $^{213}$Bi, $^{212}$Bi, $^{90}$Y, $^{211}$At, $^{225}$Ac, $^{223}$R, and $^{89}$Sr.

In representative embodiments, the dendrimer of formula (I) is selected from the group consisting of:

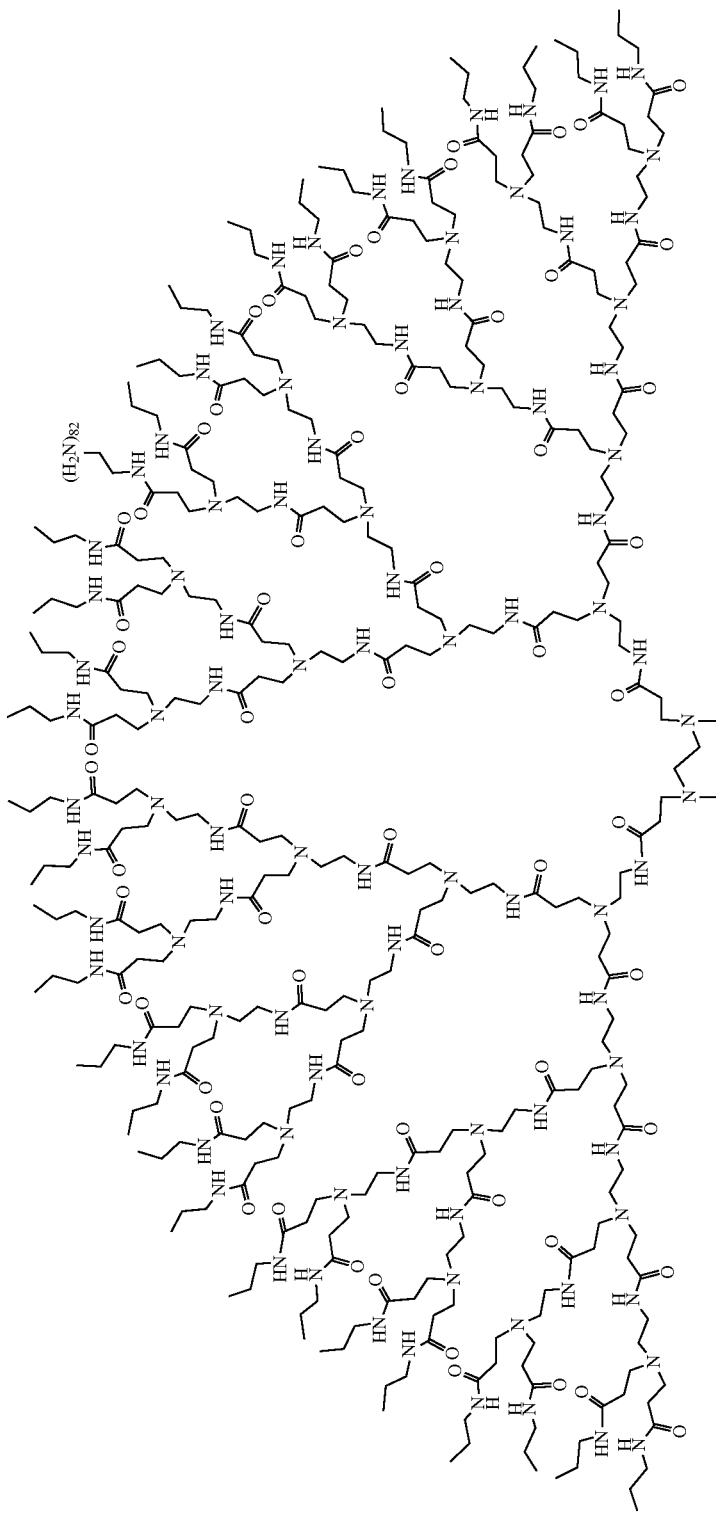

-continued
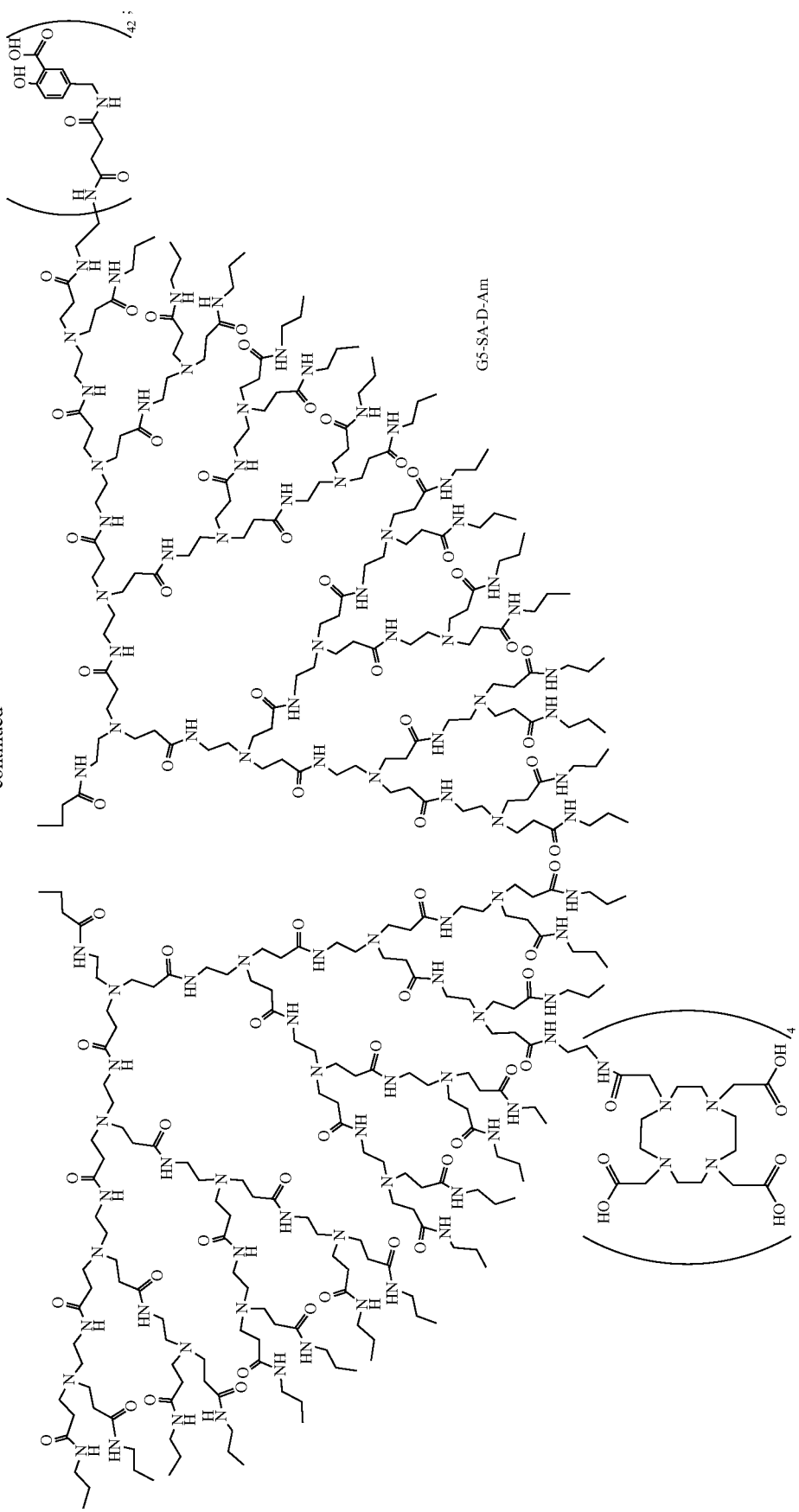
G5-SA-D-Am
and

-continued
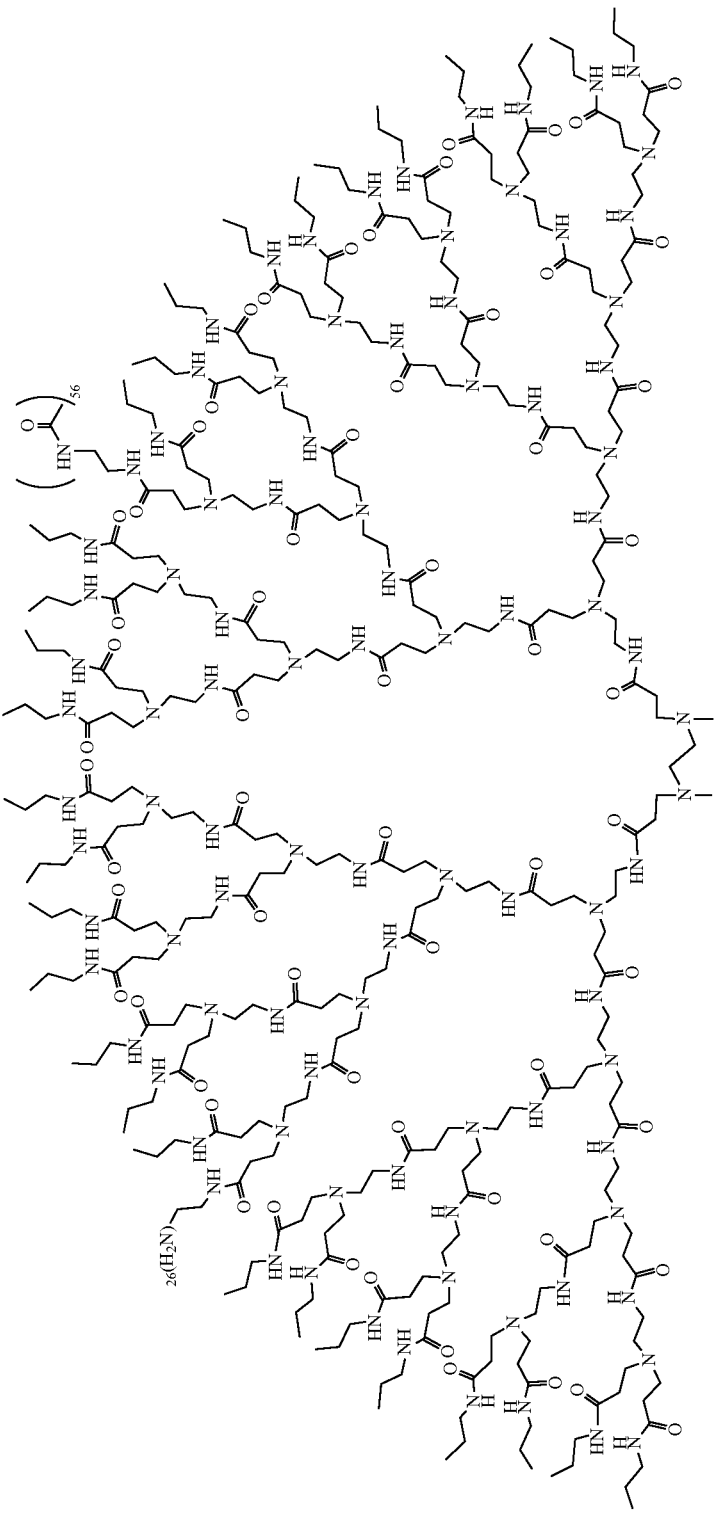

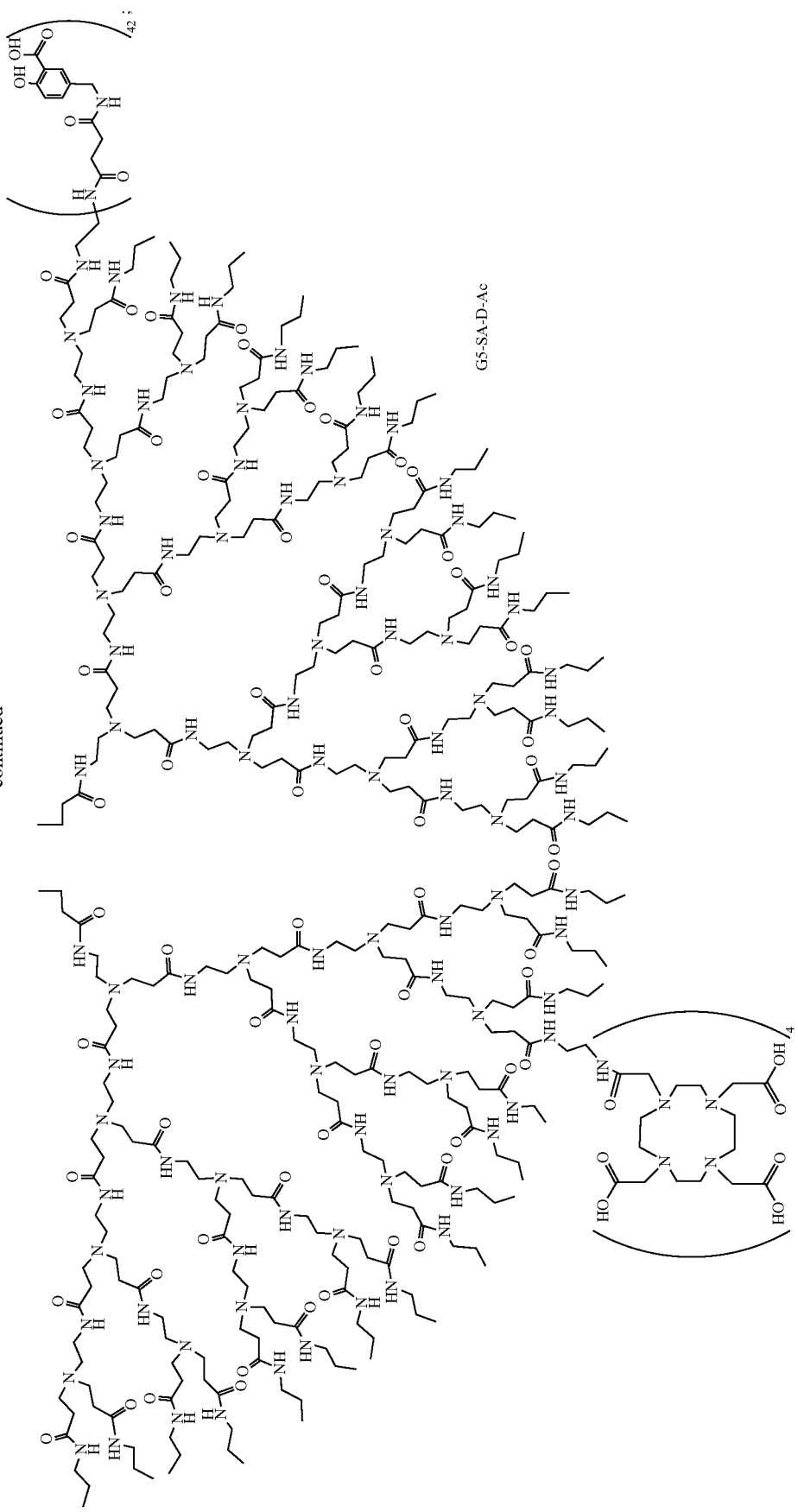

-continued
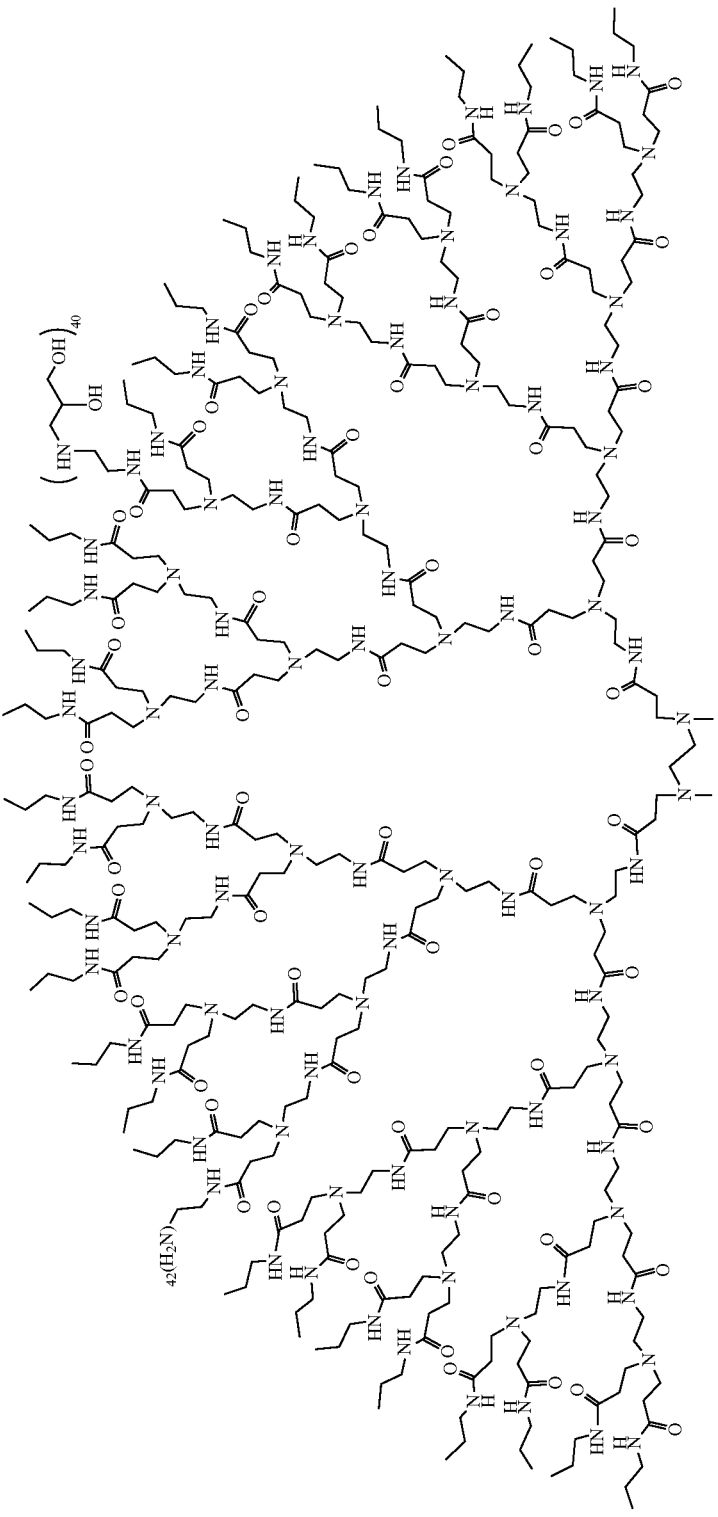

-continued
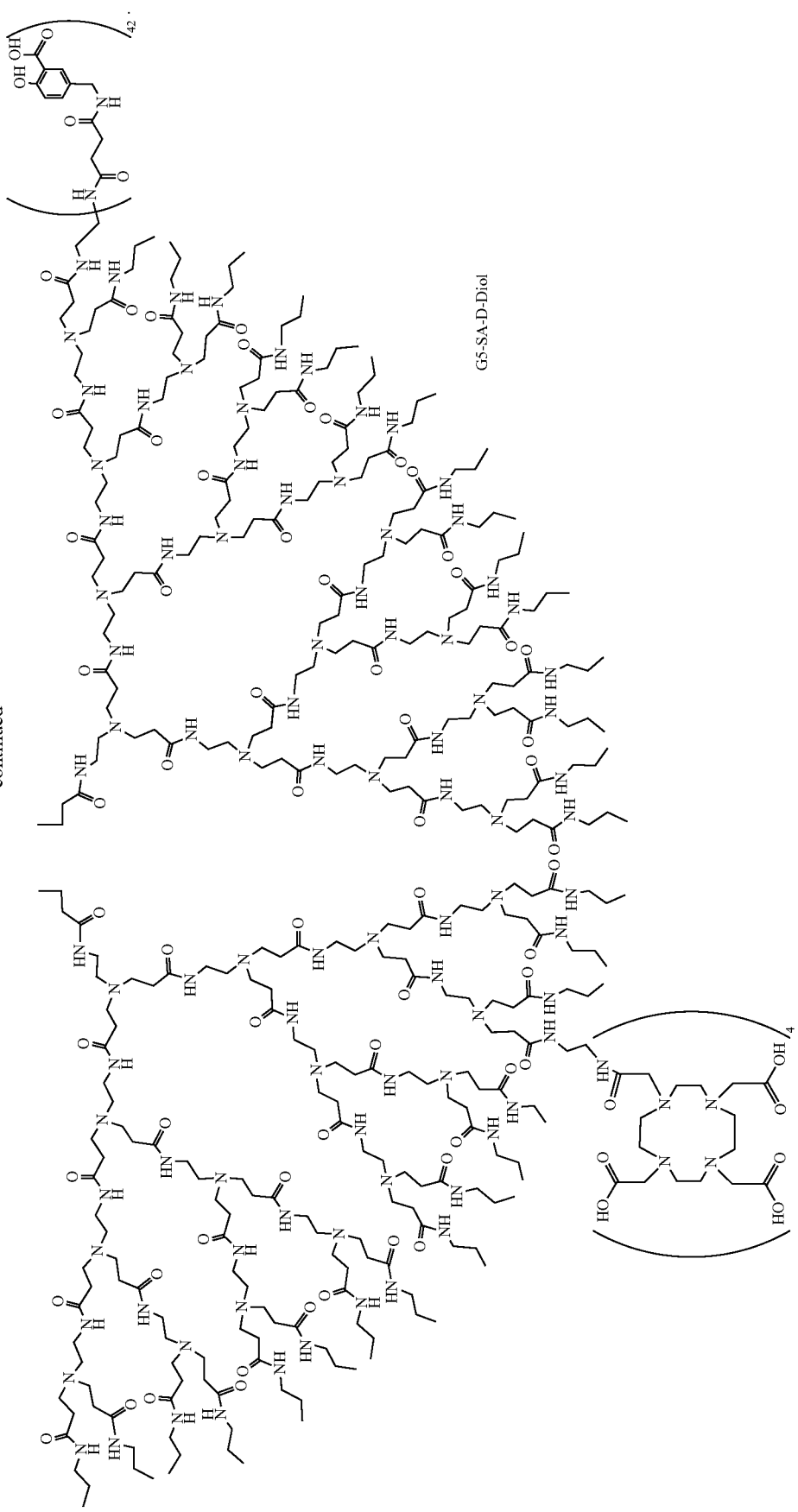
G5-SA-D-Diol

Although the presently disclosed subject matter pertains to PAMAM dendrimer having primary amines as terminal groups, the presently disclosed subject matter is not limited to the same and could be extended to PAMAM dendrimers having alcohol, thiol, and carboxylic acid terminal groups.

B. Pharmaceutical Compositions and Administration

In another aspect, the present disclosure provides a pharmaceutical comprising a compound of formula (I) in admixture with a pharmaceutically acceptable carrier, diluent or excipient. One of skill in the art will recognize that the pharmaceutical compositions include the pharmaceutically acceptable salts or hydrates of the compounds described above.

Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

C. Methods of Using the Compounds of Formula (I), or Pharmaceutical Compositions of any Thereof In some embodiments, the presently disclosed subject matter features a method for producing a magnetic resonance imaging (MRI) of a target, comprising: contacting the target with an effective amount of a magnetic resonance imaging contrast agent; and imaging the target using a Chemical Exchange Saturation Transfer (CEST) or frequency labeled exchange (FLEX) based MRI technique to produce the MR image of the target, wherein the MRI contrast agent is a dendrimer of formula (I):

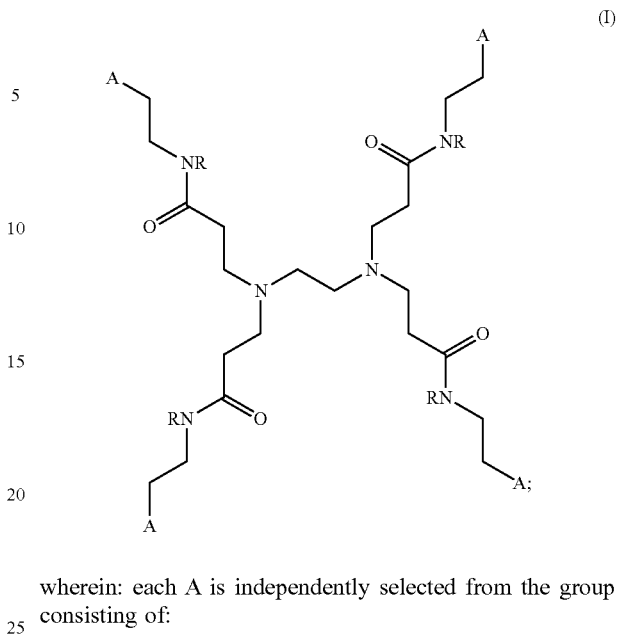

wherein: each A is independently selected from the group consisting of:

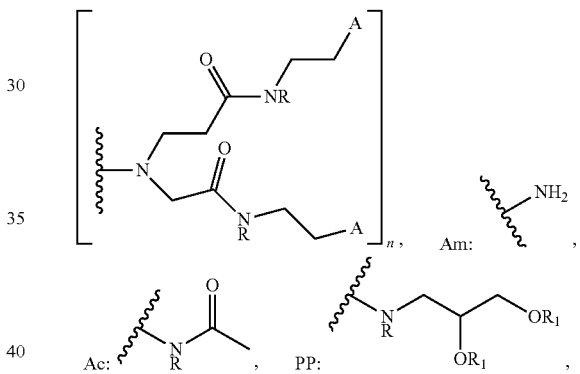

D: a metal chelating moiety optionally comprising a radiometal suitable for treating or imaging, T: a therapeutic agent, TG: a targeting agent, IM: an imaging agent, PEG-X: a polyethylene glycol residue, wherein X is

or TG, and $-NR-L-W-(CH_2)_m-SA$;

L is a linking group selected from the group consisting of $-(CH_2)_m-$, $-C(=O)-(CH_2)_m-$, $-(CH_2-CH_2-O)_t-$, $-C(=O)-(CH_2-CH_2-O)_t-$, $-(O-CH_2-CH_2)_t-$, $-C(=O)-(O-CH_2-CH_2)_t-$, $-C(=O)-(CHR_2)_m-NR_3-C(=O)-(CH_2)_m-$, $-C(=O)-(CH_2)_m-O-C(=O)-NR_3-(CH_2)_p-$, $-C(=O)-(CH_2)_m-NR_3-C(=O)-O-(CH_2)_p-$, $-C(=O)-(CH_2)_m-NR_3-C(=O)-NR_3-(CH_2)_p-$, $-C(=O)-(CH_2)_m-NR_3-C(=O)-(CH_2)_p-$, $-C(=O)-(CH_2)_m-C(=O)-NR_3-(CH_2)_p-$, $-C(=O)-(CH_2)_m-NR_3-C(=O)-NR_3-(CH_2)_p-$, $-C(=O)-(CH_2)_m-NR_1-C(=O)-NR_3-(CH_2)_p-$, $-C(=O)-(CH_2)_m-O-C(=O)-NR_3-$, $-C(=O)-CH_2)_m-O-$ $C(=O)-NR_3-(CH_2)_p-$, $-C(=O)-(CH_2)_m-NR_3-C(=O)-O-(CH_2)_p-$, polyethylene glycol, glutaric anhydride, albumin, lysine, and amino-acid; W is selected from the group consisting of $-NR-C(=O)-$, $-C(=O)-NR-$, $-S-$, $-O-$, and $-SO_2-$; SA is

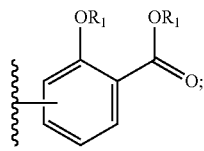

each R is independently selected from the group consisting of H and $C_1$-$C_4$ alkyl; each $R_1$ is independently selected from the group consisting of H, Na, $C_1$-$C_4$ alkyl, and a protecting group; each $R_2$ is independently selected from the group consisting of hydrogen, and $-COOR_1$; each $R_3$ is independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl; m and p are each independently an integer selected from the group consisting of 0, 1, 2, 3, 4, 5, 6, 7 and 8; t is a integer selected from the group consisting of 1, 2, 3, 4, 5, 6, 7, 8, 9, 10, 11 and 12; n is an integer selected from the group consisting of 1, 2, 3, 4, 5, 6, 7, 8, 9, and 10; or a salt or a stereoisomer thereof. "Contacting" means any action which results in at least one compound comprising the imaging agent of the presently disclosed subject matter physically contacting the target.

Magnetic resonance imaging systems are known in the art and commercially available. In certain aspects, the magnetic resonance imaging system comprises an imaging apparatus configured to perform a CEST or FLEX MR technique using one or more compounds as described herein.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

In specific embodiments, n is 5.

In some embodiments, the ratio of SA:D:Am is about 42:4:82. In other embodiments, the ratio of SA:D:Ac:Am is about 42:4:56:26. In yet some other embodiments, the ratio of SA:D:PP:Am is about 42:4:40:42.

In certain embodiments, TG is selected from the group consisting of: cRGD, folic acid, peptide, peptidomimetic, antibody, and antibody fragments.

In further embodiments, the antibody or antibody fragment is selected from the group consisting of integrins, folate receptor, somatostatin receptor, epidermal growth factor receptor (EGFR), tenascin, C-X-C chemokine receptor type 7 (CXCR7), programmed death-ligand 1 (PD-L1), colony stimulating factor 1 receptor (CSF1R), hepatocyte growth factor (HGF, c-Met), fragment antigen-binding (Fab), Fab', F(ab')2, single chain antibody, nanobody, minibody, diabody, and C-X-C chemokine receptor type 4 (CXCR4).

In some embodiments, D is selected from the group consisting of:

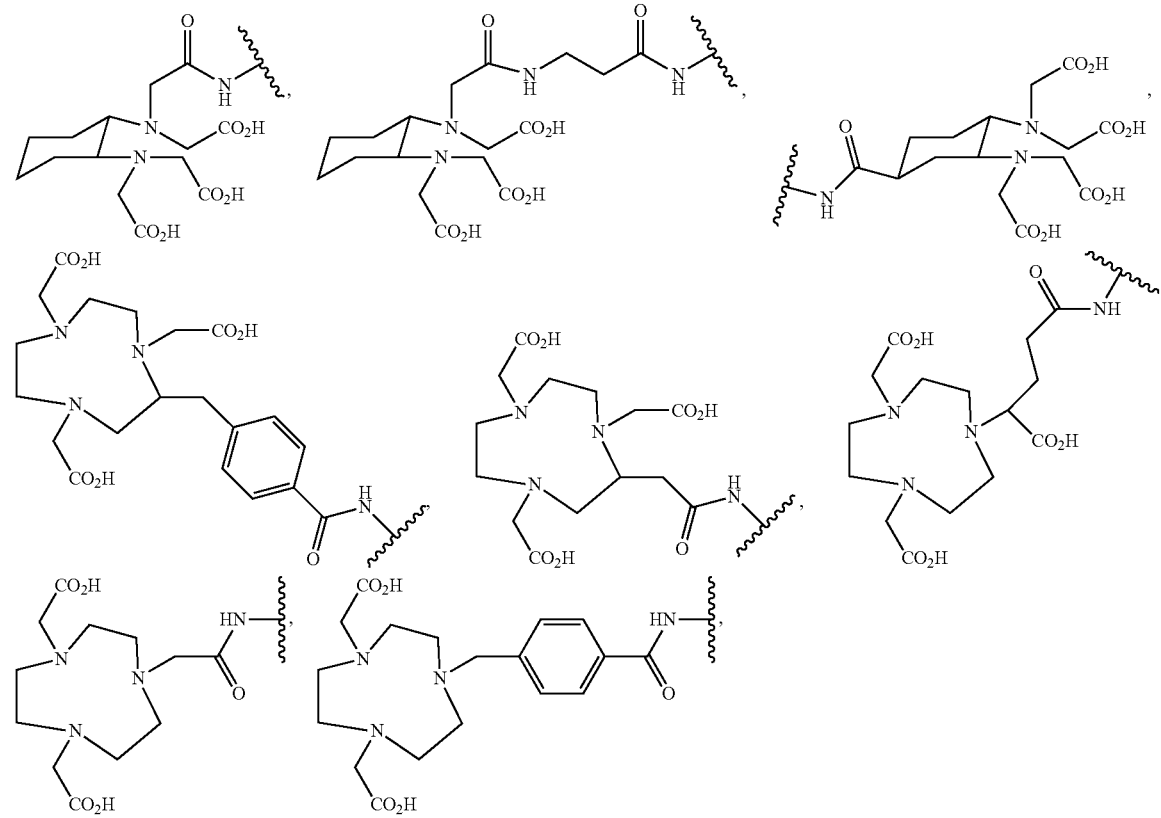

-continued
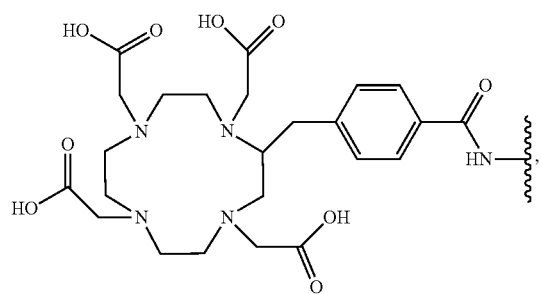
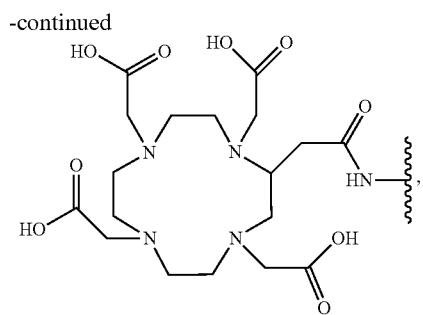
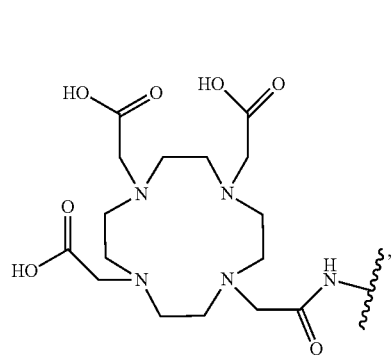
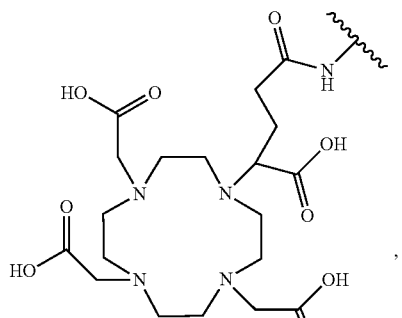
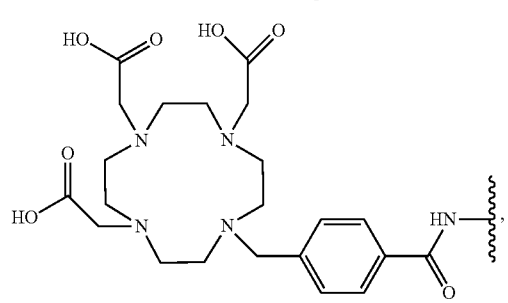
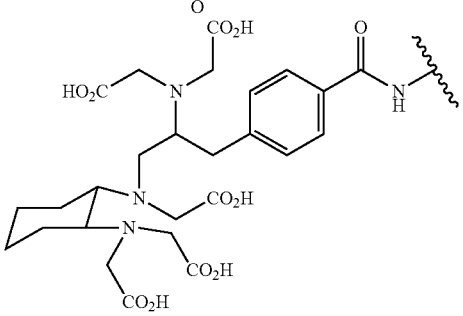
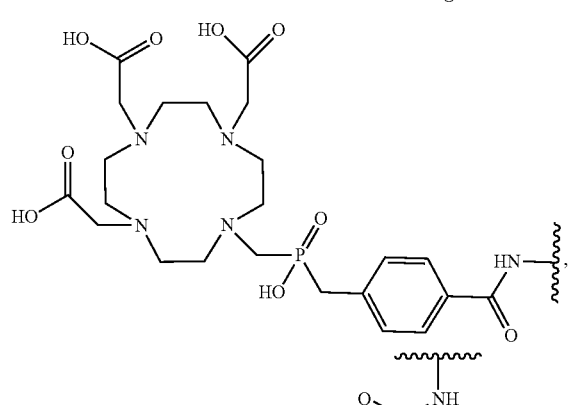
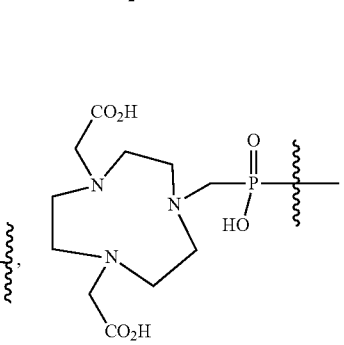
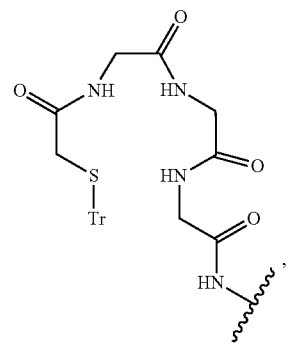
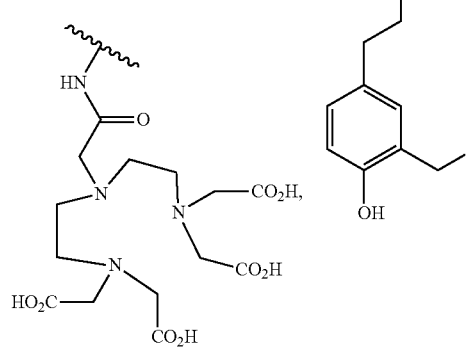
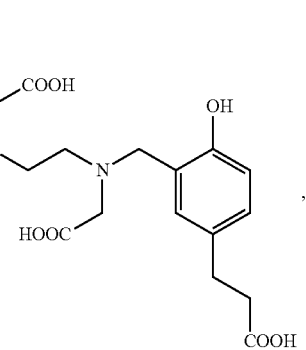

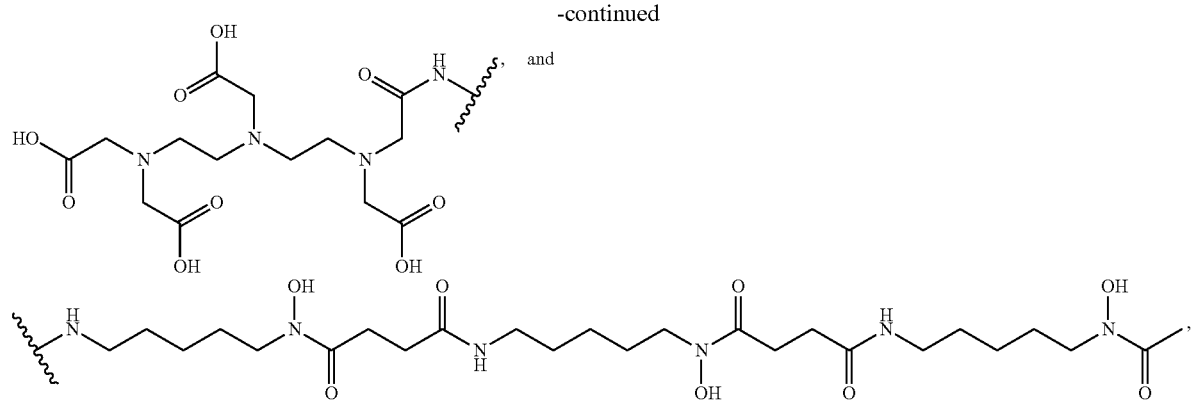
or a pharmaceutically acceptable salt thereof.
In representative embodiments, the dendrimer of formula (I) is selected from the group consisting of:

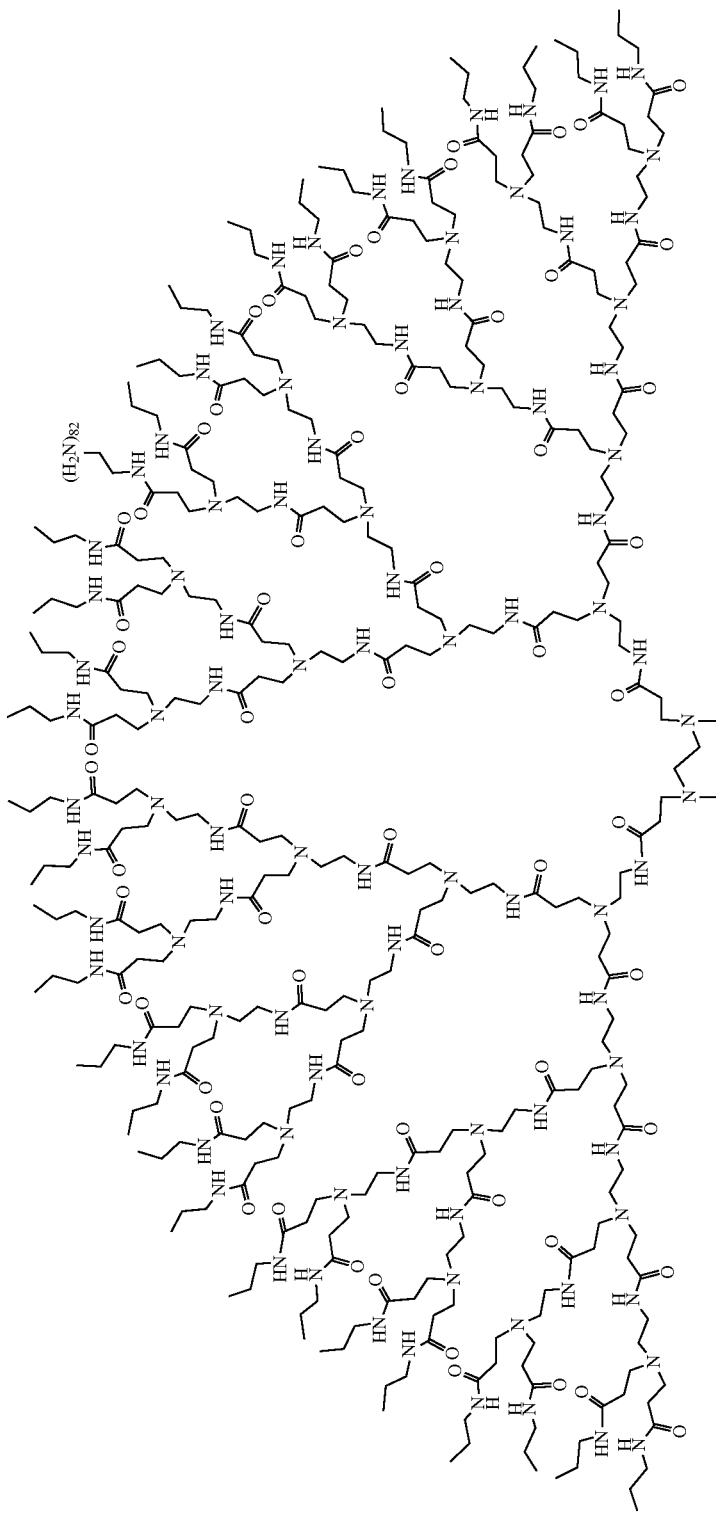

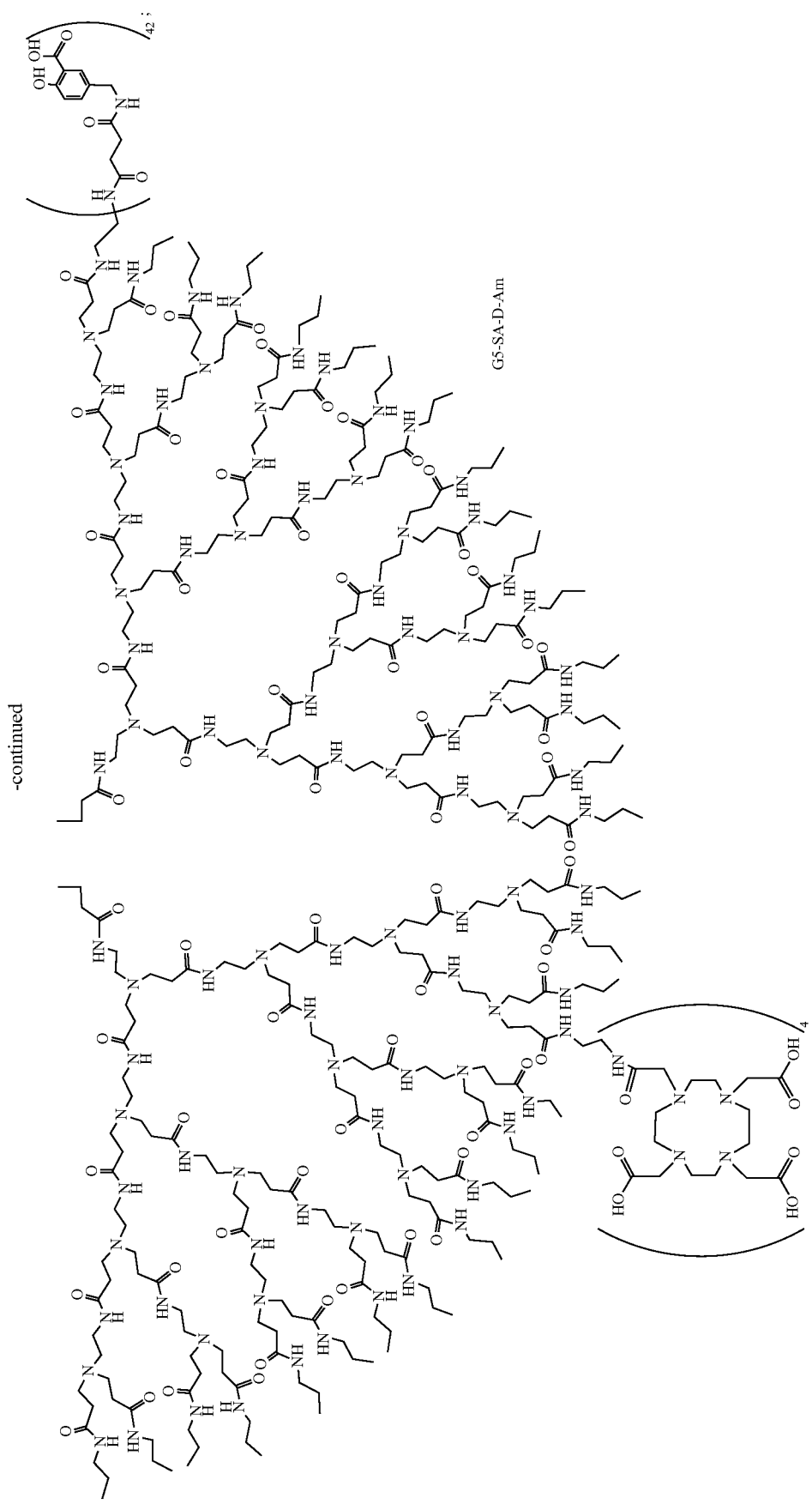

-continued
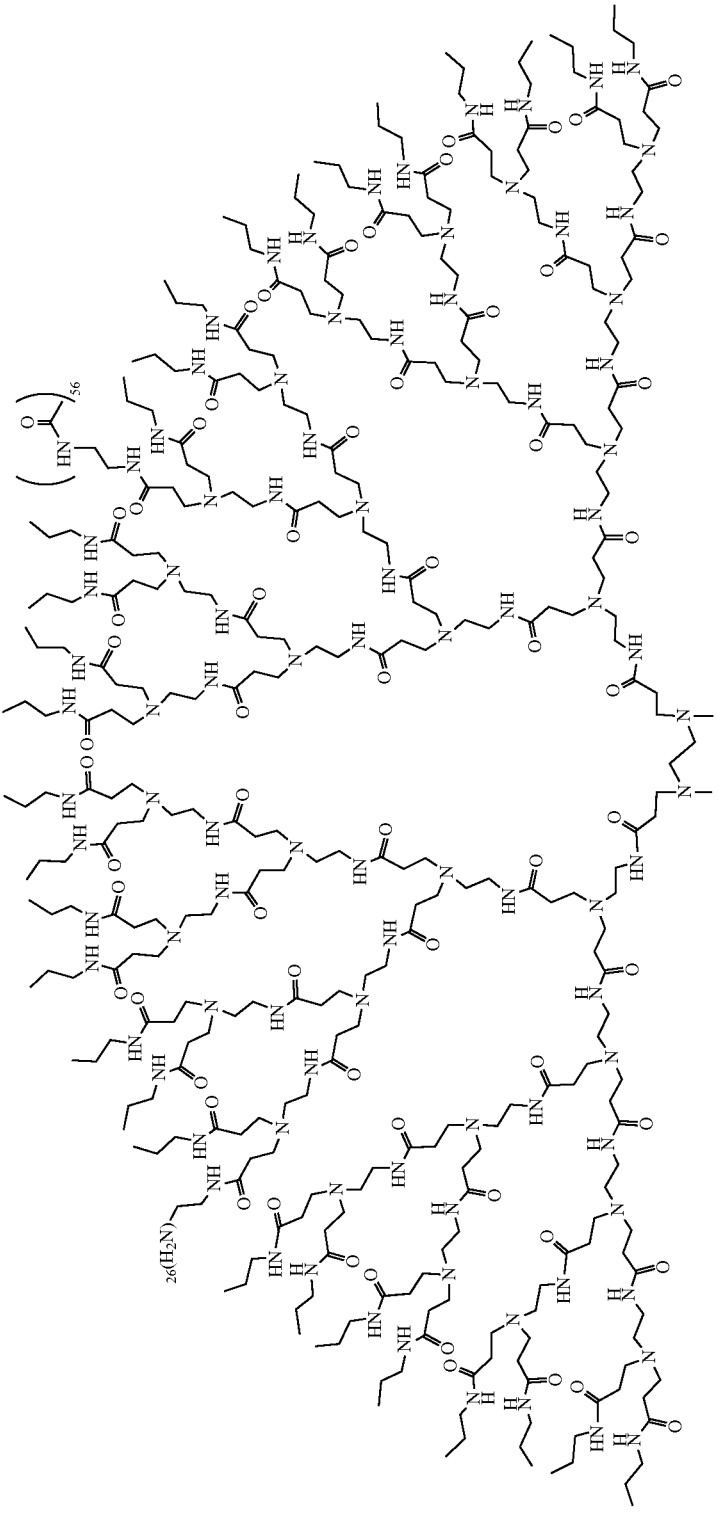

-continued
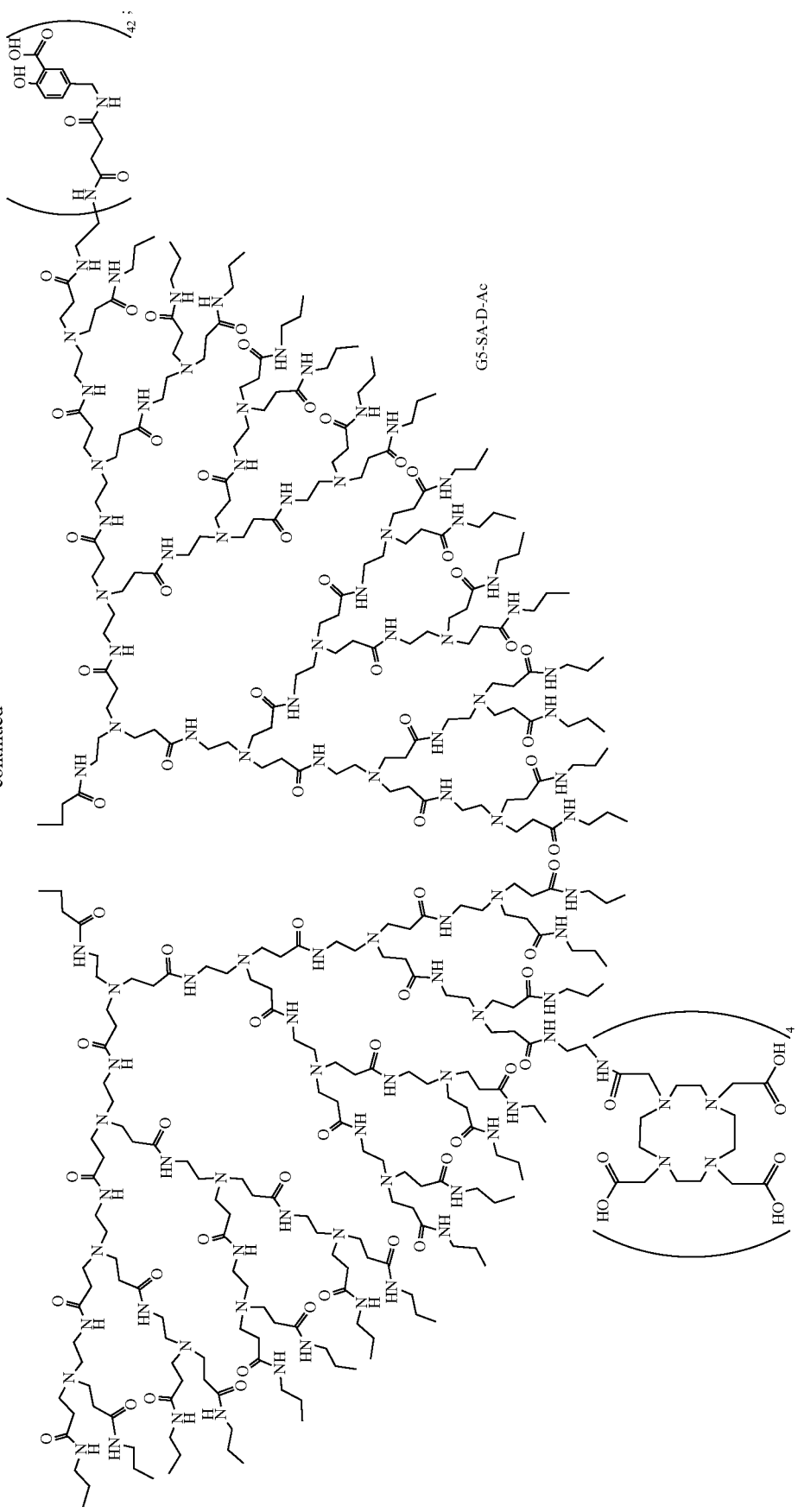

-continued
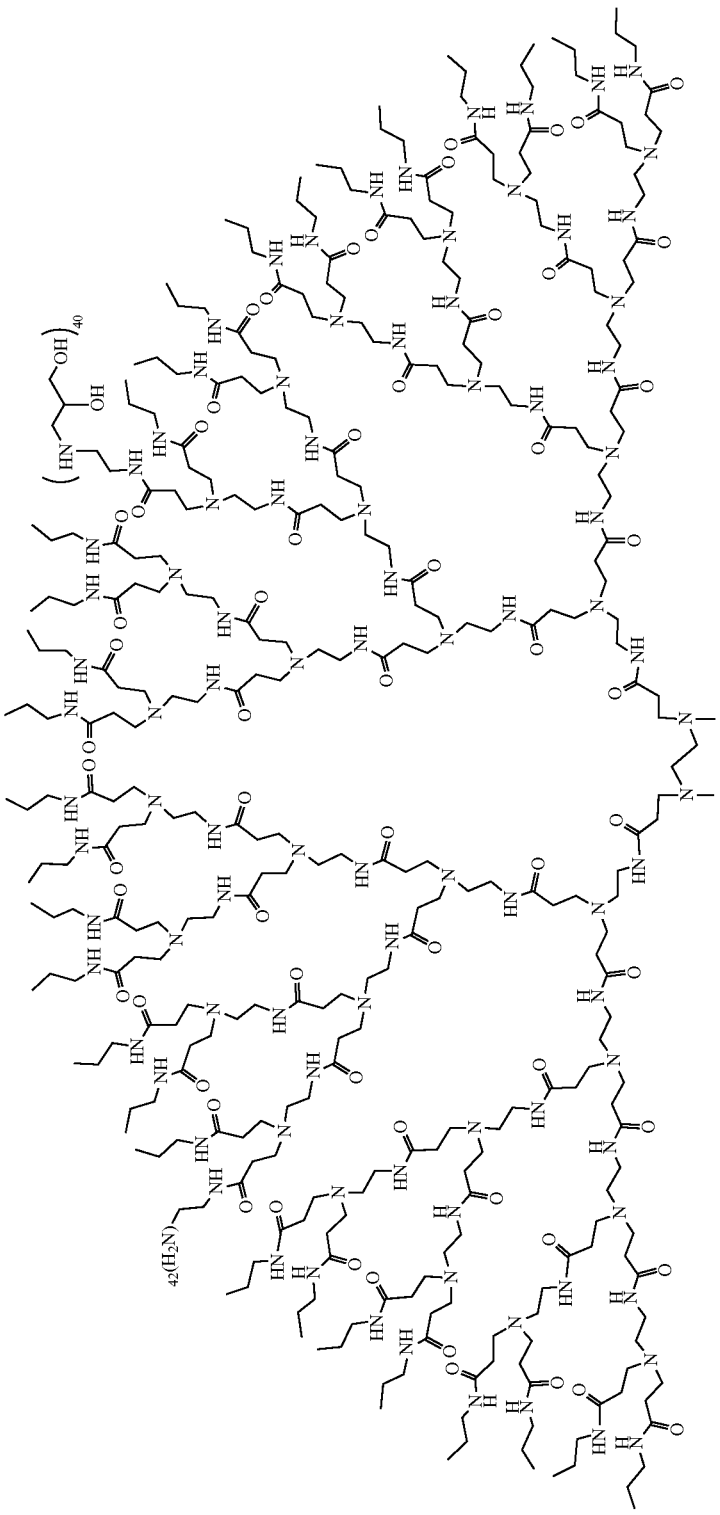

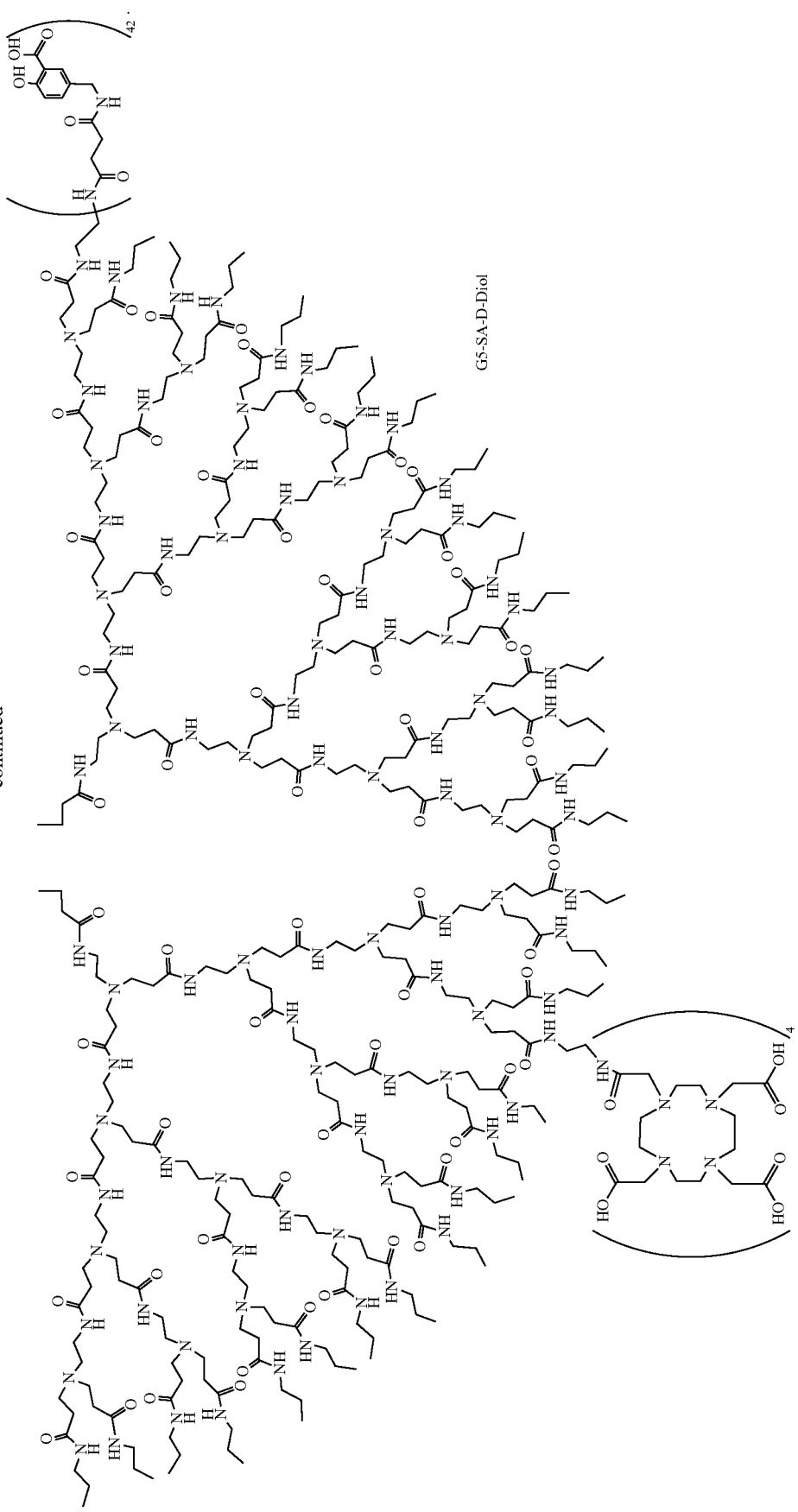

In further embodiments, the target is selected from the group consisting of a cell, a biological tissue, an organ, a tumor, a ligand, a biomarker, a therapeutically active agent, a metal ion, a chemotherapeutic, an antigen, a nanoparticle, a receptor, and a cation.

In other embodiments, the method can be practiced in vitro or ex vivo by introducing, and preferably mixing, the compound and cell(s) or tumor(s) in a controlled environment, such as a culture dish or tube. The method can be practiced in vivo, in which case contacting means exposing the target in a subject to at least one compound of the presently disclosed subject matter, such as administering the compound to a subject via any suitable route. According to the presently disclosed subject matter, contacting may comprise introducing, exposing, and the like, the compound at a site distant to the cells to be contacted, and allowing the bodily functions of the subject, or natural (e.g., diffusion) or man-induced (e.g., swirling) movements of fluids to result in contact of the compound and the target.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. In some embodiments, the subject is human. In other embodiments, the subject is non-human.

In other particular embodiments, the method comprises further measuring a chemical shift change of exchangeable protons in said MRI contrast agent. In other embodiments, the target is imaged using CEST MRI. In yet other embodiments, the target is imaged using FLEX MRI. In further embodiments, the MR imaging is performed in combination with positron emission tomography (PET) and the radiometal is selected from the group consisting of $^{64}$Cu, $^{67}$Cu, $^{68}$Ga, $^{60}$Ga, $^{89}$Zr, $^{86}$Y and $^{94m}$Tc. In other embodiments, the MR imaging is performed in combination with single-photon emission computed tomography (SPECT) and the radiometal is selected from the group consisting of $^{111}$In, $^{67}$Ga, $^{99m}$Tc, and $^{177}$Lu. The methods of the presently disclosed subject matter are useful for diagnosing, based on an image of the target in a subject, whether the subject may have a particular disease (e.g., brain cancer, lymphatic vessels diseases, and the like). The methods also allow monitoring, based on an MR image of the target in a subject, progression or regression of a disease or condition in the subject. The methods of the presently disclosed subject also allow treating and/or preventing a disease or condition in a subject in need thereof. In some embodiments, the radiometal suitable for radiotherapy is selected from the group consisting of $^{177}$Lu, $^{213}$Bi, $^{212}$Bi, $^{90}$Y, $^{211}$At, $^{225}$Ac, $^{223}$R, and $^{89}$Sr.

As used herein, the term "treating" can include reversing, alleviating, inhibiting the progression of, preventing or reducing the likelihood of the disease, or condition to which such term applies, or one or more symptoms or manifestations of such disease or condition.

"Preventing" refers to causing a disease, condition, or symptom or manifestation of such, or worsening of the severity of such, not to occur. Accordingly, the presently disclosed compounds can be administered prophylactically to prevent or reduce the incidence or recurrence of the disease, or condition.

In some embodiments, the disease or condition is selected from the group consisting of cancer and lymphatic vessels diseases. In particular embodiments, the cancer is brain cancer.

The methods of the presently disclosed subject matter are also useful monitoring a site specific delivery of the therapeutic agent by localizing the dendrimer to the site in need of treatment and releasing the therapeutically active agent at the site in need of treatment.

The methods of the presently disclosed subject matter can also be useful for identifying sentinel lymph nodes for removal using sentinel lymph node biopsies.

The CEST approach of the presently disclosed subject matter can be further extended to designing other novel responsive agents for molecular and cellular MRI applications. Certain design criteria for creating MRI contrast agents can be found in Que et al. (Chem Soc. Rev. 2010, 39, 51-60) and Hyman et al. (Coordination Chemistry Reviews, 256 (2012), 2333-2356).

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., C$_1$-C$_{10}$ means one to ten carbons, including 1, 2, 3, 4, 5, 6, 7, 8, 9, and 10 carbons). In particular embodiments, the term "alkyl" refers to C$_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C$_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to C$_{1-8}$ straight-chain alkyls. In other embodiments, "alkyl" refers, in particular, to C$_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, alkylamino, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_{2S}$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)— CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene ($-CH_2-$); ethylene ($-CH_2-CH_2-$); propylene ($-(CH_2)_3-$); cyclohexylene ($-C_6H_{10}-$); $-CH=CH-CH=CH-$; $-CH=CH-CH_2-$; $-CH_2CH_2CH_2CH_2-$, $-CH_2CH=CHCH_2-$, $-CH_2C\equiv CCH_2-$, $-CH_2CH_2CH(CH_2CH_2CH_3)CH_2-$, $-(CH_2)_q-N(R)-(CH_2)_r-$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($-O-CH_2-O-$); and ethylenedioxyl ($-O-(CH_2)_2-O-$). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, $-CH_2-CH_2-S-CH_2-CH_2-$ and $-CH_2-S-CH_2-CH_2-NH-CH_2-$. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

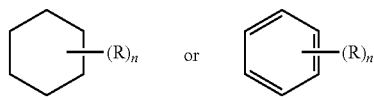

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

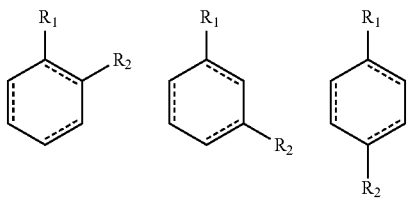

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⁓⁓⁓⁓ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO₂R', —C(O)NR'R", —OC(O)NR'R", —NR"C(O)R', —NR'—C(O)NR"R'", —NR"C(O)OR', —NR—C(NR'R")=NR'", —S(O)R', —S(O)₂R', —S(O)₂NR'R", —NRSO₂R', —CN and —NO₂ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R"', —OC(O)R', —C(O)R', —$CO_2$R', —C(O)NR'R", —OC(O)NR'R", —NR"C(O)R', —NR'—C(O)NR"R"', —NR"C(O)OR', —NR—C(NR'R"R"')═NR"", —NR—C(NR'R")═NR"'-S(O)R', —$S(O)_2$R', —$S(O)_2$NR'R", —$NRSO_2$R', —CN and —$NO_2$, —R', —$N_3$, —CH(Ph)$_2$, fluoro($C_1$-$C_4$)alkoxo, and fluoro($C_1$-$C_4$)alkyl, in a number ranging from zero to the total number of open valences on aromatic ring system; and where R', R", R"' and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R"' and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-($CH_2$)$_r$—B—, wherein A and B are independently —CRR'—, —O—, —NR—, —S—, —S(O)—, —$S(O)_2$—, —$S(O)_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —$S(O)_2$—, or —$S(O)_2$NR'—. The substituents R, R', R" and R"' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(═O)—, wherein R is an alkyl, alkenyl, alkynyl, aryl, carbocyclic, heterocyclic, or aromatic heterocyclic group as defined herein). As such, the term "acyl" specifically includes arylacyl groups, such as a 2-(furan-2-yl)acetyl)- and a 2-phenylacetyl group. Specific examples of acyl groups include acetyl and benzoyl. Acyl groups also are intended to include amides, —RC(═O)NR', esters, —RC(═O)OR', ketones, —RC(═O)R', and aldehydes, —RC(═O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(═O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(═O)— group. Exemplary aryloxycarbonyl groups include phenoxy- and naphthoxy-carbonyl.

"Aralkoxycarbonyl" refers to an aralkyl-O—C(═O)— group. An exemplary aralkoxycarbonyl group is benzyloxycarbonyl.

"Carbamoyl" refers to an amide group of the formula —C(═O)$NH_2$. "Alkylcarbamoyl" refers to a R'RN—C(═O)— group wherein one of R and R' is hydrogen and the other of R and R' is alkyl and/or substituted alkyl as previously described. "Dialkylcarbamoyl" refers to a R'RN—C(═O)— group wherein each of R and R' is independently alkyl and/or substituted alkyl as previously described.

The term carbonyldioxyl, as used herein, refers to a carbonate group of the formula —O—C(═O)—OR.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R"', wherein R', R", and R"' are each independently selected from the group consisting of alkyl groups. Additionally, R', R", and/or R"' taken together may optionally be —($CH_2$)$_k$— where k is an integer from 2 to 6. Examples include, but are not limited to, methylamino, dimethyl-amino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S($O_2$)R.

The term "sulfoxide" refers to a compound having a sulfinyl group —S(O)R

The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

A "dendrimer" is highly branched, star-shaped macromolecules with nanometer-scale dimensions.

As used herein, an "oligomer" includes a few monomer units, for example, in contrast to a polymer that potentially can comprise an unlimited number of monomers. Dimers, trimers, and tetramers are non-limiting examples of oligomers.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

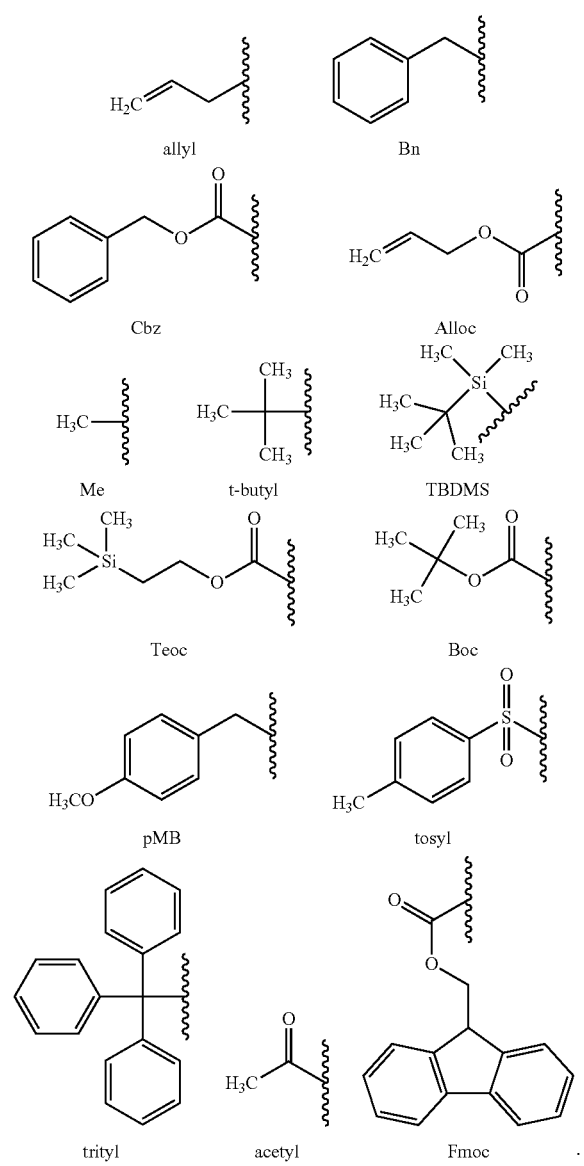

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

PAMAM Dendrimers Based CEST Contrast Agents

PAMAMs have emerged as versatile nanoplatforms for development of drug delivery vehicles and molecular imaging agents due to their useful properties such as, distinct size, low polydispersity, large number of reactive terminal groups, bulky interior void volume, biocompatibility and easy modification. In addition to well-defined structure, PAMAM dendrimers resemble branched-polypeptides/proteins since they are composed of ethylene units connected to each other via altering amide and tertiary amines (as presented FIG. 1A), and are available in generations G 0-10. These dendrimers have been extensively studied in combination with fluorescent dyes for optical/microscopic imaging and chelated Gd(III) for magnetic resonance.

CEST imaging is a novel MRI technique contrast mechanism that is well-suited for molecular imaging. CEST has several benefits compared to other MRI methods such as lower toxicity due to the absence of lanthanide metals, ease of modification, and clearance through breakdown during natural biochemical processes. However, currently reported organic CEST agents exhibit fast clearance and/or low sensitivity. There are many challenges with respect to detecting CEST contrast agents, such as insignificant difference in chemical shift of exchangeable protons and water, low spatial/temporal resolution, artifacts, and low contrast-noise-ratio. Some of these obstacles can be overcome by conjugating large number of low molecular weight CEST contrast agents/molecules with high molecular weight macromolecule such as dendrimer. Specifically, it has been discovered that a derivative of salicylic acid (SA) when conjugated to different generations (e.g. 1, 2, 3, 4, 5, 6 and so on) of poly(amidoamine) (PAMAM) dendrimers (FIG. 1A) via position 4 and 5 of the benzene ring on the derivative produces intense chemical exchange saturation transfer (CEST) contrast. These dendritic nanoplatforms with SA derivatives conjugated can be further modified using different terminal groups (FIG. 1B), including primary amine (G5-SA-D-Am), 1, 2-propanediol (G5-SA-D-Diol) and acetyl (G5-SA-D-Ac) (FIGS. 3A-F), which provide different surface properties to modify their pharmacokinetics while retaining strong CEST contrast. In addition, these dendrimer macromolecules can be also modified with polyethylene glycol residues, targeting moieties and other therapeutic agents and/or imaging modalities such as DOTA, which allows for their radiolabeling with transition metals ions including $^{111}$In or $^{64}$Cu and imaging using SPECT or PET, respectively or $^{177}$Lu for therapy (FIG. 1B). With such versatility, SA modified dendritic nanoplatforms represent a promising tool for various medical applications including monitoring delivery of therapeutics delivered using dendrimers and identifying sentinel lymph nodes for removal using sentinel lymph node biopsies.

Example 2

Material and Methods

General.

The G5-SA-D-Am, G5-SA-D-Diol and G5-SA-D-Ac dendrimers were synthesized using a commercially available generation 5 poly(amidoamine) ethylenediamine (EDA) core—dendrimer terminated with 128 primary amines (for short G5-Am), 1,4,7,10-tetraazacyclododecane-1,4,7,10-tetraacetic acid mono (N-hydroxysuccinimide ester) (D) and 5-aminomethylsalicylic acid methyl ester (SA), glycidol and acetic anhydride.

Chemicals.

All chemicals were purchased from Sigma-Aldrich or Fisher Scientific unless otherwise specified. Diisopropylethylamine (DIPEA), N-(3-Dimethylaminopropyl)-N'-ethylcarbodiimide hydrochloride (EDC) and 1-hydroxybenzotriazole (HOBt) were purchased from Chem Impex International Inc. 5-aminomethylsalicylic acid methyl ester (SA-ME) was acquired from Astatech Inc. All reagents and solvents were used as received without further purification.

Synthesis of 5-N-succinamylmethylsalicylic Acid Methyl Ester

5-N-succinamylmethylsalicylic acid methyl ester (SA-ME) was synthetized several times using the same procedure. 0.15 g of 5-aminomethylsalicylic acid methyl ester was ($6.89 \times 10^{-4}$ mole) was dissolved in 10 mL of dimethylformamide (DMF), followed by addition of 1.2 mole equivalent of 4-dimethylaminopyridine (DMAP, 0.101 g) and succinic anhydride (0.083 g). After 16 hours of stirring the reaction mixture at room temperature DMF was removed on a rotary evaporator. Obtained residue was dissolved in 50% water-methanol solution and purified on a reversed phase-high performance liquid chromatography (RP-HPLC) system (Varian ProStar) with an Agilent Technology 1260 Infinity photodiode array detector using a semipreparative C-18 Luna column (5 mm, 10×250 mm Phenomenex) and a gradient elution starting with 98% $H_2O$ (0.1% TFA) and 2% MeOH (0.1% TFA) reaching 100% of MeOH in 60 min at a flow rate of 4 mL/min. The desired 5-N-succinamylmethylsalicylic acid methyl ester (for short: SA-ME) was collected between 28 and 31 min (FIG. 4), evaporated on a rotary evaporator and dried for several hours under high vacuum, which resulted in white powder. Typical reaction yield was about 91%.

Nuclear Magnetic Resonance (NMR).

All NMR spectra were recorded using a Bruker Avance III 500 MHz NMR spectrometer using DMSO or $D_2O$ as solvents.

Synthesis of G5-SA-D-Ac, G5-SA-D-Diol and G5-SA-D-Ac.

Preparation of G5-SA-D-Ac, G5-SA-D-Diol and G5-SA-D-Ac involved multiple step synthesis as presented in FIGS. 3A-F. (step 1) 0.15 g of SA-ME was dissolved in DMF followed by addition of 2 mole equivalent of N-(3-dimethylaminopropyl)-N'-ethylcarbodiimide hydrochloride (EDC) and 1-hydroxybenzotriazole (HOBt) to activate the carboxyl group. After 30 min DMSO containing 0.02 mole equivalents of G5-Am (Molecular weight (MW)=28826, terminated with 128 $NH_2$ groups, dendrimer:SA-ME molar ratio 1:50) was added. Resulting reaction mixture was stirred at room temperature for 16 h and solvent was removed on a rotary evaporator. The residue was re-suspended in 1×PBS buffer (pH=7.4) and transferred to 15 mL Amicon centrifugal filters with 10 kDa Molecular weight cut-off (MWCO). After centrifugation for 30 minutes at 4100 rpm, 1×PBS buffer was added to re-dissolve the material. This process was repeated twice with PBS buffer and 6 times of deionized (DI) water. Purified product was dissolved in DI water and lyophilizes to give G5-SAME-Am. (step 2) Subsequently G5-SAME-Am was reacted with 4 mole equivalent DOTA-NHS in DMSO in the presence of DIPEA for 3 h, which was followed by evaporation of the solvent and purification as described above, providing G5-SAME-D-Am. In the next steps (step 4 and 5) G5-SAME-D-Am was allowed to react with 10 mole equivalent (on the basis of remaining terminal $NH_2$ groups) of either glycidol or acetic anhydride in methanol for 24 h to provide G5-SAME-D-Diol and G5-SA-D-Ac, respectively. Finally (step 3, 5, 7) carboxyl groups of salicylic acid moieties were deprotected (removal of methyl ester—ME) by dissolving obtained conjugates in 2 M NaOH 50% methanolic solution and stirring for 6 h at room temperature. Resulting solutions were diluted with DI $H_2O$ and extensively dialyzed against DI water using regenerated cellulose membrane with 10 kDa MWCO. The retentates were filtered, excess of $H_2O$ evaporated and lyophilized.

Matrix-Assisted Laser Desorption Ionization-Time-of-Flight (MALDI-TOF).

Spectra of dendritic nanomaterials were recorded on a Voyager DE-STR spectrophotometer, using 2,5-dihydroxybenzoic acid (DHB) as a matrix. First 10 µL of matrix at concentration of 10 mg/mL was mixed with 10 µL of dendrimer or conjugate at concentration of 4 mg/mL. Then 1 µL of resulting mixture was placed on the target plate (in triplicate) and evaporated. Matrix and dendrimer were dissolved in 50% MeOH and 0.1% TFA aqueous solution. Number of shots and laser power was adjusted according to spectrum quality.

Dynamic Light Scattering (DLS) and Zeta Potential.

Dynamic light scattering and zeta potential analyses were performed using a Malvern Zetasizer Nano ZEN3600. Results are presented as a mean of three sequential measurements, which confirmed satisfying reproducibility. All the analyzed conjugates were prepared at a concentration of 2 mg/ml in PBS (c=0.011M, pH 7.4). DLS measurements were performed at a 90° scattering angle at 25° C.

UV-Vis Spectroscopy.

UV-Vis spectra were collected on a NanoDrop 2000 spectrophotometer. The concentration of SA-ME, DOTA-NHS, G5-Am, G5-SA-D-Am were adjusted to the intensity of the observed peaks to stay within measurable range. Samples of dendrimer, conjugates and DOTA-NHS were prepared in PBS (c=0.1M, pH 7.4) and were titrated with an aqueous solution of $CuCl_2$ at a concentration to achieve appropriate molar ratios.

In Vitro MRI Measurements.

MR data of dendrimer conjugate solutions (concentration of 360 µM dendrimer conjugate in 1×PBS; 42 salicylic acid residues per one dendrimer molecule give the concentration about 15 mM, pH 7.2-7.5) were acquired on an 11.7 T Bruker Avance system (Bruker Biosciences, Billerica, Mass., USA) using a 20 mm birdcage transmit/receive coil. The QUESP dataset was acquired using saturation pulses with $B_1$=1.2, 2.4, 3.6, 4.7, 5.9, 7.2 and 10.8 µT, $T_{sat}$=4 s followed by a rapid acquisition with relaxation enhancement (RARE) readout (RARE=8, repetition time/echo time (TR/

TE)=6000 ms/19.09 ms). Saturation offsets were incremented from −12 to +12 ppm with a 0.2 ppm step size for the MTR$_{asym}$ spectra.

Calculation of Exchange Rate Constants Using QUESP Method.

Figure 14A:
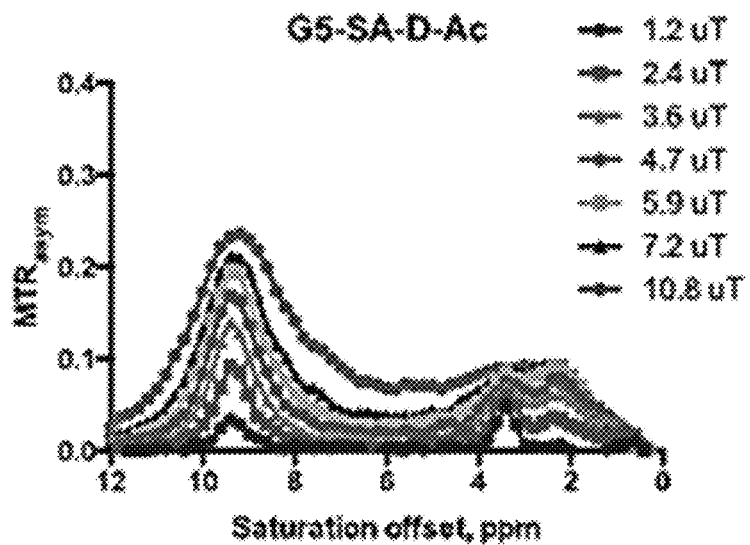
Figure 14B:
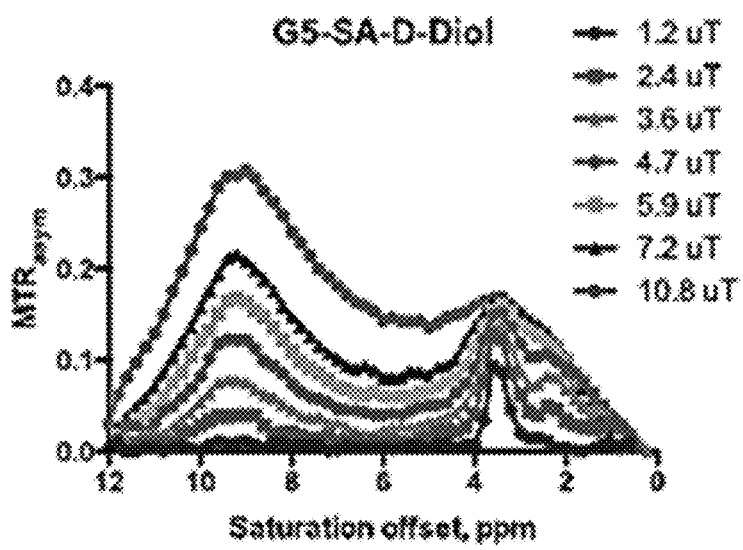
Figure 14C:
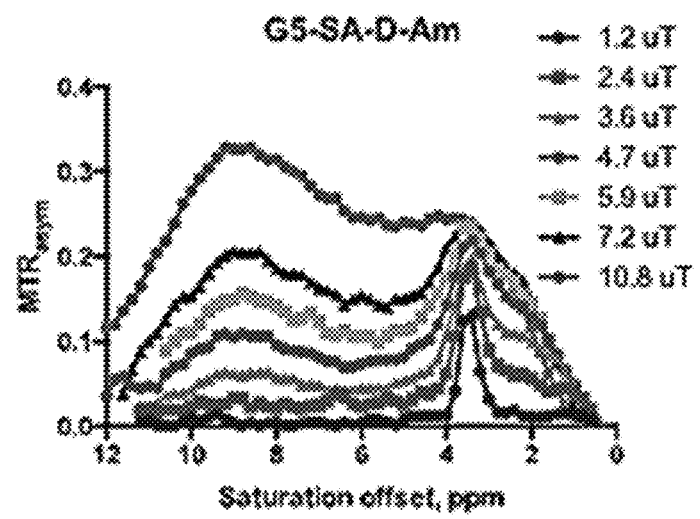
Figure 14D:
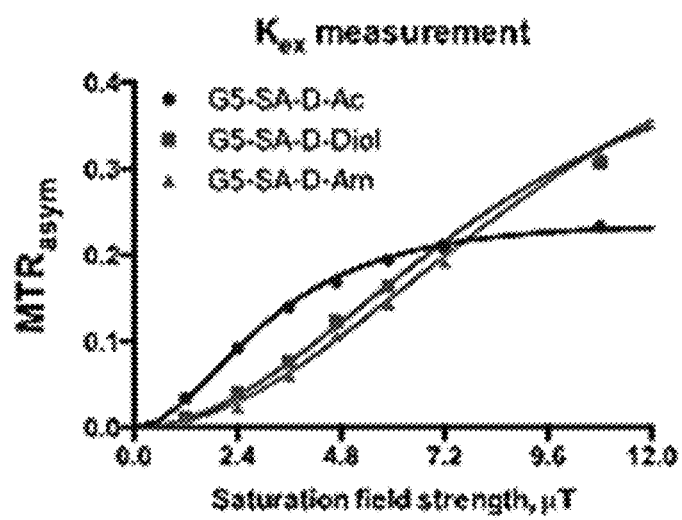
Figure 14E:
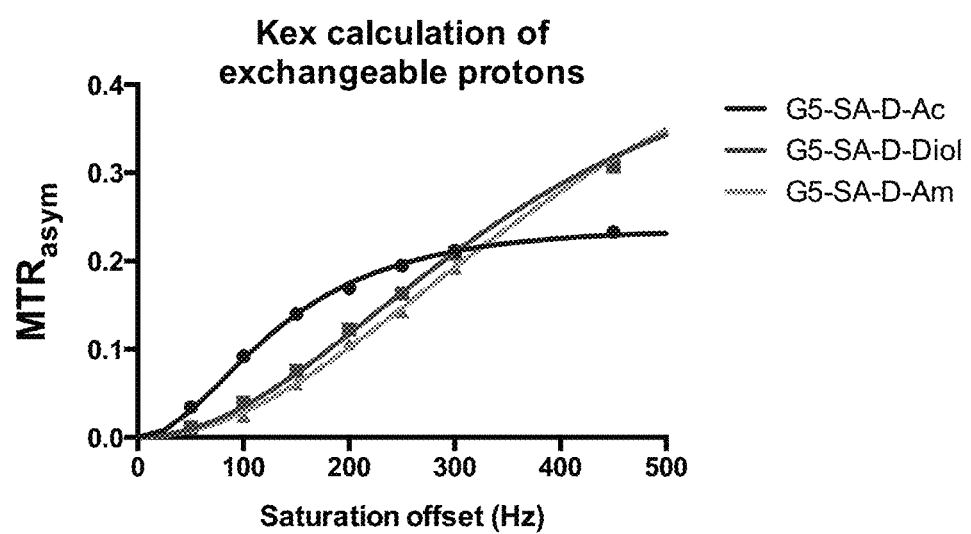

QUESP data were collected using a modified RARE sequence as described above with the saturation field strength varied while the saturation time was held constant and fit as described in McMahon M T et al. 2006 and plotted as MTRasym vs Saturation offset (Hz) (FIG. 14E). The TR was 6 s and TE was 19 ms.

$$PTR = \frac{S_{0w} - S_w(t_{sat}, \alpha)}{S_{0w}} = \frac{k_{sw} \cdot \alpha \cdot x_{CA}}{R_{1w} + k_{sw} \cdot x_{CA}}$$

$$\times [1 - e^{-(R_{1w} + k_{sw} \cdot x_{CA})t_{sat}}]$$

The resulting data was fit to numerical solutions to a 4 pool set of Bloch equations which includes phenolic protons (pool 1, Δω=9.4 ppm), dendrimer amine protons (pool 2, Δω=3.6 ppm; pool 3, Δω=2.2 ppm) and water (pool w, Δω=0 ppm). The Bloch equations were solved numerically using home written Matlab code to fit the data as described in detail previously to obtain the three exchange rates: $k_{1w}$, $k_{2w}$, $k_{3w}$ where $k_{1w}$=rate of exchange for proton 1 (phenolic proton) with water (Yang et al., 2014). The longitudinal ($R_1$) and transverse ($R_2$) relaxation parameters were fixed to $R_{1w}$=0.3 s$^{-1}$, $R_{2w}$=0.9 s$^{-1}$, $R_{11}$=$R_{12}$=$R_{13}$=0.71 s$^{-1}$, and $R_{21}$=$R_{22}$=$R_{23}$=39 s$^{-1}$.

TABLE 1

Exchange rates obtained from fitting QUESP data

| G5 | Dw = 9.4 ppm $k_{1w}$ [s$^{-1}$] | Dw = 3.6 ppm $k_{2w}$ [s$^{-1}$] | Dw = 2.2 ppm $k_{3w}$ [s$^{-1}$] |
|---|---|---|---|
| 1 | N/A | N/A | N/A |
| 2 | 4500 | 1000 | 100 |
| 3 | 3600 | 470 | 150 |
| 4 | 950 | 210 | 210 |

Implantation of U87 Glioblastoma Cells into Mouse Brain.

U87 glioblastoma cells (ATCC, Manassas, Va.) were maintained in monolayer culture (37° C., 5% $CO_2$, 95% $O_2$) in minimum essential medium (MEM) with Eagle's salts supplemented with 10% fetal bovine serum, penicillin, and streptomycin (Gibco, Grand Island, N.Y.). Cells were subcultured and used for implantation when they were in an exponential phase of growth. The suspension was diluted with PBS to a final concentration of 20000 cells per μL. A total of 3 SCID mice (20-25 g) obtained from the National Cancer Institute (Frederick, Md.), were anesthetized with ketamine (80 mg·kg-1) and xylazine (13 mg·kg-1) administered intraperitoneally (i.p.). They were placed in a stereotactic apparatus, and after the skull was exposed, and a 0.7 mm burr hole was drilled over the right hemisphere 2.0 mm lateral to the midline and 1.0 mm anterior to the bregma. The needle of a 10 μL Hamilton syringe was inserted to a depth of 2.5 mm beneath the dura through the center of the skull hole and 10$^5$ U87 cells in 5 μL PBS were injected intracerebrally during a 10 min. The incision was closed with 4-0 silk sutures (Ethicon, Somerville, N.J.).

In Vivo MRI Measurements.

Mice bearing U87 cell derived glioblastoma xenografts were anesthetized prior to intracranial infusion of 5 μl of G5-SA-D-Ac at a concentration of 50 mg/ml over 10 min. The animals were then positioned in an 11.7 T horizontal bore Bruker Biospec scanner (Bruker Biosciences, Billerica, Mass.) and were under isoflurane anesthesia for the entire image collection period. Images were acquired from 0.5-1.5 hours after intracranial injection. To produce the CEST images, two sets of saturation images were collected, a WASSR set for $B_0$ mapping and a CEST data set for characterizing contrast. For the WASSR images, the saturation parameters were $t_{sat}$=500 ms, $B_1$=0.5 μT, TR=1.5 sec with saturation offset incremented from −1 to +1 ppm with respect to water in 0.1 ppm steps, while for the CEST images, $t_{sat}$=2.2 sec, $B_1$=3.4 μT, TR=5.5 sec, with offset sampling from −7.8 to −10.8 ppm and +7.8 to +10.8 ppm with a 0.3 ppm step. The acquisition parameters were: TE=4.8 ms, RARE factor=12-16. The CEST contrast was calculated as MTR$_{asym}$ according to:

$$MTR_{asym} = \frac{S_w(\Delta w) - S_w(+\Delta w)}{S_{0w}}$$

For all in vivo images, the average MTR$_{asym}$ from 8.7 to 9.9 ppm was calculated. The signal intensity data (SW) was processed using Matlab 2015 and Prism 6 software.

In order to determine the tumor coverage shown in FIG. 18B, tumor borders were defined according to $T_{2w}$ images, regions of interest (ROI's) were drawn over this region and histograms of the average MTR$_{asym}$ from 8.7 to 9.9 ppm prepared. Percent coverage was then calculated by number (#) of pixels above −0.035/total # of tumor pixels.

Example 3

Results

Without wishing to be bond to any one particular theory, it was thought that the high spatial resolution and functional aspects of CEST MR could be used to noninvasively image the distribution of nanoparticles within brain tumors. As dendrimers have emerged as a versatile platform for drug and gene delivery (Caminade and Turin, 2014; Somani and Dufes, 2014) and proven useful for delivering therapeutics to brain tumors via CED (Yang et al., 2009; Agrawal et al., 2009; Yang et al., 2008), CEST MR has been used herein to investigate dendrimer distribution after CED to brain tumors. In order to accomplish this, SA conjugated dendrimers with different functional end groups have been prepared and their capabilities in vivo in mice bearing U87 glioblastoma xenografts have been evaluated. To perform this proof of concept study, poly(amidoamine) (PAMAM) dendrimers (Esfand and Tomalia, 2001) have been utilized, which have been extensively studied in combination with radionuclides (Almutairi et al., 2009; Zhang et al., 2010), fluorescent dyes (Kobayashi et al., 2007), Gd(III) chelates (Villaraza et al., 2010; Opina et al., 2015) and therapeutics (Menjoge, 2010). For the synthesis of a series of diamagnetic dendrimers, a large number of SA that will allow for CEST MR detection have been conjugated.

5-aminomethyl SA has been selected as a CEST contrast agent to conjugate to dendrimers because of its near optimal exchange rate for detection on 3T scanners, commercial availability and price. SA was conjugated to generation 5 amine terminated dendrimer with 128 terminal $NH_2$ groups that can be readily modified and possesses favorable fast renal clearance due to its about 5 nm size (Villazara et al., 2010). The changes in dendrimer solubility following SA conjugation were first investigated. Dendrimers with different number of SA: G5-SA42, G5-SA50 and G5-SA60 were prepared through changing the molar ratio for conjugation and allowing for sufficient SA concentration for MR detection. Of these, only G5-SA42-dendrimer showed suitable solubility in PBS to achieve 360 µM that is required for MR detection. Using fully amine terminated G5-Am as a parent dendrimer, 42 moieties of SA-ME were conjugated, four DOTA molecules (D), for radiolabeling and future PET/MR studies) were conjugated, and remaining terminal primary amines were capped with acetyl or 1,2-propanediol functionalities to modulate surface properties (FIGS. 3A-F). To evaluate how surface properties influence the physiochemical and biological features of the CEST agents three dendritic nanoplatforms were synthesized. The G5-SA-D-Am, G5-SA-D-Diol and G5-SA-D-Ac were synthesized using commercially available generation (5) poly(amidoamine) (PAMAM) ethylenediamine (EDA) core—dendrimer terminated with 128 primary amines (for short G5-Am), 1,4,7,10-tetraazacyclododecane-1,4,7,10-tetraacetic acid mono (N-hydroxysuccinimide ester) (DOTA-NHS, D) and 5-aminomethylsalicylic acid methyl ester (SAME). To covalently attach SA to the dendrimer it was carboxylated by reacting with succinic anhydride in dimethylformamide in the presence of diisopropylethylamine (DIPEA) and 4-dimethylaminopyridine (DMAP) according to reaction scheme disclosed in FIGS. 3A-F. To confirm modifications and measure number of conjugated moieties, starting dendrimer, intermediate conjugates and final products were characterized by $^1$HNMR spectroscopy and MALDI mass spectrometry. Results are collected in Table 2. $^1$HNMR and MALDI-MS were in good agreement showing signals related to attached functional groups and change in average molecular weight upon each reaction step.

Without wishing to be bound to any one particular theory, it was thought that different terminal groups of dendrimers will have different surface properties and will impact the exchange rates (k's). An additional advantage is a reduced overall positive charge that contributes to toxicity observed with dendrimers (Shaw et al., 1993; Stroom et al., 1999). The 3 G5 based nanoparticles shown in FIGS. 3A-F (360 µsolutions, about 15 mM in SA residues) were then tested for CEST MRI contrast properties. Exchangeable protons present on these nanoplatforms include surface phenols, surface amines and surface glycidols and interior tertiary/secondary amines. Saturation transfer spectra were acquired as a function of saturation power to measure the k's for these compounds. As expected, all 3 dendrimer conjugates produced frequency-dependent CEST contrast with a main peak at 9.4 ppm and additional peaks at 3.6 ppm and 2.2 ppm from water which increased for stronger saturation pulses (FIG. 14A, FIG. 14B, and FIG. 14C).

As is evident based on the breadth of the contrast peaks, the phenolic protons (9.4 ppm) exchange slowest in the G5-SA-D-Ac conjugate and fastest in the G5-SA-D-Am conjugate. To quantify this, the saturation power intensity data was fit as described previously (Yang et al., 2014; McMahon et al., 2006) and display the resulting fits in FIG. 14D and tabulate the exchange rates for the phenolic protons ($k_{1w}$) determined in Table 2. The phenolic protons in G5-SA-D-Ac had an over 4.5 times slower $k_{ex}$ compared to G5-SA-D-Am, 950 s$^{-1}$, and 4500 s$^{-1}$ respectively. This data demonstrates the inductive effects of the neighboring amines and hydroxyls on phenol exchange, which is similar to effects observed in peptides originally described by Molday and coworkers (Molday et al., 1972). Overall, the G5-SA-D-Ac dendrimer displayed the highest sensitivity for $_{\omega 1}$<5.9 µT and also the sharpest frequency dependence making it the most promising CEST agent for use on the 3T clinical scanners.

The size and zeta potential for these dendrimers that could impact in vivo distribution were also measured and these measurements were compared with unconjugated starting material (Table 2). The zeta potential values gradually decreased from +43.5 mV for G5-Am (fully amine terminated=starting dedrimer) to +22.03, +11.15 and −6.91 mV for G5-SA-D-Am, G5-SA-D-Diol and G5-SA-D-Ac, respectively.

TABLE 2

Physicochemical characteristics of initial and final G5 dendrimer based CEST nanoprobes.

| Dendrimer | MW [amu] | # of Am | # of SA | # of D | # of Diol | # of Ac | hdm [nm] | ζ [mV] | $k_{ex}$ [s$^{-1}$] for NH$_2$ | kex [s$^{-1}$] for SA |
|---|---|---|---|---|---|---|---|---|---|---|
| G5-Am | 25766 | 128 | — | — | — | — | 4.9 ± 0.1 | 43.5 ± 2 | N/A | N/A |
| G5-SA-D-Am | 37222 | 82 | 42 | 4 | — | — | 4.9 ± 0.3 | 22.0 ± 2 | 4500 | 4500 |
| G5-SA-D-Diol | 39652 | 42 | 42 | 4 | 40 | — | 4.9 ± 0.6 | 11.1 ± 1 | 3600 | 3600 |
| G5-SA-D-Ac | 40555 | 26 | 42 | 4 | — | 56 | 5.0 ± 0.1 | −6.9 ± 1 | 950 | 950 |

MW-molecular weight as measured by MALDI-TOF, #-number, Am-primary amine, SA salicylic acid, D-DOTA, Diol-1,2-propanediol, Ac-acetyl hdm-hydrodynamic diameter as determined by dynamic light scattering, ζ-zeta potential, $k_{ex}$ = exchange rate constant.

Based on these measurements, the G5-SA-D-Diol and G5-SA-D-Ac formulations are not fully capped even though a 10× molar excess of glycidol and acetic anhydride over the surface amines was used for the capping reactions. It is likely that steric hindrance imposed by SA and DOTA functional groups impedes the complete substitution of terminal amines. According to dynamic light scattering measurements, the size distributions for all G5 nanoplatforms remained narrow and centered around ~5 nm. Based on the CEST contrast being strongest using B1=0-6 µT, the sharpness of the frequency profile in the Z-spectra, and the zeta potential being the smallest, we chose the G5-SA-D-Ac formulation for in vivo.

To examine the distribution properties of G5-SA-D-Ac, CEST nanocarriers were delivered based on convection enhanced delivery (CED) (Bobo et al., 1994) which is efficient for delivery of both macromolecules and nanocarriers (Allard et al., 2009; Bidros et al., 2010; Zhou et al., 2012; Lonser et al., 2002) and involves pressurized infusion directly into a tumor. SCID mice were inoculated with U87 glioblastoma cells in right caudate putamen under stereotaxic control. The infusions of CEST nanocarriers were performed through the same site as the tumor inoculation site. These infusions were followed by CEST and $T_{2w}$ MRI. Representative images of average MTRasym from 8.7 to 9.9 ppm acquired pre-injection and at 30 and 60 minutes after injection of dendrimer are displayed in FIG. 15A, and representative images acquired pre-injection, at 0.5 h, 0.75 h, and 1 h after injection of dendrimer are displayed in FIG. 15B. CEST MR images show clear contrast after infusion.

The distribution of nanocarrier within tumors is an important factor to determine following CED. As seen in FIG. 18A, the distribution in average MTRasym values over the whole brain tumor was less than −0.035 prior to CED, but after injection there was a significant fraction of tumor pixels with elevated contrast. In addition, as shown in FIG. 16, the contrast persisted for 1.5 hours. As shown by the MRI data, the G5-SA-D-Diol dendrimer conjugate was also detected via CEST contrast within the tumor as long as after 1.5 hour upon intracranial injection (FIG. 17). Borrowing the concept of target coverage found in radiation therapy (Shaw et al., 1993; Stroom et al., 1999) and assuming all contrast greater than −0.035 is due to the CEST agent, 50% of the tumor pixels contain G5-SA-D-Ac dendrimer conjugate for n=3 mice (FIG. 18B). These measurements indicate that this dendrimer was well detected and widely dispersed within brain tumors using an infusion rate (0.5 μL/min) recommended for rodents and similar to those used in patients previously (Allard et al., 2009).

Example 4

Discussion

As shown by the data, a novel PAMAM dendrimer based diamagnetic nanoplatform which produces CEST MRI contrast has been prepared and tested. Previously, dendritic gadolinium and dysprosium chelates have been prepared as high sensitivity MRI agents and have displayed favorable pharmacokinetics for use as blood pool agents, lymphatic imaging agents, liver imaging agents and renal function agents (Kobayashi et al., 2005; Toth et al., 1996; Wiener et al., 1994; Bryant et al., 1999; Misselwitz et al., 2001; Bulte et al., 1998; Huang et al., 2012). The new SA based PAMAM dendrimers present additional advantages based on several features; the MRI contrast is produced through conjugating SA. SA is a metabolite of aspirin and has been used as an anti-inflammatory drug in patients (Needs et al., 1985; Bochner et al., 1981; Paterson et al., 2008). The low molecular weight of SA allows for conjugation of more molecules/dendrimer. In addition, conjugation of SA together with chemotherapeutics and tumor cell specific targeting (such as CXCR4) may allow for improved understanding of nanoparticle distribution within the tumors. While previously it has been demonstrated that dendrimers could be detected without modification using CEST MRI (McMahon et al., 2006), the sensitivity was modest. It is expected that dendrimers evaluated herein have the sensitivity to enable usage on clinical 3T scanners based on their larger shifts compared to other agents. Finally, the presence of DOTA on PAMAM dendrimers will allow for dual- or multi-modality PET/SPECT/MR imaging. The ability to non-invasively characterize nanoparticle tumor distribution may allow for design of nanotherapeutics with improved intratumoral diffusion properties.

In summary, SA-based nanocarriers which produce excellent characteristics as CEST agents, i.e. large chemical shift=9.4 ppm from water and exchange rates from 1000 to 4,500 s$^{-1}$, have been designed and synthesized. It has also been demonstrated that these are readily detected in vivo in mice bearing U87 glioblastoma brain tumors with stable contrast up to 1.5 hours after intracranial injection.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

International Patent Application Publication No. PCT/US2008/007947 to Pomper M G, Ray S, Mease R C, Foss C. for Labeled inhibitors of prostate specific membrane antigen (PSMA) biological evaluation, and use as imaging agents, published 2008 Dec. 31 (WO 2009002529 A2);

International Patent Application Publication No. PCT/US2008/013158 to Chandran S S, Ray S, Denmeade S R, Pomper M G, Mease R C for Prostate specific membrane antigen targeted nanoparticles for therapy of prostate cancer, published 2009 Jun. 4 (WO 2009070302 A1);

International Patent Application Publication No. PCT/US2010/028020 to Pomper M G, Mease R C.; Ray S, Chen Y. for PSMA-targeting compounds and uses thereof, published 2010 Sep. 23 (WO 2010108125 A2);

A. Agrawal, D. H. Min, N. Singh, H. H. Zhu, A. Birjiniuk, G. von Maltzahn, T. J. Harris, D. Y. Xing, S. D. Woolfenden, P. A. Sharp, A. Charest, S. Bhatia, ACS Nano 2009, 3, 2495-2504;

Aime, C. Carrera, D. Delli *Castelli*, S. Geninatti Crich, E. Terreno, Angew. Chem. Int. Ed. 2005, 44, 1813-1815;

E. Allard, C. Passirani, J. P. Benoit, Biomaterials 2009, 30, 2302-2318;

A. Almutairi, R. Rossin, M. Shokeen, A. Hagooly, A. Ananth, B. Capoccia, S. Guillaudeu, D. Abendschein, C. J. Anderson, M. J. Welch, J. M. J. Frechet, Proc Natl Acad Sci USA 2009, 106, 685-690;

A. Bar-Shir, G. S. Liu, Y. J. Liang, N. N. Yadav, M. T. McMahon, P. Walczak, S. Nimmagadda, M. G. Pomper, K. A. Tallman, M. M. Greenberg, P. C. M. van Zijl, J. W. M. Bulte, A. A. Gilad, J. Am. Chem. Soc. 2013, 135, 1617-1624;

A. Bar-Shir, G. Liu, K. W. Y. Chan, N. Oskolkov, X. Song, N. N. Yadav, P. Walczak, M. T. McMahon, P. C. M. van Zijl, J. W. M. Bulte, A. A. Gilad, Acs Chemical Biology 2013, 9, 134-138;

M. E. Bartolini, J. Pekar, D. R. Chettle, F. McNeill, A. Scott, J. Sykes, F. S. Prato, G. R. Moran, Magnetic resonance imaging 2003, 21, 541-544;

D. S. Bidros, J. K. Liu, M. A. Vogelbaum, Future oncology 2010, 6, 117-125;

R. H. Bobo, D. W. Laske, A. Akbasak, P. F. Morrison, R. L. Dedrick, E. H. Oldfield, Proc Natl Acad Sci USA 1994, 91, 2076-2080;

F. Bochner, G. G. Graham, B. E. Cham, D. M. Imhoff, T. M. Haavisto, Clin. Pharmacol. Ther. 1981, 30, 266-275;

L. H. Bryant, M. W. Brechbiel, C. C. Wu, J. W. M. Bulte, V. Herynek, J. A. Frank, JMRI-J. Magn. Reson. Imaging 1999, 9, 348-352;

J. W. M. Bulte, C. C. Wu, M. W. Brechbiel, R. A. Brooks, J. Vymazal, M. Holla, J. A. Frank, Invest. Radiol. 1998, 33, 841-845;

A. M. Caminade, C. O. Turrin, J. Mat. Chem. B 2014, 2, 4055-4066;

K. W. Chan, T. Yu, Y. Qiao, Q. Liu, M. Yang, H. Patel, G. Liu, K. W. Kinzler, B. Vogelstein, J. W. Bulte, P. C. van Zijl, J. Hanes, S. Zhou, M. T. McMahon, Journal of controlled release 2014, 180, 51-59;

K. W. Chan, J. W. Bulte, M. T. McMahon, Wiley interdisciplinary reviews. Nanomedicine and nanobiotechnology 2014, 6, 111-124;

K. W. Y. Chan, M. T. McMahon, Y. Kato, G. Liu, J. W. M. Bulte, Z. M. Bhujwalla, D. Artemov, P. C. M. van Zijl, Magnetic Resonance in Medicine 2012, 68, 1764-1773;

K. W. Chan, G. Liu, X. Song, H. Kim, T. Yu, D. R. Arifin, A. A. Gilad, J. Hanes, P. Walczak, P. C. M. van Zijl, J. W. Bulte, M. T. McMahon, Nature materials 2013, 12, 268-275;

L. Q. Chen, C. M. Howison, J. J. Jeffery, I. F. Robey, P. H. Kuo, M. D. Pagel, Magnetic Resonance in Medicine 2014, 72, 1408-1417;

R. Esfand, D. A. Tomalia, Drug discovery today 2001, 6, 427-436;

C. T. Farrar, J. S. Buhrman, G. S. Liu, A. Kleijn, M. L. M. Lamfers, M. T. McMahon, A. A. Gilad, G. Fulci, Radiology 2015, 275, 746-754;

A. A. Gilad, M. T. McMahon, P. Walczak, P. T. Winnard, V. Raman, H. W. M. van Laarhoven, C. M. Skoglund, J. W. M. Bulte, P. C. M. van Zijl, Nat. Biotechnol. 2007, 25, 217-219; dJ. Y. Zhou, B. Lal, D. A. Wilson, J. Laterra, P. C. M. van Zijl, Magnetic Resonance in Medicine 2003, 50, 1120-1126;

C. H. Huang, K. Nwe, A. Al Zaki, M. W. Brechbiel, A. Tsourkas, ACS Nano 2012, 6, 9416-9424;

Hyman et al. (Coordination Chemistry Reviews, 256 (2012), 2333-2356);

Kannan R M, Nance E, Kannan S, Tomalia D A. Emerging concepts in dendrimer-based nanomedicine: from design principles to clinical applications. J Intern Med. 2014; 276(6):579-617;

H. Kobayashi, M. W. Brechbiel, Adv. Drug Deliv. Rev. 2005, 57, 2271-2286;

H. Kobayashi, Y. Koyama, T. Barrett, Y. Hama, C. A. S. Regino, I. S. Shin, B. S. Jang, N. Le, C. H. Paik, P. L. Choyke, Y. Urano, ACS Nano 2007, 1, 258-264;

F. Kogan, A. Singh, C. Debrosse, M. Hans, K. Cai, R. P. Nanga, M. Elliott, H. Hariharan, R. Reddy, Neuroimage 2013, 77, 262-267;

F. Kogan, M. Haris, A. Singh, K. Cai, C. Debrosse, R. P. Nanga, H. Hariharan, R. Reddy, Magnetic resonance in medicine: official journal of the Society of Magnetic Resonance in Medicine/Society of Magnetic Resonance in Medicine 2013;

W. Ling, R. R. Regatte, G. Navon, A. Jerschow, Proc Natl Acad Sci USA 2008, 105, 2266-2270;

G. Liu, M. Moake, Y. E. Har-el, C. M. Long, K. W. Chan, A. Cardona, M. Jamil, P. Walczak, A. A. Gilad, G. Sgouros, P. C. van Zijl, J. W. Bulte, M. T. McMahon, Magnetic resonance in medicine: official journal of the Society of Magnetic Resonance in Medicine/Society of Magnetic Resonance in Medicine 2012, 67, 1106-1113;

G. Liu, X. Song, K. W. Y. Chan, M. T. McMahon, "Nuts and Bolts of CEST Imaging", NMR in Biomed. 2013, Doi: 10.1002/nbm.2899;

G. Liu, A. A. Gilad, J. W. M. Bulte, P. C. M. van Zijl, M. T. McMahon. High-Throughput Screening of Chemical Exchange Saturation Transfer MR Contrast Agents. Con. Media. & Mol. Imag. 2010; 5(3): 162-170;

Longo D L, Dastru W, Digilio G, Keupp J, Langereis S, Lanzardo S, Prestigio S, Steinbach O, Terreno E, Uggeri F, Aime S. Iopamidol as a responsive MRI-chemical exchange saturation transfer contrast agent for pH mapping of kidneys: In vivo studies in mice at 7 T. Magn Reson Med 2011; 65(1):202-211;

D. L. Longo, A. Busato, S. Lanzardo, F. Antico, S. Aime, Magnetic Resonance in Medicine 2013, 70, 859-864;

R. R. Lonser, S. Walbridge, K. Garmestani, J. A. Butman, H. A. Walters, A. O. Vortmeyer, P. F. Morrison, M. W. Brechbiel, E. H. Oldfield, Journal of neurosurgery 2002, 97, 905-913;

Michael T. McMahon, Assaf A. Gilad, Jinyuan Zhou, Phillip Z. Sun, Jeff W. M. Bulte, Peter C. M. van Zijl. Quantifying Exchange Rates in Chemical Exchange Saturation Transfer Agents Using the Saturation Time and Saturation Power Dependencies of the Magnetization Transfer Effect on the Magnetic Resonance Imaging Signal (QUEST and QUESP): pH Calibration for Poly-L-Lysine and a Starburst Dendrimer. Magn Reson Med 2006; 55(4): 836-847;

M. T. McMahon, A. A. Gilad, M. A. DeLiso, S. M. Berman, J. W. Bulte, P. C. van Zijl, Magnetic resonance in medicine: official journal of the Society of Magnetic Resonance in Medicine/Society of Magnetic Resonance in Medicine 2008, 60, 803-812;

M. T. McMahon, A. A. Gilad, J. Zhou, P. Z. Sun, J. W. Bulte, P. C. van Zijl, Magnetic resonance in medicine: official journal of the Society of Magnetic Resonance in Medicine/Society of Magnetic Resonance in Medicine 2006, 55, 836-847;

A. R. Menjoge, R. M. Kannan, D. A. Tomalia, Drug discovery today 2010, 15, 171-185;

B. Misselwitz, H. Schmitt-Willich, W. Ebert, T. Frenzel, H. J. Weinmann, Magn. Reson. Mat. Phys. Biol. Med. 2001, 12, 128-134;

R. S. Molday, Englander, S. W., Kallen, R. G., Biochemistry 1972, 11, 150-158;

C. J. Needs, P. M. Brooks, Clin. Pharmacokinet. 1985, 10, 164-177;

A. C. Opina, K. J. Wong, G. L. Griffiths, B. I. Turkbey, M. Bernardo, T. Nakajima, H. Kobayashi, P. L. Choyke, O. Vasalatiy, Nanomedicine (Lond) 2015, 10, 1423-1437;

J. R. Paterson, G. Baxter, J. S. Dreyer, J. M. Halket, R. Flynn, J. R. Lawrence, Journal of agricultural and food chemistry 2008, 56, 11648-11652;

Que et al. (Chem Soc. Rev. 2010, 39, 51-60);

M. Rivlin, I. Tsarfaty, G. Navon, Magnetic Resonance in Medicine 2014, 72, 1375-1380; T. Jin, H. Mehrens, K. S. Hendrich, S. G. Kim, J. Cereb. Blood Flow Metab. 2014, 34, 1402-1410;

E. Shaw, R. Kline, M. Gillin, L. Souhami, A. Hirschfeld, R. Dinapoli, L. Martin, International journal of radiation oncology, biology, physics 1993, 27, 1231-1239;

Sherry A D, Woods M. Chemical exchange saturation transfer contrast agents for magnetic resonance imaging. Annual Review of Biomedical Engineering 2008; 10:391-411;

S. Somani, C. Dufes, Nanomedicine 2014, 9, 2403-2414;

X. Song, R. D. Airan, D. R. Arifin, A. Bar-Shir, D. K. Kadayakkara, G. Liu, A. A. Gilad, P. C. van Zijl, M. T. McMahon, J. W. Bulte, Nat Commun 2015, 6, 6719;

J. C. Stroom, H. C. de Boer, H. Huizenga, A. G. Visser, International journal of radiation oncology, biology, physics 1999, 43, 905-919;

P. Z. Sun, T. Benner, A. Kumar, A. G. Sorensen, Magnetic Resonance in Medicine 2008, 60, 834-841;

A. A. Thomas, C. W. Brennan, L. M. DeAngelis, A. M. Omuro, JAMA Neurol. 2014, 71, 1437-1444;

E. Toth, D. Pubanz, S. Vauthey, L. Helm, A. E. Merbach, Chem.-Eur. J. 1996, 2, 1607-1615;

P. C. van Zijl, C. K. Jones, J. Ren, C. R. Malloy, A. D. Sherry, Proc Natl Acad Sci USA 2007, 104, 4359-4364;

van Zijl P. C., Yadav N. N. Chemical exchange saturation transfer (CEST): what is in a name and what isn't? Magn Reson Med 2011; 65(4):927-948;

A. J. L. Villaraza, A. Bumb, M. W. Brechbiel, Chem. Rev. 2010, 110, 2921-2959;

S. Walker-Samuel, R. Ramasawmy, F. Torrealdea, M. Rega, V. Rajkumar, S. P. Johnson, S. Richardson, M. Goncalves, H. G. Parkes, E. Arstad, D. L. Thomas, R. B. Pedley, M. F. Lythgoe, X. Golay, Nat. Med. 2013, 19, 1067-1072;

G. F. Woodworth, G. P. Dunn, E. A. Nance, J. Hanes, H. Brem, Frontiers in Oncology 2014, 4, 126;

X. Yang, X. Song, Y. Li, G. Liu, S. Ray Banerjee, M. G. Pomper, M. T. McMahon, Angewandte Chemie 2013, 52, 8116-8119;

X. Yang, N. N. Yadav, X. Song, S. Ray Banerjee, H. Edelman, I. Minn, P. C. van Zijl, M. G. Pomper, M. T. McMahon, Chemistry 2014, 20, 15824-15832;

W. L. Yang, R. F. Barth, G. Wu, T. Y. Huo, W. Tjarks, M. Ciesielski, R. A. Fenstermaker, B. D. Ross, C. J. Wikstrand, K. J. Riley, P. J. Binns, J. Neuro-Oncol. 2009, 95, 355-365;

W. L. Yang, G. Wu, R. F. Barth, M. R. Swindall, A. K. Bandyopadhyaya, W. Tjarks, K. Tordoff, M. Moeschberger, T. J. Sferra, P. J. Binns, K. J. Riley, M. J. Ciesielski, R. A. Fenstermaker, C. J. Wikstrand, Clin. Cancer Res. 2008, 14, 883-891;

Yang, X., et al. Tuning phenols with Intra-Molecular bond Shifted Hydrogens (IM-SHY) as diaCEST MRI contrast agents. Chemistry 20, 15824-15832 (2014);

Yang X, Song X, Li Y, Liu G, Banerjee S R, Pomper M G, McMahon M T. Salicylic acid and analogues as diaCEST MRI contrast agents with highly shifted exchangeable proton frequencies. Angew Chem Int Ed Engl. 2013; 52:8116-19;

E. C. Wiener, M. W. Brechbiel, H. Brothers, R. L. Magin, O. A. Gansow, D. A. Tomalia, P. C. Lauterbur, Magnetic Resonance in Medicine 1994, 31, 1-8;

Y. Q. Zhang, Y. H. Sun, X. P. Xu, H. Zhu, L. L. Huang, X. Z. Zhang, Y. J. Qi, Y. M. Shen, Bioorg. Med. Chem. Lett. 2010, 20, 927-931;

J. Zhou, K. B. Atsina, B. T. Himes, G. W. Strohbehn, W. M. Saltzman, Cancer journal 2012, 18, 89-99.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I):

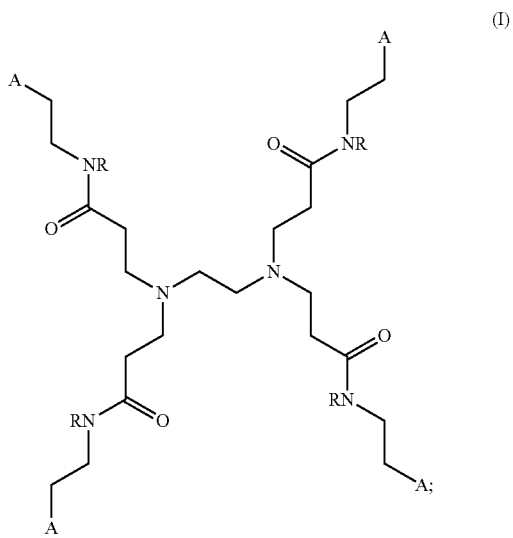

wherein:

each A is

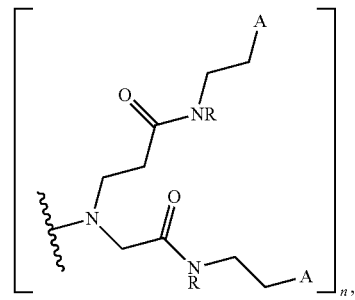

wherein each A' is independently selected from the group consisting of

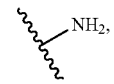

(Am)

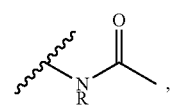

(Ac)

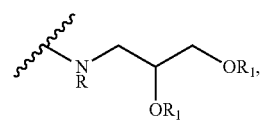

(PP)

a metal chelating moiety (D) optionally comprising a metal or a radiometal suitable for treating or imaging, a therapeutic agent (T), a targeting agent (TG), an imaging agent (IM), PEG-X wherein PEG is polyethylene glycol and X is

or a targeting agent (TG), and —NR-L-W—$(CH_2)_m$-SA, provided that at least one of A' is —NR-L-W—$(CH_2)_m$-SA, L is a linking group selected from the group consisting of —$(CH_2)_m$—, —C(=O)—$(CH_2)_m$—, —$(CH_2$—$CH_2$—O$)_t$—, —C(=O)—$(CH_2$—$CH_2$—O$)_t$—, —(O—$CH_2$—$CH_2)_t$—, —C(=O)—(O—$CH_2$—$CH_2)_t$—, —C(=O)—$(CHR_2)_m$—$NR_3$—C(=O)—$(CH_2)_m$—, —C(=O)—$(CH_2)_m$—O—C(=O)—$NR_3$—$(CH_2)_p$—, —C(=O)—$(CH_2)_m$—$NR_3$—C(=O)—O—$CH_2)_p$—, —C(=O)—$(CH_2)_m$—$NR_3$—C(=O)—$NR_3$—$(CH_2)_p$—, —C(=O)—$(CH_2)_m$—$NR_3$—C(=O)—$(CH_2)_p$—, —C(=O)—$(CH_2)_m$—C(=O)—$NR_3$—$(CH_2)_p$—, —C(=O)—$(CH_2)_m$—$NR_3$—C(=O)—$NR_3$—$(CH_2)_p$—, —C(=O)—$(CH_2)_m$—$NR_1$—C(=O)—$NR_3$—$(CH_2)_p$—, —C(=O)—$(CH_2)_m$—O—C(=O)—$NR_3$—, —C(=O)—$CH_2$—O—C(=O)—$NR_3$—$(CH_2)_p$—, —C(=O)—$(CH_2)_m$—$NR_3$—C(=O)—O—$(CH_2)_p$—, polyethylene glycol, glutaric anhydride, albumin, lysine, and amino-acid, W is selected from the group consisting of —NR—C(=O)—, —C(=O)—NR—, —S—, —O—, and —$SO_2$—;

SA is

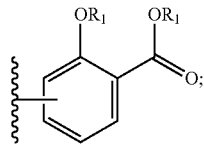

each R is independently selected from the group consisting of H and $C_1$-$C_4$ alkyl;

each $R_1$ is independently selected from the group consisting of H, Na, $C_1$-$C_4$ alkyl, and a protecting group;

each $R_2$ is independently selected from the group consisting of hydrogen, and —$COOR_1$, each $R_3$ is independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl;

m and p are each independently an integer selected from the group consisting of 0, 1, 2, 3, 4, 5, 6, 7 and 8;

t is a integer selected from the group consisting of 1, 2, 3, 4, 5, 6, 7, 8, 9, 10, 11 and 12;

n is an integer selected from the group consisting of 1, 2, 3, 4, 5, 6, 7, 8, 9, and 10;

or a salt or a stereoisomer thereof.

2. The compound of claim 1, wherein n is 5.

3. The compound of claim 1, wherein the ratio of SA:D:Am is about 42:4:82.

4. The compound of claim 1, wherein the ratio of SA:D:Ac:Am is about 42:4:56:26.

5. The compound of claim 1, wherein the ratio of SA:D:PP:Am is about 42:4:40:42.

6. The compound of claim 1, wherein TG is selected from the group consisting of: cRGD, folic acid, peptide, peptidomimetic, antibody, and antibody fragments.

7. The compound of claim 6, wherein the antibody or antibody fragment is selected from the group consisting of integrins, folate receptor, somatostatin receptor, EGFR, tenascin, CXCR7, PD-L1, CSF1R, c-Met, HGF, Fab, Fab', F(ab')2, single chain antibody, nanobody, minibody, diabody, and CXCR4.

8. The compound of claim 1, wherein D is selected from the group consisting of:

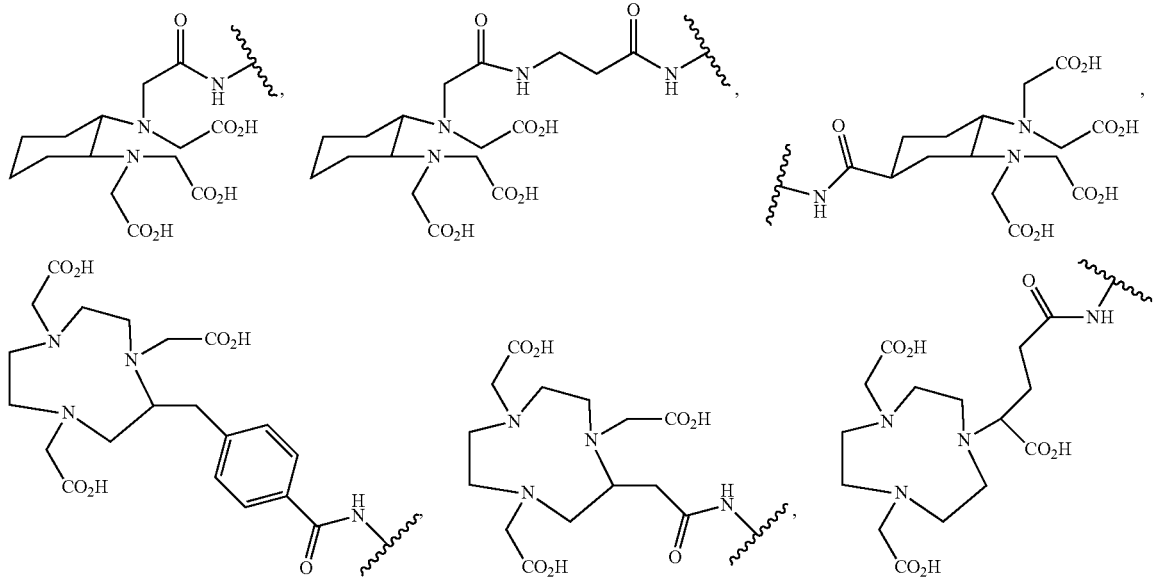

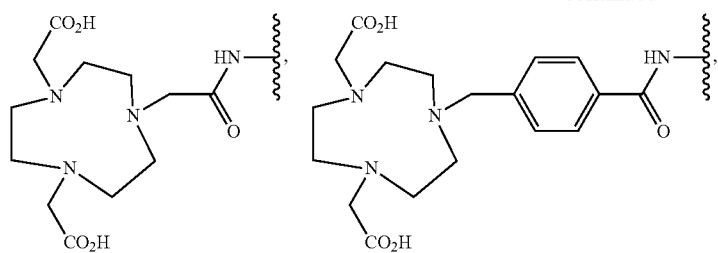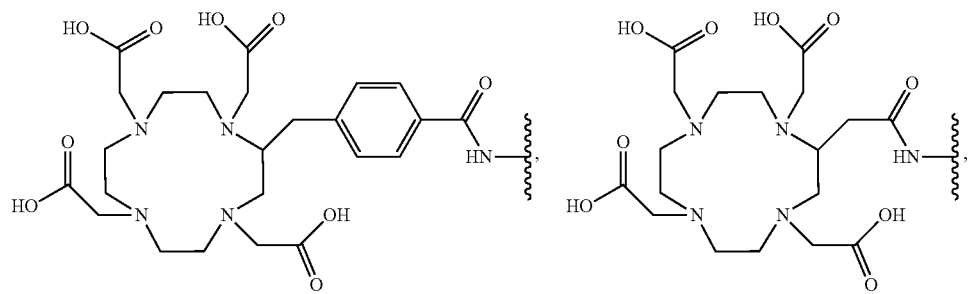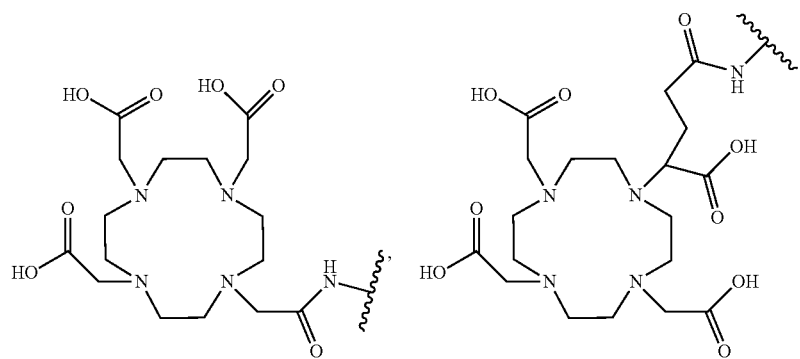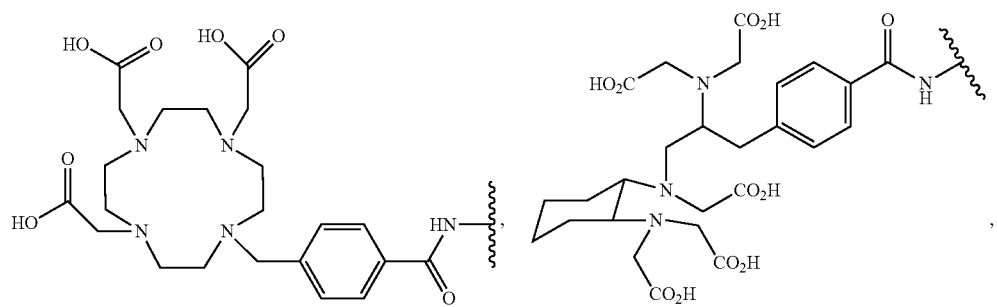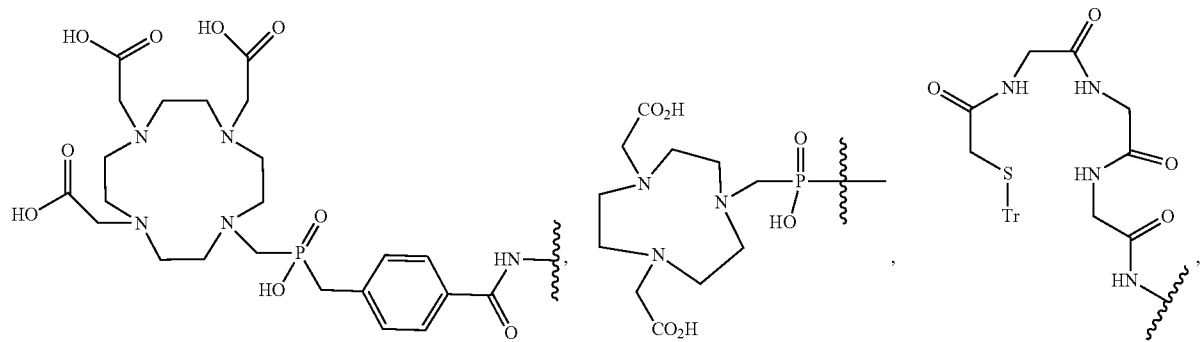

-continued

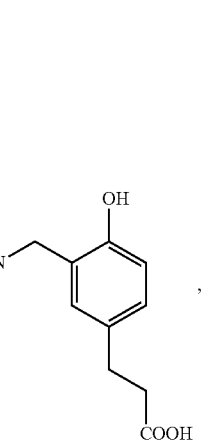
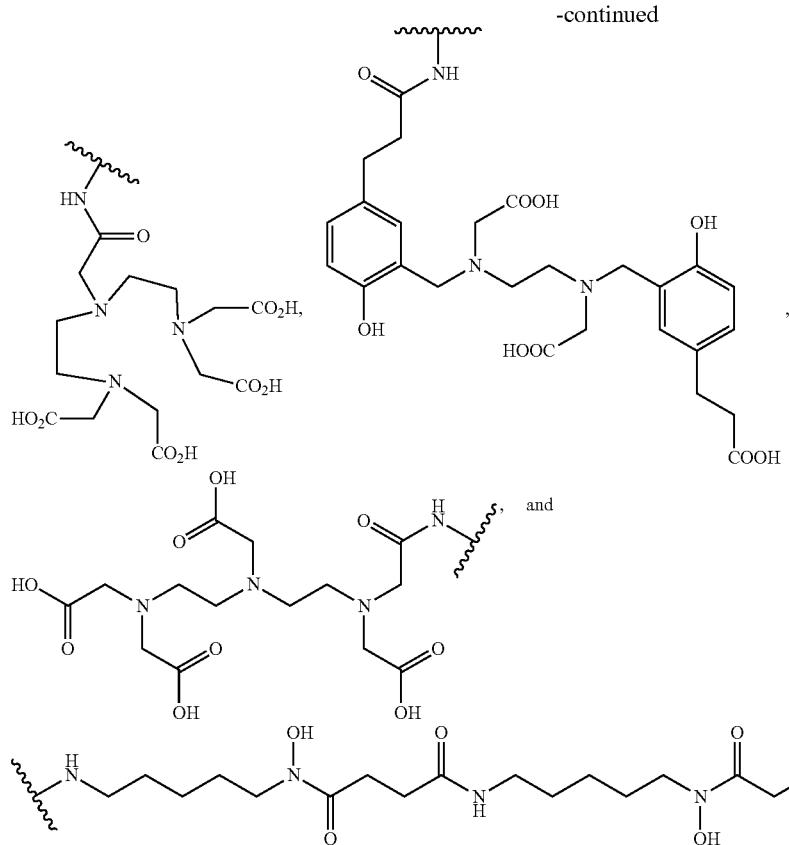
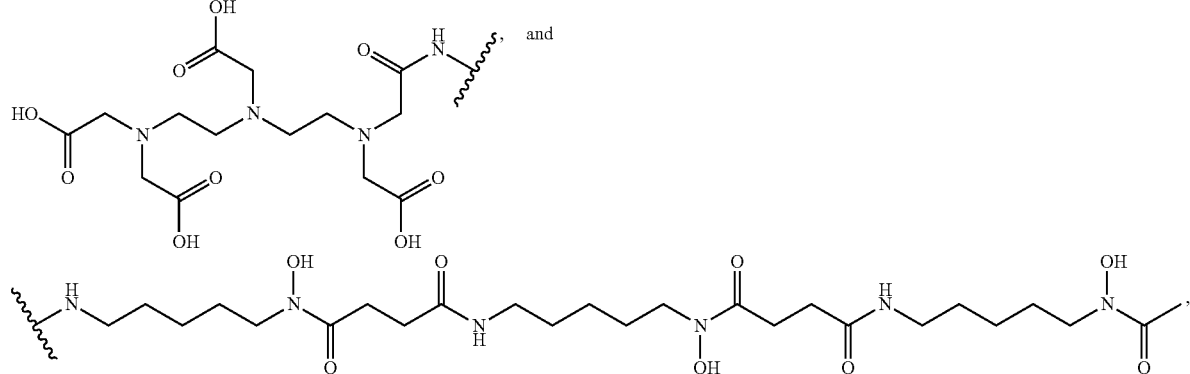

, and or a pharmaceutically acceptable salt thereof.

9. The compound of claim 8, wherein the metal is selected from the group consisting of Cu, Ga, Zr, Y, Tc, In, Lu, Bi, At, Ac, R, and Sr.

10. The compound of claim 9, wherein the metal is a radiometal and is selected from the group consisting of $^{64}$Cu, $^{67}$Cu, $^{68}$Ga, $^{60}$Ga, $^{89}$Zr, $^{86}$Y, $^{94m}$Tc, $^{111}$In, $^{67}$Ga, $^{99m}$Tc, $^{177}$Lu, $^{213}$Bi, $^{212}$Bi, $^{90}$Y, $^{211}$At, $^{225}$Ac, $^{223}$R, and $^{89}$Sr.

11. The compound of claim 1, wherein the compound is selected from the group consisting of:

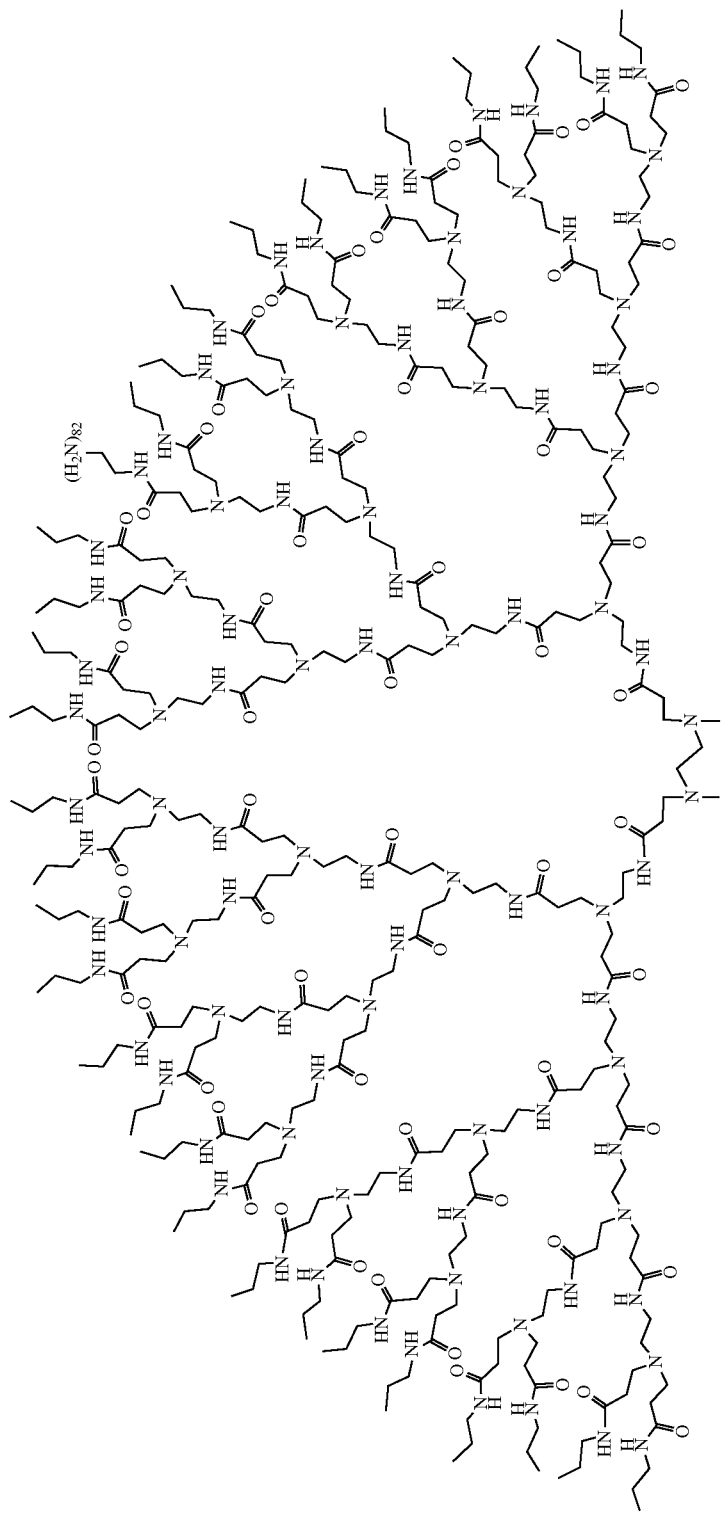

-continued
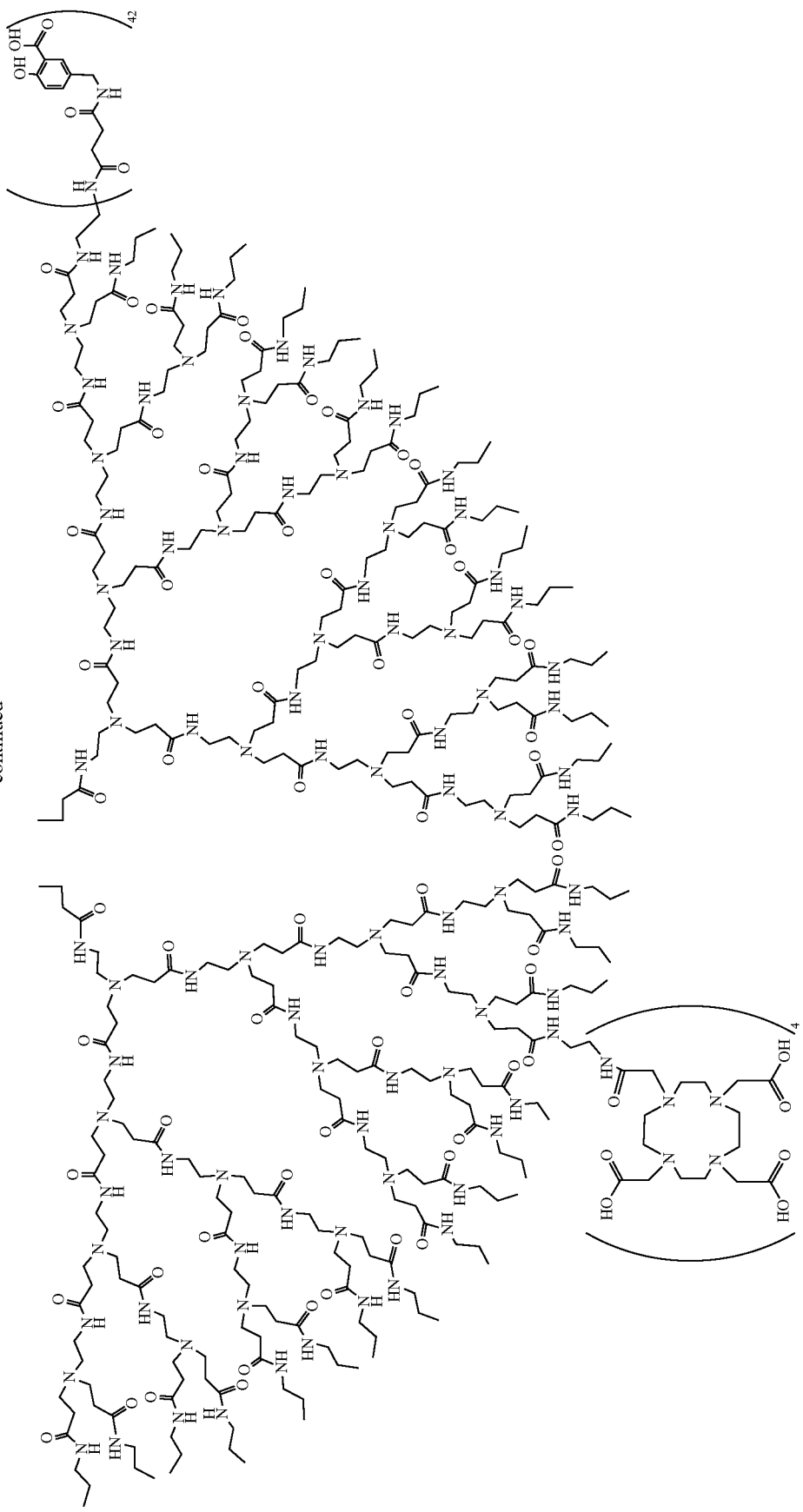
G5-SA-D-Ac:

-continued
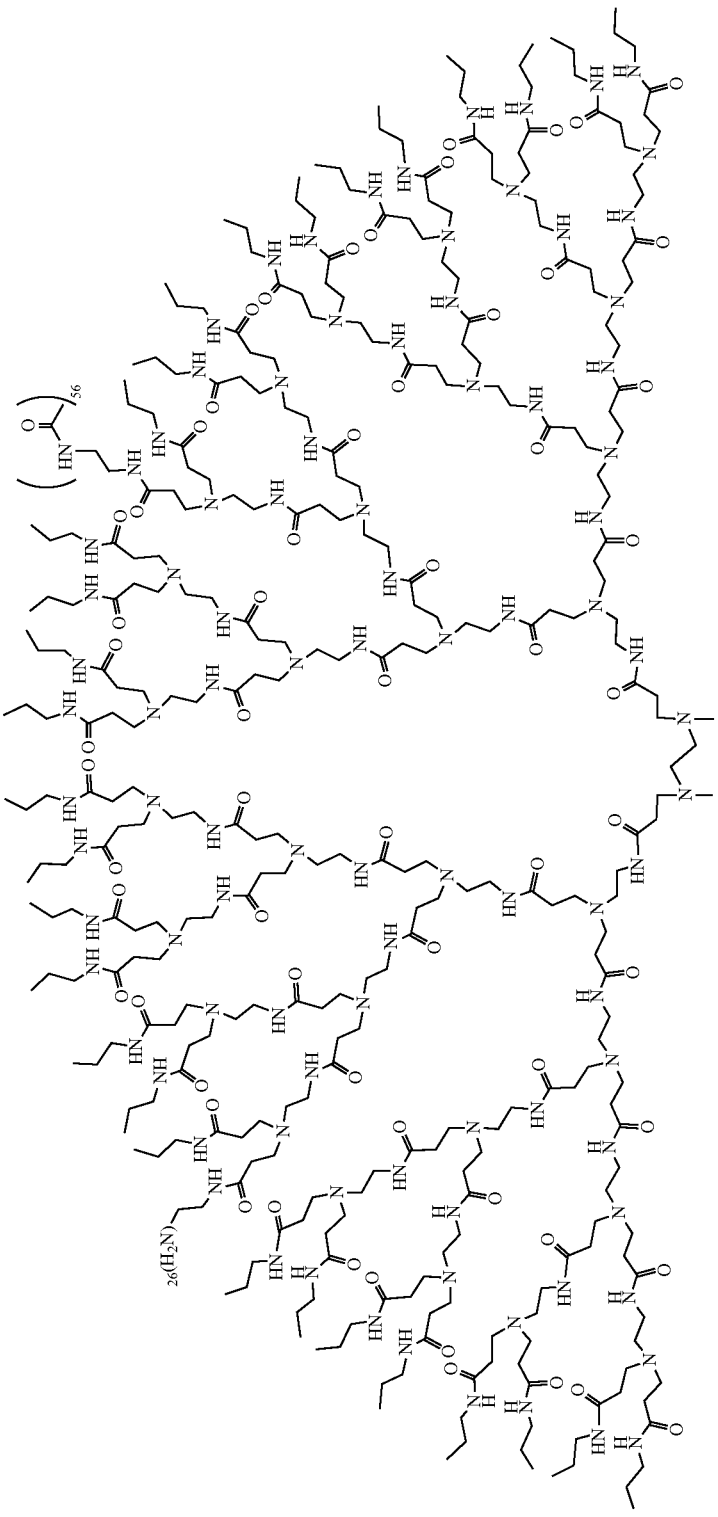

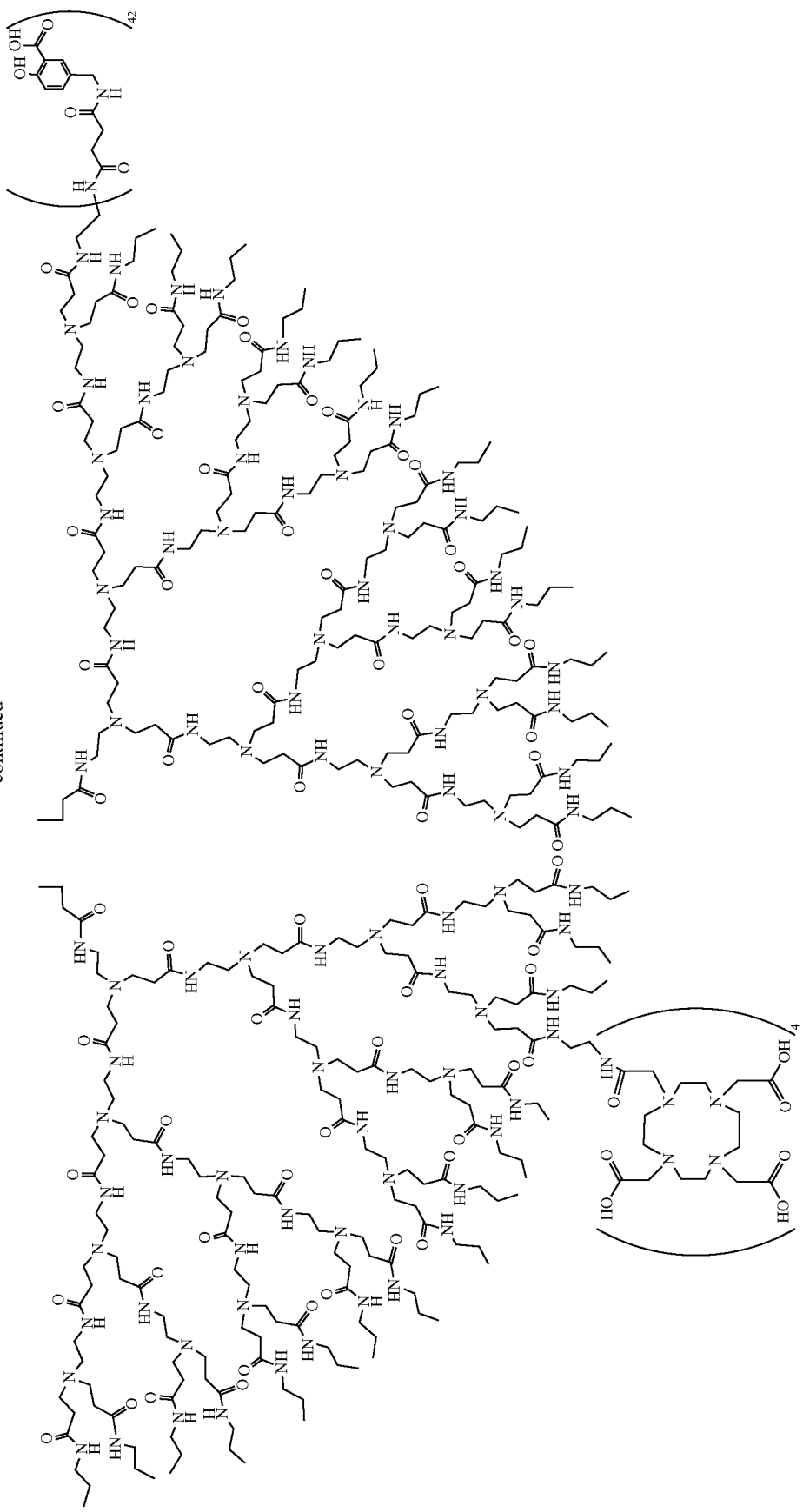
G5-SA-D-Diol:

-continued
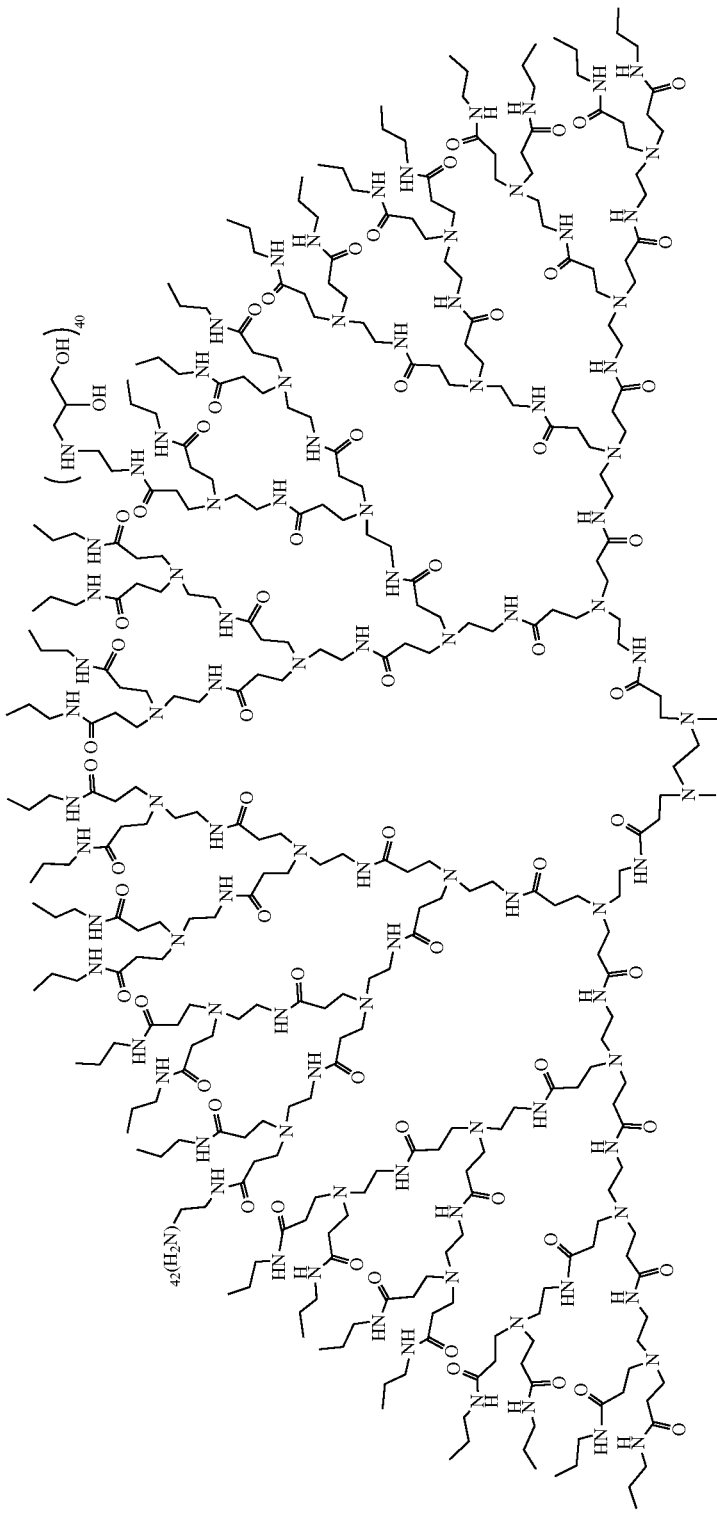

-continued
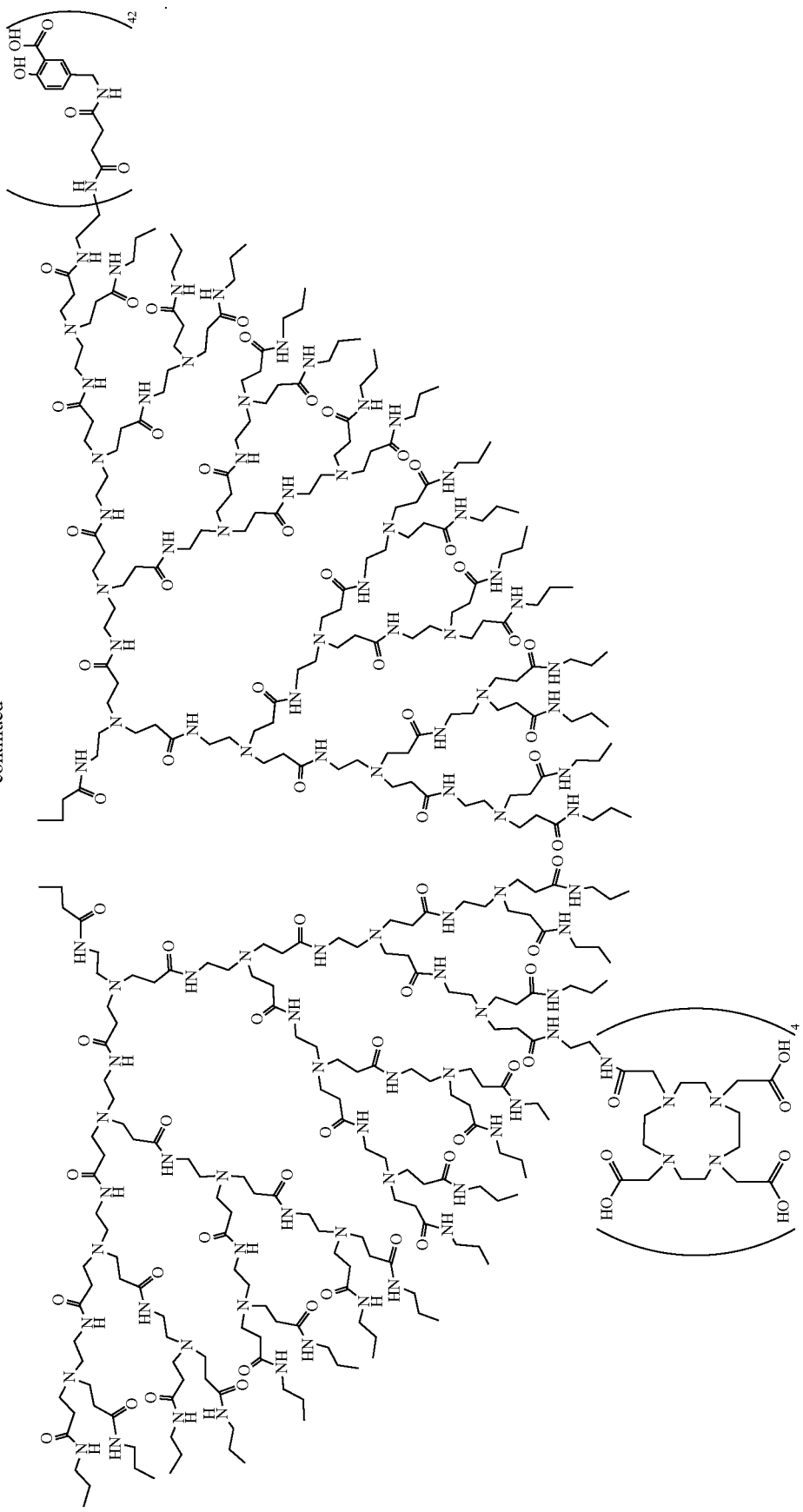

12. A pharmaceutical composition comprising a compound of claim 1, and a pharmaceutically acceptable carrier, diluent, or excipient.

13. A method for producing a magnetic resonance imaging (MRI) of a target, comprising: administering and/or contacting the target with an effective amount of a magnetic resonance imaging contrast agent; and
imaging the target using a Chemical Exchange Saturation Transfer (CEST) or frequency labeled exchange (FLEX) based MRI technique to produce the MR image of the target,
wherein the MRI contrast agent is a compound of formula (I), or a salt or stereoisomer thereof:

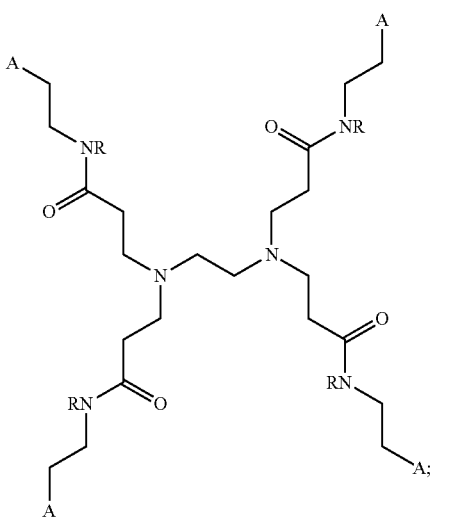

(I)

wherein:
each A is

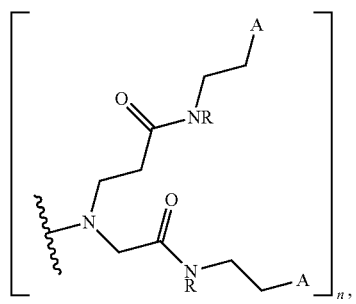

wherein each A' is independently selected from the group consisting of

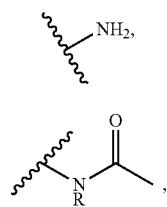

(Am)

(Ac)

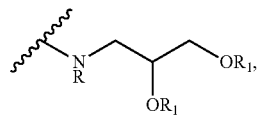

(PP)

a metal chelating moiety (D) optionally comprising a metal or a radiometal suitable for treating or imaging, a therapeutic agent (T), a targeting agent (TG), an imaging agent (IM), PEG-X wherein PEG is polyethylene glycol and X is

or a targeting agent (TG), and —NR-L-W—$(CH_2)_m$-SA, provided that at least one of A' is —NR-L-W—$(CH_2)_m$-SA,
L is a linking group selected from the group consisting of —$(CH_2)_m$—, —C(=O)—$(CH_2)_m$—, —$(CH_2-CH_2-O)_t$—, —C(=O)—$(CH_2-CH_2-O)_t$—, —(O—$CH_2-CH_2)_t$—, —C(=O)—(O—$CH_2-CH_2)_t$—, —C(=O)—$(CHR_2)_m$—$NR_3$—C(=O)—$(CH_2)_m$—, —C(=O)—$(CH_2)_m$—O—C(=O)—$NR_3$—$(CH_2)_p$—, —C(=O)—$(CH_2)_m$—$NR_3$—C(=O)—O—$CH_2)_p$—, —C(=O)—$(CH_2)_m$—$NR_3$—C(=O)—$NR_3$—$(CH_2)_p$—, —C(=O)—$(CH_2)_m$—$NR_3$—C(=O)—$(CH_2)_p$—, —C(=O)—$(CH_2)_m$—C(=O)—$NR_3$—$(CH_2)_p$—, —C(=O)—$(CH_2)_m$—$NR_3$—C(=O)—$NR_3$—$(CH_2)_p$—, —C(=O)—$(CH_2)_m$—$NR_1$—C(=O)—$NR_3$—$(CH_2)_p$—, —C(=O)—$(CH_2)_m$—O—C(=O)—$NR_3$—, —C(=O)—$CH_2)_m$—O—C(=O)—$NR_3$—$(CH_2)_p$—, —C(=O)—$(CH_2)_m$—$NR_3$—C(=O)—O—$(CH_2)_p$—, polyethylene glycol, glutaric anhydride, albumin, lysine, and amino-acid;
W is selected from the group consisting of —NR—C(=O)—, —C(=O)—NR—, —S—, —O—, and —$SO_2$—;
SA is

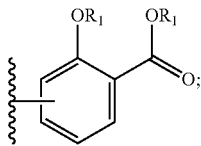

each R is independently selected from the group consisting of H and $C_1$-$C_4$ alkyl;
each $R_1$ is independently selected from the group consisting of H, Na, $C_1$-$C_4$ alkyl, and a protecting group;
each $R_2$ is independently selected from the group consisting of hydrogen, and —$COOR_1$,
each $R_3$ is independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl;
m and p are each independently an integer selected from the group consisting of 0, 1, 2, 3, 4, 5, 6, 7 and 8;

t is a integer selected from the group consisting of 1, 2, 3, 4, 5, 6, 7, 8, 9, 10, 11 and 12;
n is an integer selected from the group consisting of 1, 2, 3, 4, 5, 6, 7, 8, 9, and 10;
or a salt or a stereoisomer thereof.

14. The method of claim 13, wherein n is 5.

15. The method of claim 13, wherein the ratio of SA:D:Am is about 42:4:82.

16. The method of claim 13, wherein the ratio of SA:D:Ac:Am is about 42:4:56:26.

17. The method of claim 13, wherein the ratio of SA:D:PP:Am is about 42:4:40:42.

18. The method of claim 13, wherein TG is selected from the group consisting of: cRGD, folic acid, peptide, peptidomimetic, antibody, and antibody fragments.

19. The method of claim 18, wherein the antibody or antibody fragment is selected from the group consisting of integrins, folate receptor, somatostatin receptor, EGFR, tenascin, CXCR7, PD-L1, CSF1R, c-Met, HGF, Fab, Fab', F(ab')2, single chain antibody, nanobody, minibody, diabody, and CXCR4.

20. The method of claim 13, wherein D is selected from the group consisting of:

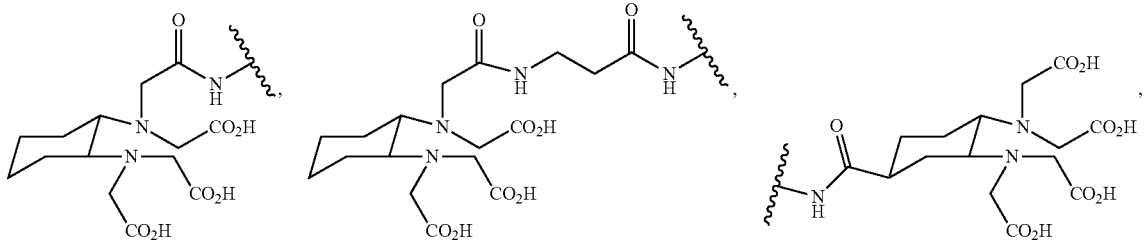

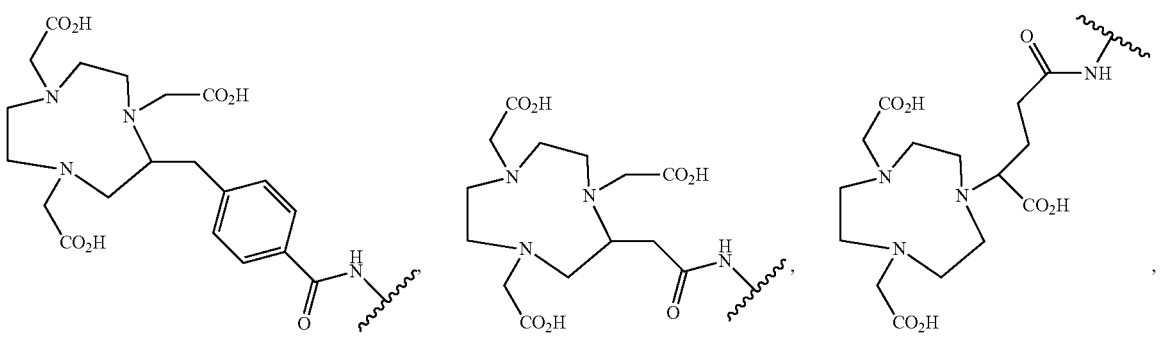

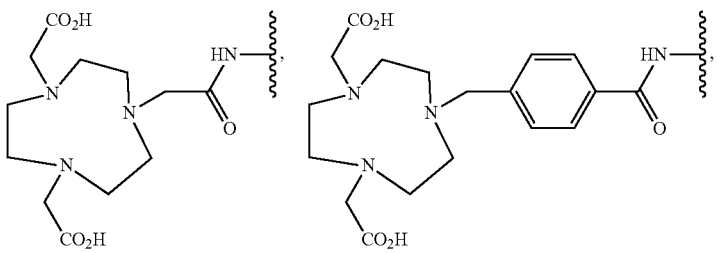

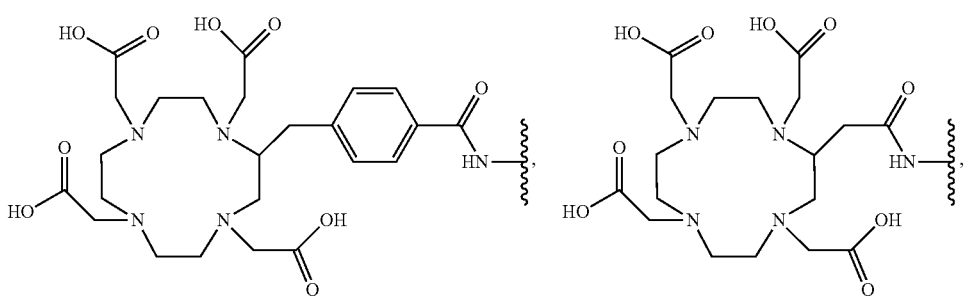

-continued
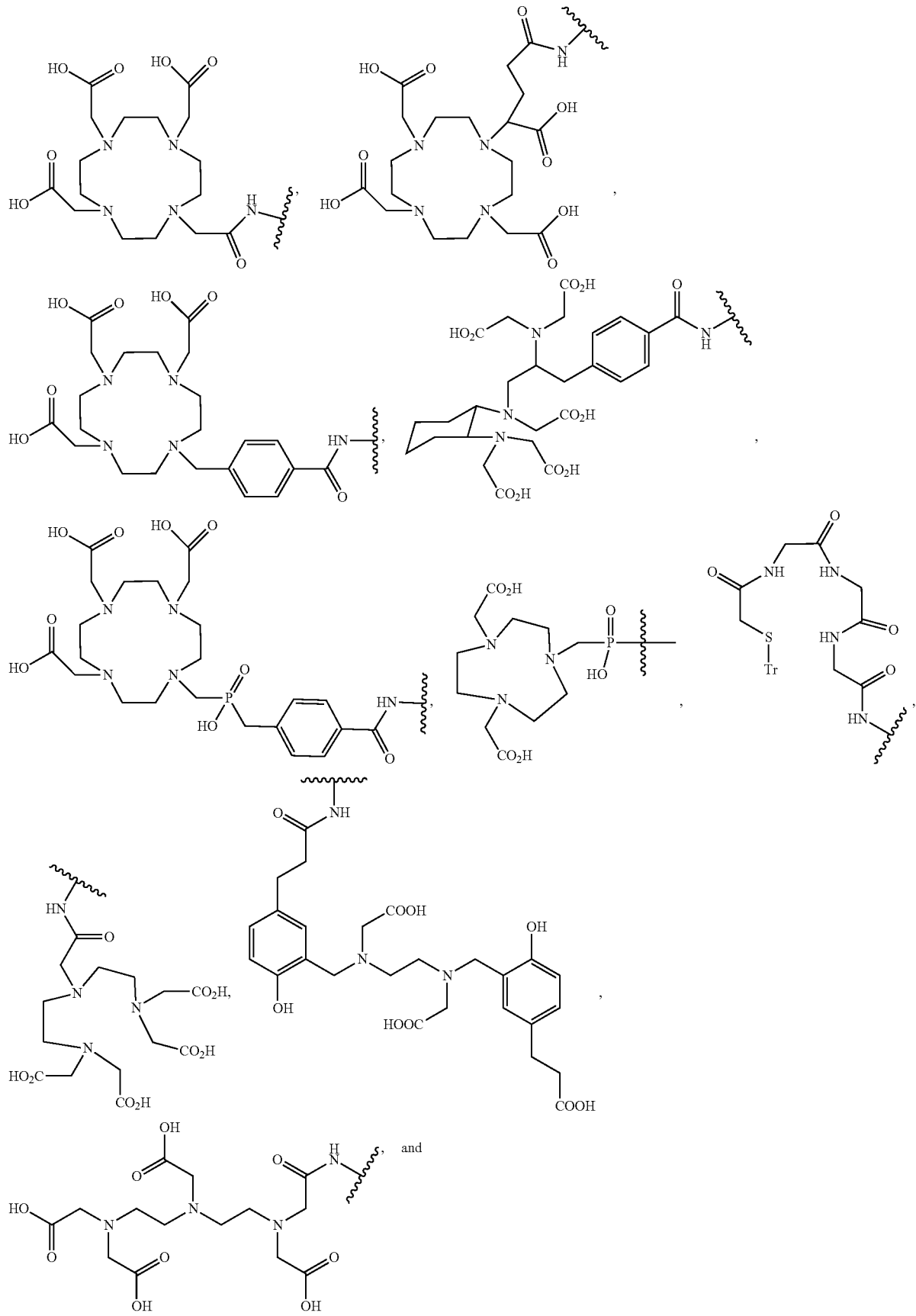

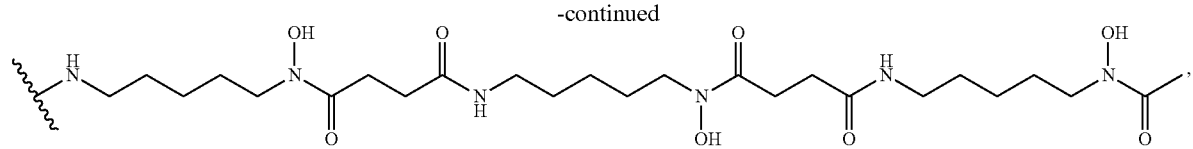
or a pharmaceutically acceptable salt thereof.
21. The method of claim 13, wherein the dendrimer of formula (I) is selected from the group consisting of:

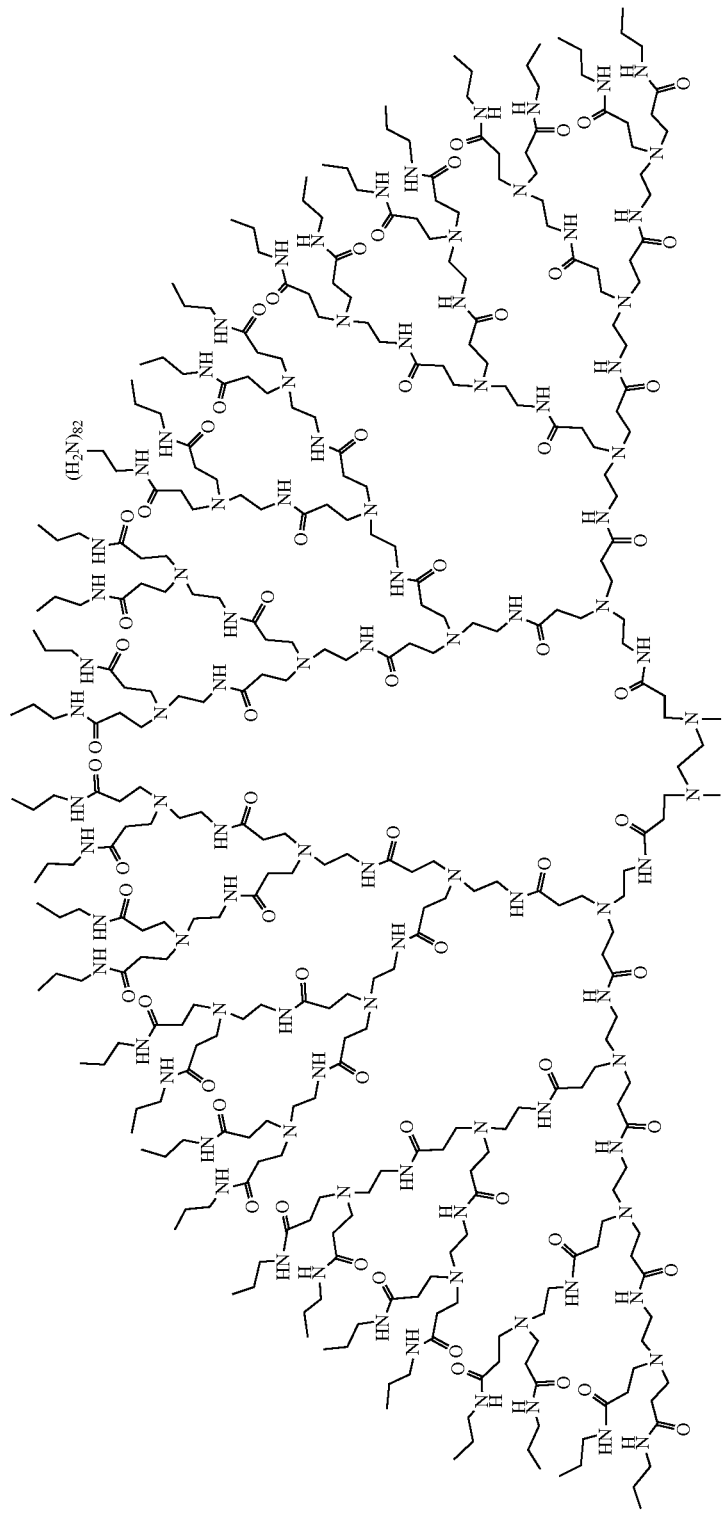

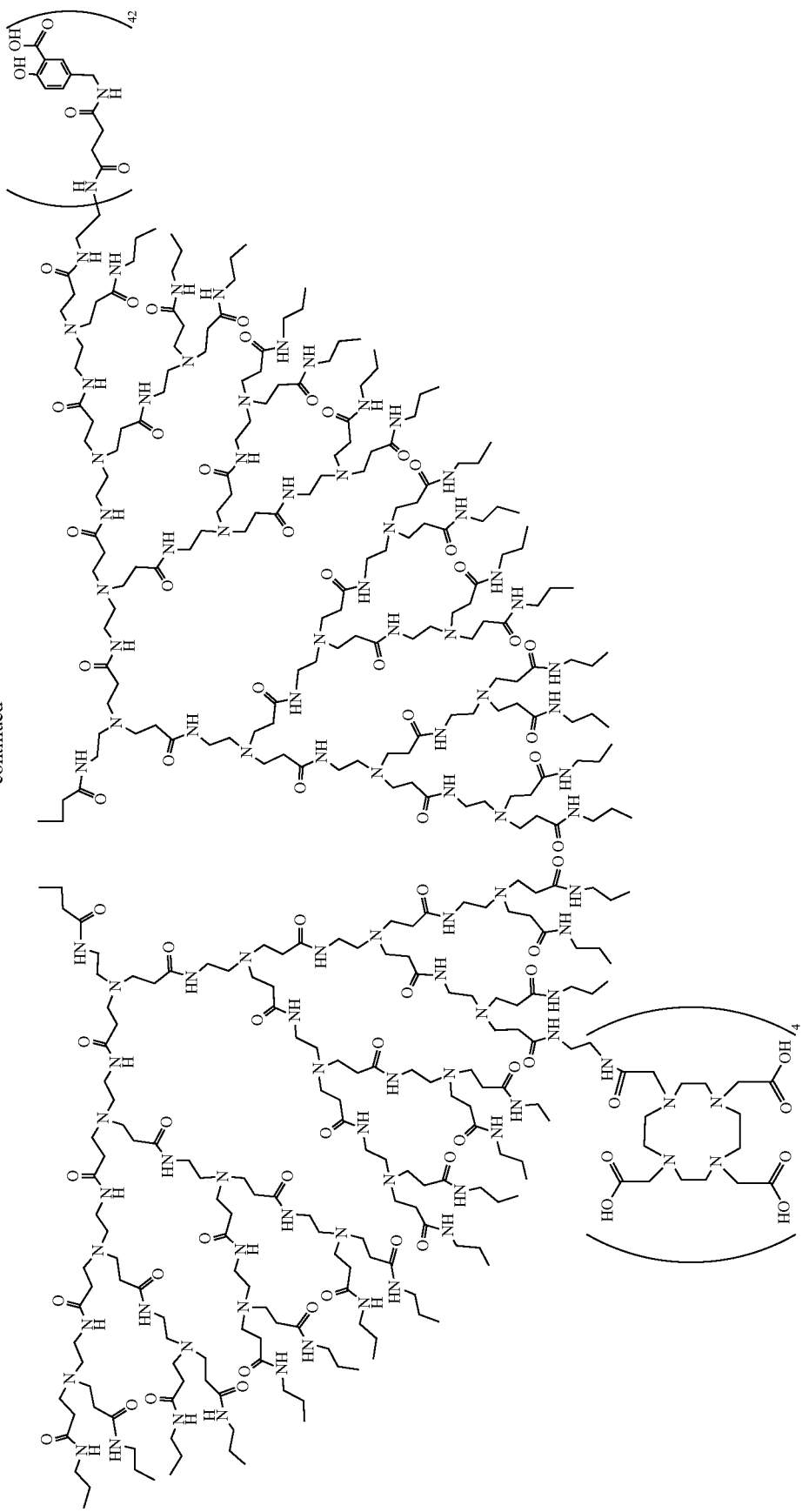

-continued
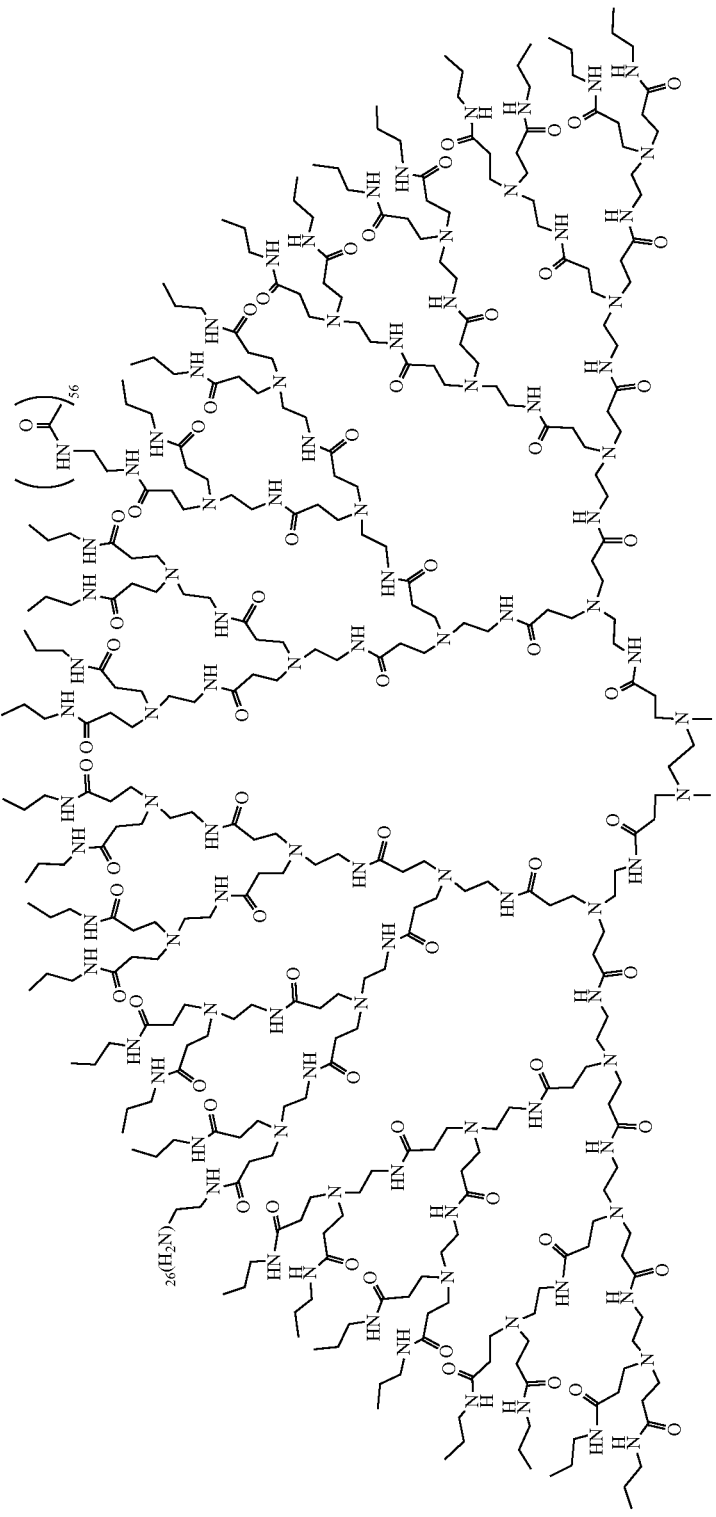

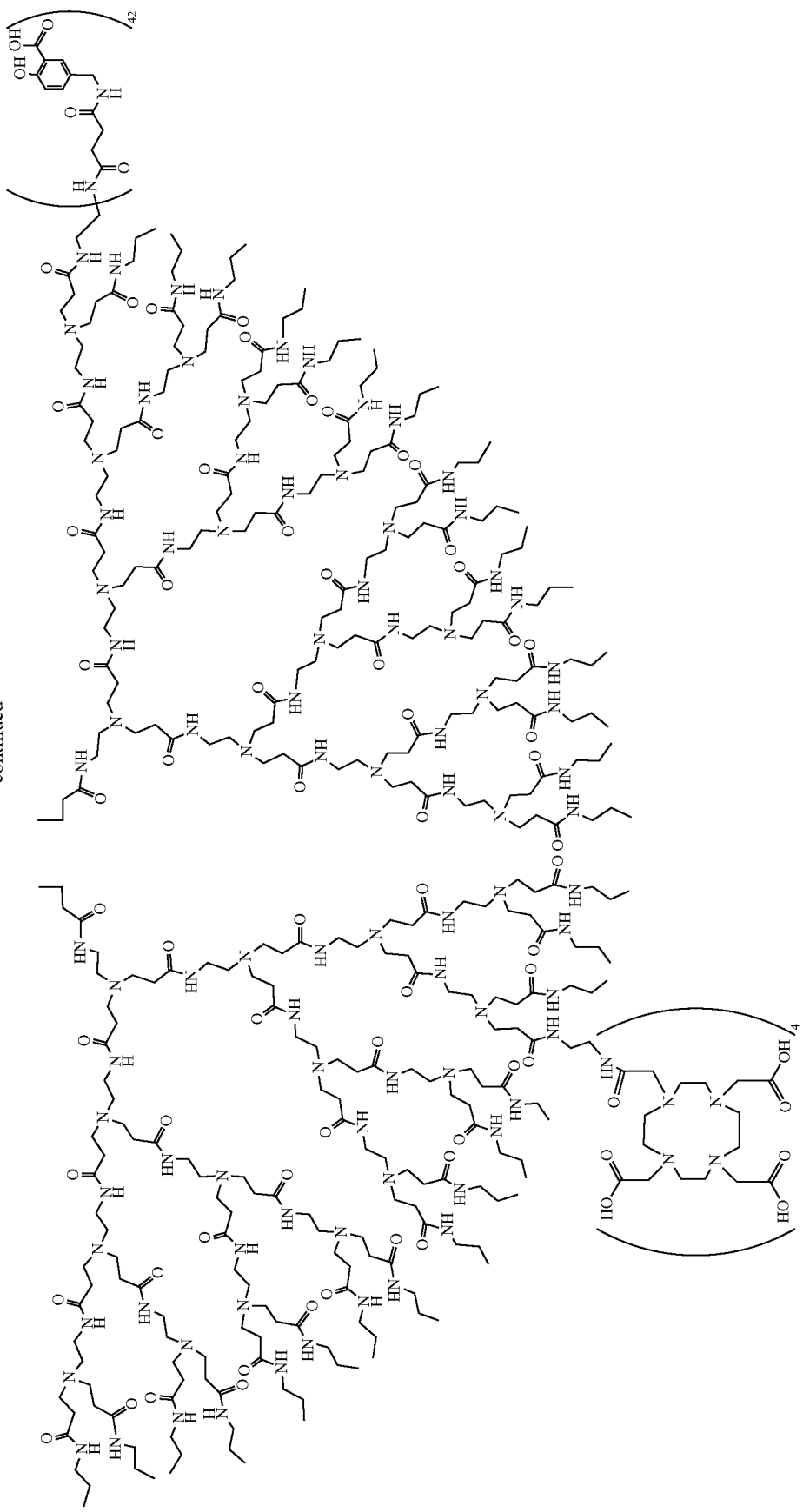
G5-SA-D-Diol:

-continued
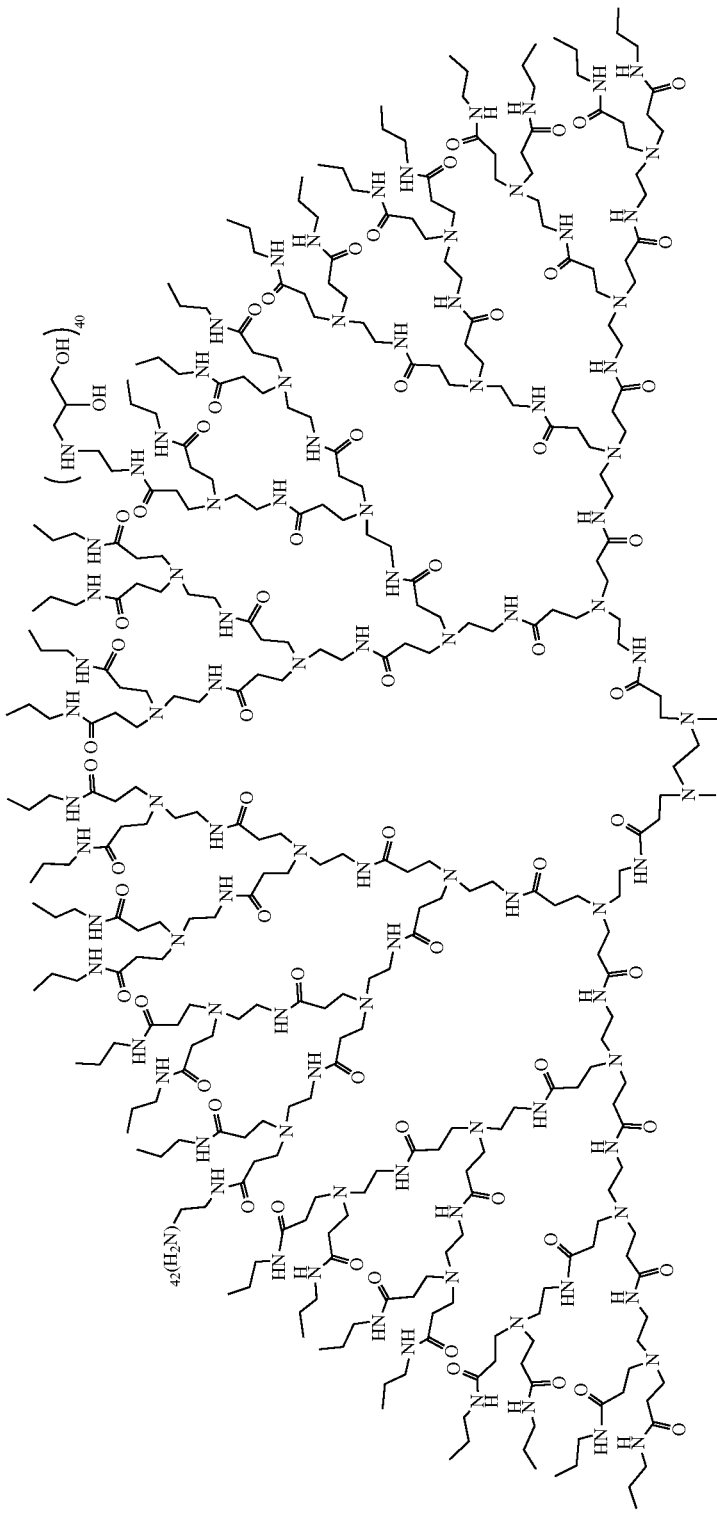

-continued
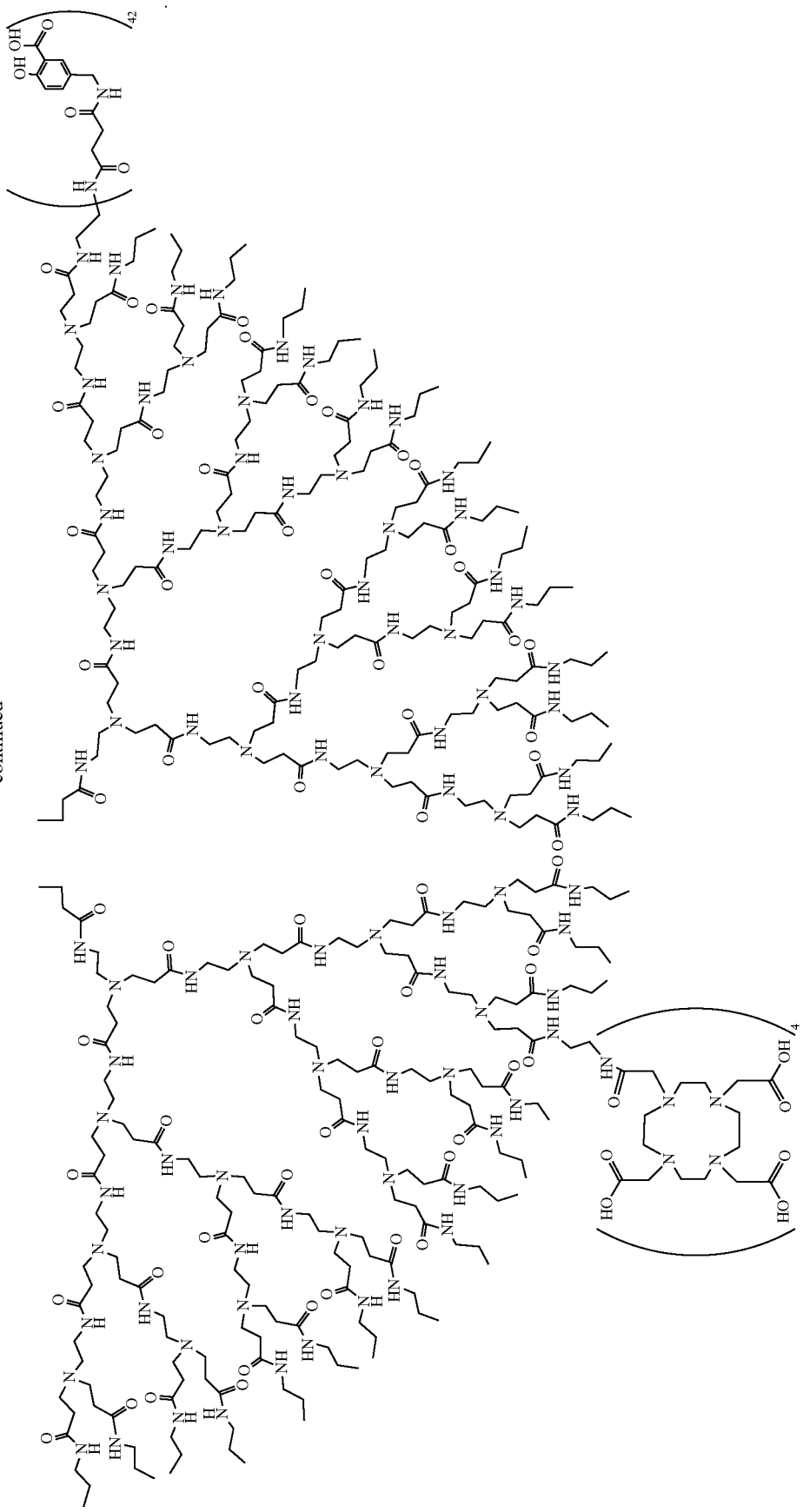

22. The method of claim 13, wherein the target is selected from the group consisting of a cell, a biological tissue, an organ, a tumor, a ligand, a biomarker, a therapeutically active agent, a metal ion, a chemotherapeutic, an antigen, a nanoparticle, a receptor, and a cation.

23. The method of claim 13, wherein the target is in vitro, in vivo, or ex vivo.

24. The method of claim 13, wherein the target is present in a subject.

25. The method of claim 13, further comprising measuring a chemical shift change of exchangeable protons in said MRI contrast agent.

26. The method of claim 13, wherein the target is imaged using CEST MRI.

27. The method of claim 13, wherein the target is imaged using FLEX MRI.

28. The method of claim 13, wherein the MR imaging is performed in combination with positron emission tomography (PET) and the radiometal is selected from the group consisting of $^{64}Cu$, $^{67}Cu$, $^{68}Ga$, $^{60}Ga$, $^{89}Zr$, $^{86}Y$, and $^{94m}Tc$.

29. The method of claim 13, wherein the MR imaging is performed in combination with single-photon emission computed tomography (SPECT) and the radiometal is selected from the group consisting of $^{111}In$, $^{67}Ga$, $^{99m}Tc$, and $^{177}Lu$.

30. The method of claim 13, further comprising diagnosing, based on the MR image of the target, a disease or condition in a subject.

31. The method of claim 13, further comprising monitoring, based on the MR image of the target, progression or regression of a disease or condition in a subject.

32. The method of claim 13, further comprising treating a disease or condition in a subject.

33. The method of claim 32, wherein the radiometal suitable for radiotherapy is selected from the group consisting of $^{177}Lu$, $^{213}Bi$, $^{212}Bi$, $^{90}Y$, $^{211}At$, $^{225}Ac$, $^{223}R$, and $^{89}Sr$.

34. The method of claim 30, wherein the disease or condition is selected from the group consisting of cancer and lymphatic vessels diseases.

35. The method of claim 34, wherein the disease or condition is brain cancer.

36. The method of claim 13, further comprising monitoring a site specific delivery of the therapeutic agent by localizing the dendrimer to the site in need of treatment and releasing the therapeutically active agent at the site in need of treatment.

37. The method of claim 13, further comprising identifying sentinel lymph nodes for removal using sentinel lymph node biopsies.

* * * * *